(12) United States Patent
Grothe et al.

(10) Patent No.: US 9,453,016 B2
(45) Date of Patent: Sep. 27, 2016

(54) TERPENOID SPIRO KETAL COMPOUNDS WITH LXR AGONISTS ACTIVITY, THEIR USE AND FORMULATIONS WITH THEM

(75) Inventors: Torsten Grothe, Bochum (DE); Marc Stadler, Niederkirchen (DE); Bärbel Köpcke, Dortmund (DE); Ernst Roemer, Dorsten (DE); Jens Bitzer, Dortmund (DE); Philipp Wabnitz, Düsseldorf (DE); Thomas Küper, Reken (DE)

(73) Assignees: Torsten Grothe, Bochum (DE); Marc Stadler, Niederkirchen (DE)

( * ) Notice: Subject to any disclaimer, the term of this patent is extended or adjusted under 35 U.S.C. 154(b) by 59 days.

(21) Appl. No.: 13/994,447

(22) PCT Filed: Dec. 8, 2011

(86) PCT No.: PCT/EP2011/006157
§ 371 (c)(1),
(2), (4) Date: Aug. 8, 2013

(87) PCT Pub. No.: WO2012/079721
PCT Pub. Date: Jun. 21, 2012

(65) Prior Publication Data
US 2013/0338219 A1     Dec. 19, 2013

(30) Foreign Application Priority Data
Dec. 14, 2010 (EP) ................... 10015607

(51) Int. Cl.
| | | |
|---|---|---|
| A61K 31/35 | (2006.01) |
| C07D 493/00 | (2006.01) |
| C07D 471/10 | (2006.01) |
| A61K 31/56 | (2006.01) |
| A61K 31/58 | (2006.01) |
| A61K 36/07 | (2006.01) |

(52) U.S. Cl.
CPC ............. *C07D 471/10* (2013.01); *A61K 31/56* (2013.01); *A61K 31/58* (2013.01); *A61K 36/07* (2013.01)

(58) Field of Classification Search
CPC .... A61K 31/156; A61K 31/58; A61K 36/07; C07D 471/10
USPC .......................................... 514/453; 549/344
See application file for complete search history.

(56) References Cited

PUBLICATIONS

Su et al, Black soybean promotes the formation of active components with antihepatoma activity in the fermentation product of Agaricus blazei, 2008, Journal of Agricultural and Food Chemistry, 56(20), p. 9447-9454.*

*Primary Examiner* — T. Victor Oh
(74) *Attorney, Agent, or Firm* — Edward E. Sowers; Brannon Sowers & Cracraft PC

(57) ABSTRACT

The invention relates to compositions and methods (with regard to animals and humans) for utilizing an extract and/or one or more natural spiro triterpenoids and derivatives thereof alone or as a supplement. Certain materials utilized are from the blazeispirol family, obtainable from *Agaricus* species. Treatments include the prophylactic and/or therapeutic treatment of a disease, disorder or condition that responds to the modulation of Liver X receptor, as well as corresponding methods of treatment, the manufacture of a pharmaceutical and nutraceutical formulation for said treatment. The invention also relates to the use of the extract and compound(s) in the treatment or in the preparation of a medicament (e.g. a nutraceutical) for the prophylactic and/or therapeutic treatments, as well as their preparation. It also relates to pharmaceutical or nutraceutical formulations described herein which are useful in prophylactic and therapeutic treatments. They can also be used for non-therapeutic, e.g. cosmetic, purposes.

4 Claims, 2 Drawing Sheets

TERPENOID SPIRO KETAL COMPOUNDS WITH LXR AGONISTS ACTIVITY, THEIR USE AND FORMULATIONS WITH THEM

CROSS-REFERENCES TO RELATED APPLICATIONS

This application is a National Stage filing of International Application PCT/EP 2011/006157, filed Dec. 8, 2011, claiming priority to European Application No. EP 10 015 607.4 filed Dec. 14, 2010, entitled "TERPENOID SPIRO KETAL COMPOUNDS WITH LXR AGONISTS ACTIVITY, THEIR USE AND FORMULATIONS WITH THEM." The subject application claims priority to PCT/EP 2011/006157, and to European Application No. EP 10 015 607.4 and incorporates all by reference herein, in their entirety.

BACKGROUND OF THE INVENTION

The genus *Agaricus* Linnaeus 1753 belongs to family Agaricaceae (Basidiomycota) and comprises over 200 species in its current circumscription (Kirk et al. 2008, Ainsworth & Bisby's dictionary of the Fungi, Tenth Edition, Wallingford, p. 13-14), many of which are edible mushrooms. They are saprotrophic and occur in natural habitats such as meadows and forests, but even in habitats heavily influenced by humans all over the tropical and temperate climates of the world. Several species of *Agaricus*, such as the Button Mushroom, *Agaricus bisporus*, can be cultivated on commercial scale and are being sold as food all over the world. The genus is divided into sections, according to morphological (habit of the fruiting bodies, morphology of basidia, basidiospores, and cystidia), and chemotaxonomic (odour, colouring reactions upon injury) characteristics. This classification was recently confirmed and stabilized by using molecular phylogenetic methods, which also allowed for safely establishing the synonymy of certain species that have been described independently by different mycologists from different parts of the world. In particular nuclear ribosomal desoxyribonucleic acid (nrDNA) data, and preferable the 5.8S/ITS regions, are being widely used to characterize fungal species. The availability of universal PCR primers for amplification of fungal nrDNA (White, T. J. et al. 1990. In: PCR Protocol: A Guide to Methods and Applications. Eds. M. A. Innis et al. Academic Press, New York. pp. 315-322) has even facilitated sequencing of old herbarium specimens, and the work on the taxonomy and phlyogeny of *Agaricus* cited below also relied on such methods. The genus *Agaricus* is traditionally being divided in several sections, of which section Arvenses (which includes *Agaricus subrufescens* and several other edible mushrooms, such as *Agaricus arvensis*) is the most important in relation to this invention. Other important sections include e.g., sect. Xanthodermatei (including most of the toxic species in *Agaricus*; see Kerrigan et al., Mycologia (2005) 97: 1292-1315 and sect. Bivelares (including *Agaricus bisporus*; see Kerrigan et al., Mycologia, (2008) 100: 876-892), and sect. *Agaricus*, including the type species, the edible horse mushroom, *Agaricus campestris*. The species included in those sections are not subject of the present invention, as they can apparently not produce the beneficial compounds.

A world-wide renowned expert in the taxonomy, Kerrigan (Mycologia (2005) 97(1): 12-24), has recently summarized the taxonomic history of *Agaricus subrufescens*, and his study was validated by morphological studies of type specimens, as well as by molecular phylogenetic studies on various representatives that have been treated as *Agaricus subrufescens* or synonyms of this name. In this publication, the currently valid name is given as *Agaricus subrufescens* Peck, New York State. Mus. Ann. Rep. (1893) 46:105. The basionym of this name is *Psalliota subrufescens* Kauff. The Agaricaceae of Michigan (1918) 239. Accepted synonyms are *Agaricus rufotegulis* Nauta Persoonia (1999) 17: 230 and *Agaricus brasiliensis* Wasser, Didukh, de Amazonas & Stamets. Int. J. Med. Mush. (2002) 4:274. Since nomenclature and taxonomic aspects are important to understand the scope of the current invention, their taxonomic history of the respective *Agaricus* species is explained in detail further below.

The species *Agaricus blazei* Murill was erected by the American mycologist Murrill (1945), based on material collected in Florida, USA and named for the collector of the specimen, whose surname was Blaze. The name *Agaricus blazei* was eventually used by the Belgian mycologist Heinemann for a fungus from Brazil with medicinal properties that has since then been widely referred to as *Agaricus blazei* in the literature. However, Wasser et al. (Int J Med Mush (2002) 4: 267-290) demonstrated that this name was misapplied by Heinemann, who have obviously misidentified the medicinally important species. According to their meticulous morphological studies on type and authentic material of both species, it became clearly evident that *Agaricus blazei* differed from the Brazilian fungus referred to as "*Agaricus blazei*" by Heinemann (Bull Jard Bot Belgium (1993) 62: 365-368) in the morphology of its fruiting bodies, the microscopic characters of the pileal covering, the presence of cheilocystidia on the lamellae, and in its basidiospore size. All these characters are regarded as valid criteria for differentiation of species in the genus *Agaricus*, and if two given taxa in the genus *Agaricus* differ in all four characteristics mentioned, it can be assessed with certainty that they represent two different species.

The name "*Agaricus blazei* Murrill" sensu Heinemann (1993) should therefore not be used anymore to characterize the economically important fungus, for which Wasser et al. (2002) had proposed a new name, *Agaricus brasiliensis*.

Wasser et al. (Intl J Med Mush (2002) 4: 267-290) further proposed that *Agaricus blazei* sensu stricto is a rare, endemic species of North America that has been collected rather infrequently in Southeastern USA. The medicinal properties of *Agaricus blazei* sensu stricto are unknown. There are no reports in the literature suggesting with certainty that this fungus has ever been cultivated, and it even remains unclear whether *Agaricus blazei* actually constitutes an edible species.

On the other hand, Kerrigan (Mycologia (2005) 97(1): 12-24) has meanwhile shown conclusively by using morphological and molecular phylogenetic data, as well as mating studies, that *Agaricus brasiliensis* and *Agaricus subrufescens* are synonyms. Accordingly, the erection of the species *Agaricus brasiliensis* was superfluous, since the older name, *Agaricus subrufescens*, takes preference over *Agaricus brasiliensis*, according to the current rules of the International Botanical Code.

According to Kerrigan (2005) *Agaricus subrufescens* is also a species that was first described from New York State, USA, where it was already cultivated in the $19^{th}$ century on a commercial scale, long before it was first found in Brazil or used as medicinal mushroom in Asia. This means that the economically important fungus is not an exotic, tropical species as had hitherto been assumed by many authors, but has actually been used as food in the Western civilization for over a century. Kerrigan (2005) further reported *Agaricus subrufescens* or synonymous species from Europe, Asia, Hawaii, North and South America, even though it remains unclear which of these records might relate to strains that escaped from cultivation plants into the environment, and which of them would relate to the original geographic distribution of this mushroom.

While all experts appear to agree that the name *Agaricus blazei* should no longer be used for the Brazilian medicinal mushroom, the problem of synonymy of *Agaricus brasiliensis* and *Agaricus subrufescens* is still under discussion. Wasser et al. (Int J Med Mushrooms (2005) 7: 507-511) and Kerrigan (Int J Med Mushrooms (2007) 9(1): 79-83) have both brought forward arguments to justify their taxonomic opinion, relying on different species concepts. A very convincing argument brought forward by Kerrigan is that "single-spore progeny of *A. subrufescens* from North America and another strain from Brazil (by way of Japan) can mate to produce fertile offspring", hence they are synonyms according to a biological species concept, as it is commonly applied in animals and plants.

However, regardless of the taxonomic opinion, there is a problem in nomenclature associated with the use of the name *Agaricus brasiliensis*, sensu Wasser et al., since the same name has been used previously by other mycologists to describe a different fungus. *Agaricus brasiliensis* Fr. 1830 is listed in the databases Mycobank and Index Fungorum (www.mycobank.org & www.indexfungorum.org), two databases on fungal taxonomy and nomenclature that are being maintained by renowned taxonomic experts, as the oldest record of this name, which was already used in 1830 by the Swedish mycologist, Elias Fries. Therefore, the name *A. brasiliensis* Wasser et al. constitutes a later homonym and appears to be illegitimate, according to the rules of the International Botanical Code. Accordingly, it has therefore been listed as illegitimate in Mycobank.

All the above names, their interpretations in the cited literature and their synonyms, in particular including the medicinal fungus that is now still often named *Agaricus blazei*, or occasionally, *Agaricus brasiliensis*, will therefore henceforth be referred to as *Agaricus subrufescens*, following the taxonomic concept proposed by Kerrigan outlined above, to avoid ambiguities.

As molecular techniques were more widely employed in all disciplines of biology, large databases were created on the Internet to allow scientists to deposit their DNA, RNA, and protein sequences in order to facilitate comparison of such data. This also holds true for ribosomal DNA sequences, which are in widespread use for characterization of fungal organisms and are increasingly used to verify and refine taxonomic and phylogenetic concepts. These databases, such as GenBank (www.ncbi.nlm.nih.gov/genbank) and EMBL (www.embl.de), are particularly helpful in many aspects of modern natural science, so long as the data deposited therein can be considered reliable and genuine. However, it should be noted that it is the depositors' responsibility to provide correct identifications of the species when depositing such DNA sequence data in the afore mentioned Internet databases, which therefore contain many data of poorly characterized or even misidentified specimens. This problem has been addressed, with particular emphasis on fungi, by Bridge et al. New Phytologist (2003) 160: 43-48. These sequences can be identified by comparison of their similarity with other DNA sequence data derived from material that was thoroughly studied and may therefore be regarded as genuine. For instance, regarding *Agaricus subrufescens* sensu Kerrigan (2005), all DNA sequence data of ITS/5.8S ribosomal DNA which the author found to correspond with his morphological species concept, showed also a high similarity to one another in the concurrent phylogenetic tree. There are, however, sequences that appear to belong to this group of *Agaricus subrufescens* sensu Kerrigan, which were deposited under different names. For instance, this includes the sequence of a fungus named "*Agaricus sylvaticus*" by Huang and Hseu (Taiwanese Journal of Agricultural Chemistry and Food Science 2004, 42: 75-82), which was derived from a strain that was sent to the authors as a gift by a Japanese colleague, but no details on the origin and the means of identification was reported. The DNA sequence data derived from this strain were deposited with GenBank as acc. no AJ133375, and the authors reported similarities to *Agaricus blazei*. As *Agaricus sylvaticus* belongs to section Sanguinolenti, which is generally regarded by all taxonomists acquainted with the genus *Agaricus* as rather distantly related to sect. Arvenses and *Agaricus subrufescens* sensu strictu, the DNA sequence data published by Huang and Hseu are probably derived from a misidentified isolate that may actually correspond with *Agaricus subrufescens*, rather than *Agaricus sylvaticus*.

Even among the closest relatives of *Agaricus subrufescens*, i.e., the species accommodated in *Agaricus*, section Arvenses, some species have probably been confused with *Agaricus subrufescens* sensu Kerrigan (2005), before this author published his conclusive study involving DNA sequencing of type material. The taxonomic concept of *Agaricus subrufescens* had not been clear prior to the study by Kerrigan (2005). Geml J. et al. (Mycol Progress (2004) 3:157-176) have classified some isolates as *Agaricus subrufescens*, (e.g. the specimen with corresponding GenBank acc, no AY484674) which do apparently not correspond to the current species concept proposed by Kerrigan (2005). The fact that they also included *Agaricus blazei* in their study suggests that they employed a different species concept from that developed later by Kerrigan (2005), on which the present invention relies.

Liver X receptors (LXR) are nuclear hormone receptors that play a critical role in cholesterol homeostasis. LXR agonists are expected to increase cholesterol efflux, lower LDL (the "bad" cholesterol) and raise HDL (the "good" cholesterol) levels (see Zelcer N et al., Curr. Opin. Investig. Drugs. 2005 6(9): 934-943, and Geyeregger R et al., Cell. Mol. Life Sci. 2006 63(5): 524-539). Known LXR agonists were discovered by screening libraries from natural sources and proof of principle in animal models was possible (see Herath K B, et al., J. Nat. Prod. 2005 68: 1437-1440; Jayasuriya H et al., J. Nat. Prod. 2005 68: 1247-1252; and Singh S B et al., Bioorg. Med. Chem. Lett. 2005 15(11): 2824-2828). LXR agonists have also been shown to modulate (especially inhibit) immune and inflammatory responses, especially in macrophages (see e.g. Zelcer, N., et al., J. Clin. Invest. 116(3), 607-614 (2006)).

Two LXR genes have been identified, LXRα and LXRβ (also known as NR1H3 and NR1H2, respectively). The LXRβ is expressed ubiquitously, whereas the LXRα expression is mainly restricted to tissues known to play an important role in lipid metabolism (liver and adipocytes). In addition, human skeletal muscle cells have higher levels of LXRβ than LXRα (Kase et al., Diabetologia 50(1), 2171-2180 (2007).

The protein family of Liver X Receptors (LXRs) was originally identified as orphan (unknown ligand) members of the nuclear receptor superfamily. As other family members, LXRs hetero-dimerize with retinoid X receptor and bind to specific response elements (LXREs). Two protein variants, alpha (LXRA; NR1H3) and beta (LXRB; NR1H2), are known (Song et al., Ann. N.Y. Acad. Sci. 761: 38-49, 1995). LXR-alpha and LXR-beta regulate the metabolism of several important lipids, including cholesterol in bile acids. It was proposed that naturally occurring oxysterols are physiological ligands of LXRs triggering regulation of these pathways (Janowski et al., Proc Natl Acad Sci USA. 5; 96(1):266-71, 1999).

LXRs have in the arts been considered as established regulators of cholesterol, lipid and glucose homeostasis (Li and Glass, J. Lipid Res. 45, 2161-2173, 2004). Moreover LXRs are described in the arts as highly expressed in adipose tissues and to be involved in white/brown fat tissue differentiation (Hansen and Kristiansen Biochem J. (2006) 398(2): 153-68). In mature adipocytes, activation of LXR was described in the art as inducing expression of genes involved in lipid and glucose homoeostasis (Laffitte et al. Proc. Natl. Acad. Sci. U.S.A. (2001) 98: 507-512162; Laffitte et al. Proc. Natl. Acad. Sci. U.S.A. (2003) 100: 5419-5424163; Dalen et al. Biol. Chem. (2003) 278: 48283-48291; Ulven et al. J. Lipid Res. (2004) 45: 2052-2062).

LXRbeta has been described as regulator of Uncoupling Protein 1 (UCP1) expression. LXRα-/-/LXRβ-/- mice exhibited enhanced energy dissipation due to ectopic expression of UCP1 in WAT and muscle while administration of LXR agonist to mice suppresses UCP1 expression in BAT (Stulnig Mol. Pharmacol. (2002) 62: 1299-1305). UCP1 is involved in thermogenesis (thermoregulation) and enhanced energy expenditure.

LXRα-/-/LXRβ-/- mice were in the art found to be resistant to diet-induced obesity when fed a western high-fat high-cholesterol diet, but not when fed a cholesterol-free high-fat diet. In the art, LXR agonists have been described as potential therapeutic agents for treatment of dyslipidemia and thereby metabolic syndrome, coronary artery disease, and atherosclerosis due to their anti-atherogenic and HDL-raising properties (Lund et al. Arterioscler. Thromb. Vasc. Biol (2003) 23: 1169-1177; Beaven and Tontonoz Ann Rev Med. (2006) 57: 313-29; Baranowski J Physiol Pharmacol (2008) 59, Suppl7, 31-55; Sanal World J Gastroenterol. (2008) 14(6): 831-44). Moreover, it has been described in the arts that LXRs are involved in fatty liver disease (Sanal M G. 2008; Beaven and Tontonoz, 2006). Furthermore LXR ligands have been described in the arts as efficient in models of type 2 diabetes and have been claimed as useful insulin sensitizers for treatment of insulin resistance (Commerford et al. Mol Endocrin (2007) 21(12): 3002-301; Baranowski, 2008).

Synthetic oxysterol-mimetic drugs (LXR agonists) have also been described as novel therapeutics for management of Alzheimer's Disease and other neurological afflictions characterized by deranged tissue cholesterol homeostasis (Vaya and Schipper J Neurochem. (2007) 102 (6):1727-37). LXR modulators have been discussed as potential targets for pharmacological intervention in cardiovascular diseases and potential cardioprotectants (Cao et al. Drug News Perspect (2004) 17(1): 35-41; Schmitz and Drobnik Curr Opin Investig Drugs. (2002) 3(6): 853-8). LXR agonists have further been described as anti-inflammatory drug candidates (Joseph et al. Nat Med (2003) 9: 213-219) Moreover LXR receptor agonists are described in the arts as protecting against neuronal damage following global cerebral ischemia while providing neuroprotection in inflammatory cerebral conditions via inhibition of NfkappaB (Cheng et al. Neuroscience (2010) 14; 166(4):1101-9).

"Medicinal mushrooms" have traditionally been used as "herbal" remedies in Asian folk medicine for over 300 years, comprising a substantial part of the so-called Traditional Chinese Medicines (TCM), for their therapeutic effects in various disease areas. Our current knowledge on these fungi has been summarized in various reviews (Chang, Int J Med Mushrooms (2006), 8: 187-195; Lindequist et al., Medizinische Monatsschrift Pharmazeuten (2010), 33: 40-48; Wasser, Int J Med Mushrooms (2010) 12: 1-16). Many important fungal species that have been traditionally used in Asia as therapeutic agents (for example, *Cordyceps sinensis, Ganoderma lucidum, Trametes versicolor*) are not considered edible in the Western world, as their sporocarps have a rather tough, non-fleshy consistence. Nonetheless, they are being increasingly cultivated even in Europe and America for preparation of traditional "herbal" remedies, food supplements and ingredients for cosmetics. Mushroom powders, as well as aqueous and organic extracts made from these organisms are being sold world-wide with increasing commercial success. Other "medicinal mushrooms" like *Hericium erinaceus* and *Lentinula edodes*, are being grown at a very large scale and sold for culinary as well as for medicinal purposes. Interestingly, species of the genus *Agaricus*, which had been successfully cultivated as food for over a century in the Western world, do not belong to these traditional "herbal" medicines of Asian origin. However, researchers in Japan and other Asian countries have evaluated the medicinal properties of edible mushrooms from other parts of the world in the past decades, along with their own indigenous species. Accordingly, they also found beneficial effects in certain species from America and Europe. Some of them have meanwhile reached significant commercial value as "medicinal mushrooms" in Asia, despite they are not included in any ancient Pharmacopoeia. One such example is *Agaricus subrufescens*, which is still most often referred to in the scientific and trivial literature as "*Agaricus blazei*". According to the current knowledge, the strains that are currently being studied for medicinal properties are derived from material that had originated from Brazil, from where it was transferred to Asia by Japanese researchers and evaluated there during the last decades of the $20^{th}$ century for beneficial effects and chemical constituents.

Owing to their great economical importance, many species of the genus *Agaricus* have been targeted extensively for studies on their chemical constituents. In particular the fruiting bodies have been screened for the presence of toxins and metabolites of potential benefits. Far less information appears to be available on the secondary metabolites of *Agaricus* cultures. Stadler et al. (J. Antibiot. 58, 2005, 775-786) reported a series of triglycerides of chlorinated phenols with potential analgesic effects, owing to their strong inhibitory activity against neurolysin, from cultures of *Agaricus macrosporus* and several other species of the genus *Agaricus*. Aside from the triglycerides, which were named agaricoglycerides, simple chlorinated aromatics such as 3,5-dichloroanisic acid were also obtained. Neither the agaricoglycerides nor the other aromatic compounds were identified in the corresponding fruiting bodies from which the cultures producing agaricoglycerides had been made. On the other hand, under the chosen fermentation conditions, the dichloro anisic acids were prevalent in the cultures of several *Agaricus* strains, including such ones that did not produce agaricoglycerides. These results have shown that the secondary metabolism of *Agaricus* species in fruiting bodies versus mycelial cultures can be completely different.

Indeed, the characteristic secondary metabolites that are hitherto known from fruiting bodies of many *Agaricus* species include aromatic nitrogen containing quinones, hydrazone derivatives and related compounds (see overview by Gill and Steglich, 1987, Progress in the Chemistry of Natural Products, Vol. 51, Chapter 6, p. 236f.). The most important compound of the hydrazone type appears to be N2-(gamma-L-glutamyl)-4-hydroxymethyl-phenylhydrazine; trivial name: agaritine), which has been detected in substantial quantities even in many edible species of *Agaricus* (see review by Roupas et al., Journal of Functional Foods 2, 2010, 91-98). This compound is known to have toxic effects, as it is converted into carcinogenic metabolites in the mammalian body. Therefore, it has been discussed to be a potential hazard for the therapy of diseases in humans using fruiting bodies of *Agaricus* species as "medicinal mushrooms. Using the invalid species name "*Agaricus blazei*", Firenzuoli et al. (Evidence-based Complementary and Alternative Medicine (2008) 5(1): 3-15) have recently discussed this problem in *Agaricus subrufescens*, which also belongs to the species of *Agaricus* that contain agaritine in their basidiocarps.

They reasoned that the potential carcinogenic effects of agaritine are controversial to those of the beta glucanes that are also produced in the fruiting bodies of *Agaricus subrufescens* and have been made responsible for cancer prevention and manifold other beneficial biological activities. Most of the recent results have been summarized by Sorimachi & Koge (2008) Current Pharmaceutical Analysis, 4 (1), pp. 39-43.

According to this review and the references cited therein, the aqueous extract of the fungal sporocarps has been demonstrated both in vivo and in vitro to have: Antitumor, immunostimulating, anti-genotoxic, anti-mutagenic and anti-clastogenic and antiviral activity.

The cultured mycelia of the fungus also contain beta-glucane polysaccharides with similar beneficial activities and are being produced at large scale by fermentation of *Agaricus subrufescens* in Asia. Several working groups in Asia, such as Kawagoe et al. (*J Chem Eng Japan*, (2004) 37 (8 SPEC. ISS.): 1056-1061), Kim et al. (*J Microbiol & Biotechnol*, (2004) 14: 944-951), Lin and Yang (*J Microbiol, Immun and Infection*, (2006) 39: 98-108) have been studying the optimization of their production in submerged culture, which they proposed to be taken as substitute for the relatively expensive fruiting bodies. Accordingly, Lin and Yang (2006) measured the crude polysaccharide content of the mycelia during fermentation. Fan et al. (LWT—Food Sci Technol, (2007) 40: 30-35) even used biological assays in addition to other analytic methods to quantify the biologically active polysaccharides. Na et al. (*J Microbiol & Biotechnol*, (2005) 15: 1388-1391) have studied the growth and production of such macromolecules in submerged culture of *A. subrufescens*. They found that the addition of yeast extract along with glucose during fermentation of the fungus has a positive effect on cell growth and production of beta-glucanes and proposed a method for fed-batch fermentation of the fungus to optimize glucan production.

In general, all other published optimization experiments for *A. subrufescens* in submerged culture appear to have been directed towards the yields of mycelia, or beta-glucanes and other macromolecular, hydrophilic, biologically active agents contained therein.

In this context, it is important to note that the evidence provided by Mizuno et al. (*Biochem & Molecular Biology Int*, (1999) 47: 707-714) and Hashimoto et al. (*Int J Med Mushrooms*, (2006) 8: 329-341) strongly suggests that the polysaccharides produced in cultured mycelium of *A. subrufescens* are entirely different from the ones in the fruiting bodies. Accordingly, even those studies related to the beneficial properties of the fruiting body extract are not necessarily also valid for material extracted from the mycelia of *A. subrufescens*.

As will be demonstrated further below, the above described macromolecular highly hydrophilic substances are of no concern to the current invention. Nevertheless, they have raised great interest in pharmacological research on the so-called medicinal mushrooms and are clearly held responsible for most of the hitherto reported biological and pharmacological activities of *Agaricus subrufescens* and other fungal species that are here regarded as synonyms.

In addition to the macromolecular metabolites treated in the preceding paragraphs, *Agaricus subrufescens* also contains triterpenoid compounds that are also sometimes referred to in the literature as "steroids", although their chemical structures are different from those of the steroids that occur in humans. These compounds have physico-chemical and pharmacological properties quite different from those of the polysaccharides. For instance, they are almost insoluble in water, but can be readily extracted with organic solvents and thus be separated form the glucanes and other macromolecules, which will precipitate by addition of alcohol (either methanol or ethanol) to an aqueous solution, e.g. the culture filtrate as mentioned in WO 2006/133708. In addition, the triterpenoids have a rather low molecular weight in comparison to the macromolecules, and their chemical similarities to the human steroidal hormones and other steroids that occur in the human body make them more likely to exert a direct pharmacological effect, whereas the biological mode of action of the beta-glucanes and other macromolecules is believed to be due to indirect effects on the immune system, which does not necessarily involve their entering the human blood from the intestine (for overview see Chen & Seviour, *Mycological Research* (2007) 111: 635-652).

From fruiting bodies of *A. subrufescens*, Kawagishi et al. (*Phytochemistry* (1988) 27: 2777-2779) have reported several triterpenes with cytotoxic effects against the cancer cell line HeLaS3. Recently, Ito et al. (*Oncology Rep* (2008) 20: 1359-1361) identified another triterpenoid named blazein (again from *Agaricus subrufescens*, but using the invalid name "*A. blazei*"), which induced apoptosis in lung cancer cells. Such triterpenoids could also be responsible for certain other biological effects noted for the organic extracts of the fruiting bodies of *A. subrufescens*, such as those reported by Lund et al. (*Pharma Biol* (2009) 47: 910-915) who found antimicrobial activities in various extracts of the fungus (here referred to as *A. brasiliensis*), with the most potent activities in the 100% ethanol and weaker activities in extracts prepared by using more polar solvent mixtures. Bellini et al. (*Gen Mol Biol* (2008) 31: 122-127) used methanol for extraction of the mushrooms and found significant biological activities in these samples.

As the beta-glucanes are hardly soluble at all in such organic solvents and will inadvertently precipitate, they cannot be held responsible for the biological activities of non-aqueous extracts. On the other hand, Ziliotto et al. (*Nut Cancer* (2009) 61: 245-250) studied aqueous and various organic extracts of the same mushroom, but failed to detect any significant anticancer activities in a broad panel of malignant cell lines up to concentrations of 250 mg/ml.

Notably, the triterpene compounds from basidiocarps (i.e., fruiting bodies) of *A. subrufescens* all possess a regular tetracyclic triterpene carbon skeleton without any spiro-ring formation, similar to the ergostane and lanostane derivatives that are present in many other basidiomycetes (Zjawiony (*J. Nat. Prod.*, 2004, 67(2): 300-310).

By contrast, rather characteristic and apparently specific triterpenoids have been isolated repeatedly from the cultured mycelium of *A. subrufescens* by Asian microbiologists and natural product chemists. Various papers have been published on this subject, for instance by Hirotani et al. (*Tetrahedron Lett* (1999) 40: 329-332); Hayashi et al., (*Phytochemistry* (2002) 59: 571-577; *Tetrahedron Lett* (2000) 41: 5107-5110; *Phytochemistry* (2002) 61: 589-595; *Tetrahedron Lett* (2003) 44(43): 7975-7979; *Tetrahedron* (2005) 61(1): 189-194). The biosynthesis of the blazeispirols was also studied by Hirotani et al. (*Tetrahedron Lett* (2000) 41: 6101-6104; *Tetrahedron Lett* (2001) 42: 5261-5264; *Tetrahedron* (2002) 58: 10251-10257) and is believed to arise from the ubiquitous fungal metabolite, ergosterol. The trivial names (blazeispirane and protoblazeispirane) were proposed for the two unprecedented des-A-ergostane-type carbon skeletons of the blazeispirols that have so far not been found in any other organism but the fungus that is here regarded as *Agaricus subrufescens*. (Notably, the blazeispirols have so far only been obtained from the cultured mycelia of this species in submersed culture). Biological activities of these compounds are widely unknown. Only Hirotani et al. (Tetrahedron Lett., (2003) 44(43): 7975-7979) reported that two derivatives of this type showed a moderate circumvention of drug resistance on mouse leukaemia P388/VCR cells. Some studies performed previously on biological activities of the extracts prepared from cultures of *A. subrufescens* and its synonyms might relate to the presence of blazeispirols. However, in these studies, the major active principles have not been identified conclusively, or there is even some evidence that not the genuine metabolites produced by the fungus but rather the plant-derived media constituents caused the observed biological effects of the hot water extract studied. For instance, Oh et al. (*J Agric Food Chem* (2010) 58: 4113-4119) have reported on hypoglycaemic activities in vivo of "semipurified" fractions from a hot water extract prepared from submerged cultures of *A. subrufescens* (again as "*A. blazei* Murill"), but the authors themselves suspected that isoflavonoids from the culture medium, rather than fungal metabolites, were the bioactive agents, because such metabolites were detected in the active fraction. The employed procedure for preparation of the active fraction, involving first extraction with hot water, followed by subsequent extraction of the resulting hot water extract with different solvents, is certainly not a feasible method for enrichment of blazeispirols and metabolites of similar polarity.

Since the addition of soybean also led to enhanced antihepatoma activities in the study by Su et al. (*J Agric Food Chem* (2008), 56(20): 9447-9454), and this plant is widely known to contain large amounts of isoflavonoids, it remains to be evaluated how such compounds would contribute to the biological effects observed in extracts from cultures of *A. subrufescens*, even though Su et al. (*J Agric Food Chem* (2008), 56(20): 9447-9454) used chromatography to isolate and identify blazeispirols A and C and confirmed the biological activities of these compounds against liver cancer cell lines.

Other studies such as that by Yoon et al. (*J Clin Biochem Nut* (2008) 43; 118-125) on antioxidative and antimutagenic effects also dealt with organic extracts from cultured mycelia of *A. subrufescens*, and therefore the observed activity might eventually be correlated to the presence of blazeispirols, rather than to the action of the water-soluble beta glucans.

Medimush (GlycoNova) filed patent applications all claiming the priority of DK 2005 0000881, US 2005 0690477P, DK 2006 0000115, and US 2006 0761745; the inventors worked with aqueous extracts of cultures of the genus *Agaricus*. In further dependent claims the applicant refers to *A. blazei*. It is futile to clarify the assignment of the strain because the examples clearly outline that the inventors always used water soluble compounds as they used methanol to precipitate the active compounds from the culture broth. No example presents results of organic extracts comparable those mentioned in the present invention. The disclosed culturing times are 7 days (*Trametes versicolor*) and 3 days (*Schizophyllum commune*); where the inventors explicitly point to the production of polysaccharides. The PCT applications identify bioactive agents by their biological activity and not by their chemical identity. The subsequent applications therefore are specified to the use of polysaccharides.

The disclosed procedures are not appropriate to isolate the compounds of the present invention.

Some other applications claim for a weight reducing effect using combinations of different products of plant or mushroom origin which might contain *A. subrufescens*:

Primavera (PCT/US2004/012811 & U.S. Ser. No. 10/831,353; and the divisional appl. U.S. Ser. No. 12/240,236) claim for the use of mushrooms such as *A. subrufescens* as "liver protecting agent" or as "hunger suppressing" agent. The term mushroom is not further explained according the part of the organisms used. Consequently the common definition for "mushroom" as being a fruit body must be presumed.

Goino (Nagano, Japan, EP1736206, US20070178118) claims for a combination of a plant (Araliaceae) and an extract component which might be of the genus *Agaricus*, specified to *A. blazei*, further specified to a "hot water extract", still more specified to an extract "containing useful saccharides such as Beta-glucan" for the use as anti-tumor agent which further exhibits several activities like hypotensive action, total cholesterol-lowering action in blood and neutral fat-lowering action, therefore might be useful as anti-hyperlipidemic agent.

There remains a need for new safe and effective compositions for treating, prophylactically and/or therapeutically, diseases, disorders or conditions that respond to LXR modulation. The problem to be solved by the present invention is therefore to find compositions or compounds useful for this purpose.

BRIEF SUMMARY OF THE INVENTION

The invention relates to the use, or methods (especially with regard to animals, especially human, that are in need of such treatment) comprising the use, respectively, of an extract and/or especially one or more natural spiro triterpenoids and derivatives thereof, especially from the blazeispirol family, obtainable from *Agaricus* species, alone or as supplement, as active ingredient in the prophylactic and/or therapeutic treatment of a disease, disorder or condition that responds to the modulation of Liver X receptor, either in humans or in other mammals, and/or to the use of said extract and/or natural compound(s) or mixtures for the treatment of said disease, disorder or condition, as well as corresponding methods of treatment, or their use in the manufacture of a pharmaceutical or nutraceutical formulation for said treatment. The invention relates also to said extract and/or compound(s) for use in the treatment or in the preparation of a medicament (including a nutraceutical) for the prophylactic and/or therapeutic treatment of said disorder, disorder or condition, as well as their preparation. It also relates to pharmaceutical or nutraceutical formulations comprising said extract and/or natural compound(s) which are useful in said prophylactic and/or therapeutic treatment.

They can also be used for non-therapeutic, e.g. cosmetic, purposes only. Other invention embodiments are described below.

GENERAL DESCRIPTION OF THE INVENTION

Surprisingly, it has now been found that a certain class of compounds, namely spiro triterpenoids and derivatives thereof, that can be obtained from liquid (especially mycelial) cultures of Agaricus species, have the property to modulate, especially inhibit, LXR. They are thus useful in the treatment of diseases, disorders or conditions that respond to LXR modulation.

More specifically, the invention is based on prophylactically and/or therapeutically useful secondary metabolites, which can be obtained from (especially mycelial) cultures of particular species of fungi of the economically important genus Agaricus, which have been treated in the literature under various names, according to different taxonomic concepts. In fact, not all of the species of Agaricus, but only a particular group of Agaricus species, treated previously in the literature, are subject of the present invention, owing to the surprising discovery that cultures of many other Agaricus species, albeit phylogenetically related, do not overproduce the compounds that are subject of this invention under the conditions described in the Examples.

Details regarding the genus Agaricus can be found above and especially below, where the species concept under which the appropriate fungi can be defined is illustrated.

Figure 1:
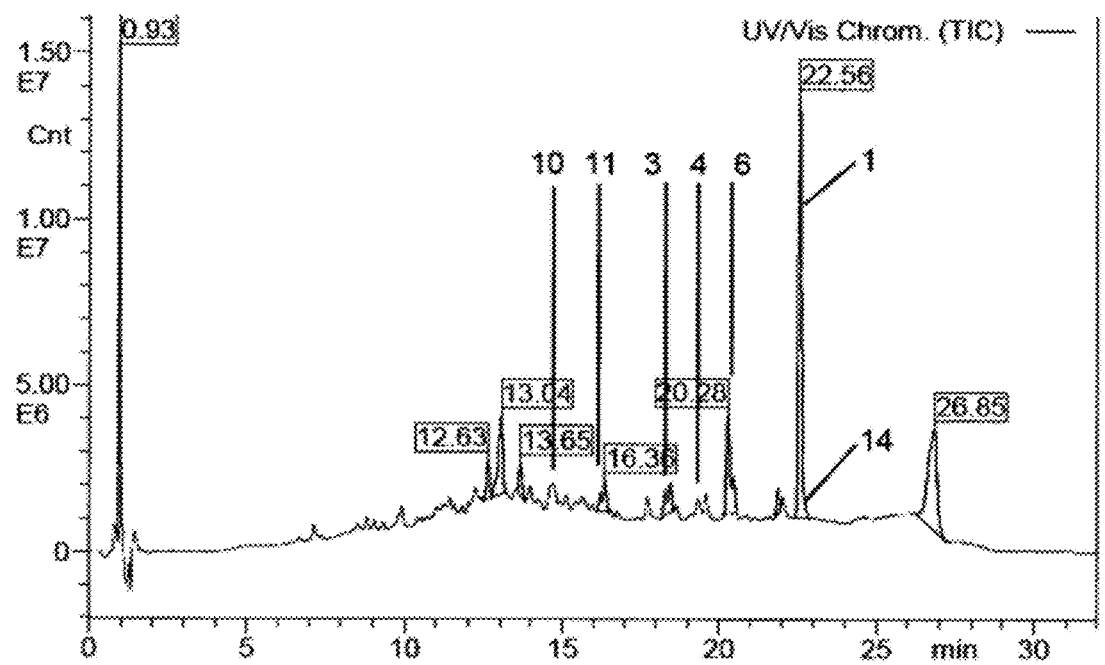
FIG. 1: Typical analytical HPLC chromatogram of a product of example 1b, assigned signals refer to Table 1

"In group" refers to strains showing production of the compounds of the formula I, "out group" to strains not showing such production.

DETAILED DESCRIPTION OF THE INVENTION

In a first embodiment, the invention relates to a compound of the formula I, or an extract comprising a compound of the formula I,

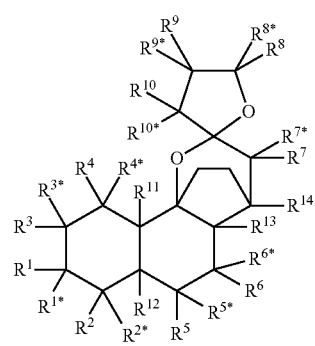

(I)

wherein
each of $R^1$, $R^{1*}$, $R^2$, $R^{2*}$, $R^3$, $R^{3*}$, $R^4$, $R^{4*}$, $R^5$, $R^{5*}$, $R^6$, $R^{6*}$, $R^7$, $R^{7*}$, $R^8$, $R^{8*}$, $R^9$, $R^{9*}$, $R^{10}$, $R^{10*}$, $R^{11}$, $R^{12}$, $R^{13}$ and $R^{14}$ is hydrogen, unsubstituted or substituted $C_{1-7}$alkyl, hydroxyl, halo, unsubstituted or substituted $C_{1-7}$alkoxy, $C_{2-7}$alkenyl, $C_{2-7}$alkynyl, unsubstituted or substituted $C_{2-7}$alkanoyloxy, amino, NHR or NRR', wherein R and R' are, independently of each other, selected from the group consisting of $C_{1-7}$alkyl, substituted $C_{1-7}$alkyl, unsubstituted or substituted $C_{6-14}$aryl, unsubstituted or substituted $C_{3-12}$cycloalkyl, unsubstituted or substituted $C_{2-7}$alkanoyl, unsubstituted or substituted $C_{1-7}$alkanesulfonyl, unsubstituted or substituted arylsulfonyl, unsubstituted or substituted $C_{3-12}$cycloalkyl-CO or $C_{6-14}$aryl-CO—, with the proviso that not more than one of R and R' can be unsubstituted or substituted $C_{2-7}$alkanoyl, unsubstituted or substituted $C_{3-12}$cycloalkyl-CO— or $C_{6-14}$aryl-CO—, the other can be as just defined;

and wherein the substituents for substituted $C_{1-7}$alkyl, substituted $C_{1-7}$alkoxy, substituted $C_{1-2}$alkanoyloxy, substituted $C_{6-14}$aryl, substituted $C_{3-12}$cycloalkyl, unsubstituted or substituted $C_{1-7}$alkanesulfonyl, unsubstituted or substituted arylsulfonyl, substituted $C_{3-12}$cycloalkyl-CO— and $C_{6-14}$aryl-CO— can be one or more substituents independently selected from the group consisting of hydroxyl, $C_{1-7}$alkoxy, $C_{2-7}$alkanoyloxy, $C_{3-12}$cycloalkyl, $C_{6-14}$aryl, halo, =O, =S, =NH or =NR" wherein R" is $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO or $C_{6-14}$aryl-CO—;

or each one or more of the pairs of geminal symbols $R^1$ and $R^{1*}$; $R^2$ and $R^{2*}$; $R^3$ and $R^{3*}$; $R^4$ and $R^{4*}$; $R^5$ and $R^{5*}$; $R^6$ and $R^{6*}$; $R^9$ and $R^{9*}$; and $R^{10}$ and $R^{10*}$ together can form =O, =S, =NH or =NR''' wherein R''' is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO or $C_{6-14}$aryl-CO—; with the proviso, that if other double bonds are present, they are either isolated or conjugated from the binding double bonds for =O, =S, =NH or =NR''';

or each of one or more pairs of vicinal symbols $R^{1*}$, $R^{2*}$, $R^{3*}$, $R^{4*}$, $R^{5*}$, $R^{6*}$, $R^{11}$ and $R^{12}$ can, together with the bond of the ring atoms to which they are bound, form a double bond, where if more than one double bond is present in the compound of the formula I, the double bonds are conjugated double bonds (double bonds separated by a single bond) or isolated double bonds (double bonds separated by two or more single bonds), or both types are present;

or $R^1$ and $R^2$, together with the ring atoms to which they are attached, form a 4- to 8-membered unsaturated or partially saturated or saturated carbocyclic ring, with the proviso that that if $R^1$ is part of a double bond in the ring, then $R^{1*}$ also is part of that double bond and if $R^2$ is part of a double bond in the ring, then $R^{2*}$ is also part of that double bond, in which case said double bond or double bonds are not formed by $R^{1*}$ and $R^{2*}$;

or $R^1$ and $R^3$, together with the ring atoms to which they are attached, form a 4- to 8-membered unsaturated or partially saturated or saturated carbocyclic ring, with the proviso that if $R^1$ is part of a double bond in the ring, then $R^{1*}$ also is part of that double bond and if $R^3$ is part of a double bond in the ring, then $R^{3*}$ is also part of that double bond, in which case said double bond or double bonds are not formed by $R^{1*}$ and $R^{3*}$;

where the carbocyclic rings in all cases can be unsubstituted or substituted by one or more moieties independently selected from the group consisting of hydroxyl, $C_{1-7}$alkyl, $C_{1-7}$alkoxy, $C_{2-7}$alkanoyloxy, $C_{3-12}$cycloalkyl, $C_{6-14}$aryl, halo, =O, =S, =NH or =NR" wherein R" is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO and $C_{6-14}$aryl-CO—;
or each one or more pairs of symbols
or any possible combinations of the meanings for the substituents as mentioned above;
or a pharmaceutically acceptable salt, hydrate or other solvate thereof, for USE as defined below;
e.g. for use in the prophylactic and/or therapeutic treatment of a disease, disorder or condition that responds to the modulation of Liver X receptor in a mammal;
or for use as active ingredient in a pharmaceutical, including nutraceutical, formulation for the prophylactic or therapeutic treatment of said disease, disorder or condition.

In a second embodiment, the invention relates to a new triterpenoid derivative or an extract comprising it, where the triterpenoid derivative is selected from the group consisting of those represented by Compounds No. 5, 6, 7, 8, 9, 10, 11, 12 and 13 of Table 1 given below.

In a third embodiment, the invention relates to a pharmaceutical or nutraceutical formulation, comprising a compound of the formula I as defined above or below, or a pharmaceutically (including nutraceutically) acceptable salt, and/or solvate (including hydrate) thereof.

In a fourth embodiment, the invention relates to the use of a compound of the formula I or an extract comprising it, or a pharmaceutically acceptable salt and/or solvate (including hydrate) thereof, respectively, in the prophylactic and/or therapeutic treatment of a disease, disorder or condition that responds to LXR modulation.

In a fifth embodiment, the invention relates to the use of a compound of the formula I or an extract comprising it, or a pharmaceutically acceptable salt and/or solvate (including hydrate) thereof, respectively, in the preparation of a pharmaceutical (including nutraceutical) formulation for use in the prophylactic and/or therapeutic treatment of a disease, disorder or condition that responds to LXR modulation, as well as a method for preparing such a formulation.

In a sixth embodiment, the invention relates to a pharmaceutical and/or nutraceutical formulation useful in the therapeutic treatment of a disease, disorder or condition that responds to LXR modulation.

In addition, also non-therapeutic use is possible, e.g. the USE of a compound of the formula I, or a mixture of two or more such compounds, for the cosmetic treatment of a warm-blooded animal, especially a human, comprising administering said compound or compound mixture to said animal, especially a human, in order to achieve cosmetically advantageous results; where the compound(s) can also be used in the form of a cosmetically acceptable (corresponding especially to pharmaceutically and/or nutraceutically acceptable as defined below) salt, and/or in the form of solvates.

Specific embodiments of the invention are also represented by the claims which are incorporated here by reference, especially the dependent claims.

The general expressions, within the present disclosure, preferably have the following meaning, where in each embodiment one, more than one or all more general expressions may, independently of each other, be replaced with the more specific definitions, thus forming preferred embodiments of the invention, respectively:

Preferably, the compounds of the formula I are natural compounds, that is, compounds that are present in and can be isolated or extracted from natural sources (especially those mentioned in detail above and below) without chemical synthesis steps (though they may also be prepared or modified by chemical synthesis, e.g. acylated or the like) and are thus present as extracts or purified components of extracts, and not derivatives only obtainable by chemical synthesis.

They can also be part of an extract which is obtainable by extracting a plant or a plant part from an appropriate mushroom, especially in culture, of the genus *Agaricus*.

Further, the present triterpenes and triterpene derivatives of the formula I comprise all stereoisomers, such as those which may exist due to asymmetric carbons on the various substituents, including enantiomeric forms and diastereomeric forms. Individual stereoisomers of the triterpenoids and triterpenoid derivatives of the present invention may, for example, be substantially free of other isomers, or may be admixed, for example, as racemates or with all other, more than one other or other selected stereoisomers.

To the extent that compounds the formula I and salts thereof may exist in their tautomeric form, all such tautomeric forms are contemplated herein as part of the present invention embodiments.

Where salt-forming groups (e.g. acidic groups, such as phenolic OH groups, or basic groups, such as amino or imino groups) are present within them, the triterpenoids and their derivatives of the formula I may be in the free form or in the form of salts. The term "salt(s)", as employed herein, denotes acidic and/or basic salts formed with inorganic and/or organic acids and bases. In addition, when a compound of the formula I contains both a basic moiety and an acidic moiety, "inner salts" may be formed and are included within the term "salt(s)" as used herein. Pharmaceutically (or nutraceutically) acceptable (i.e., non-toxic, physiologically acceptable) salts are preferred, although other salts are also useful, e.g., in isolation or purification steps which may be employed during preparation. Salts of compounds of the formula I may be formed, for example, by reacting a compound of the formula I with an amount of acid or base, such as an equivalent amount, in a medium such as one in which the salt precipitates or in an aqueous medium followed by lyophilization. Salts of the compounds of the formula I may also be formed by reacting a compound of the formula I with an alkylating agent, for example, by quaternization of an amine, where natural compounds are preferred. Also ion exchangers can be used to form salts from free forms or free forms from salts of a compound of the formula I.

Compounds of the formula I which contain a basic moiety may form salts with a variety of organic and inorganic acids. Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerolphosphates, hemisulfates, heptanoates, hexanoates, hydrochlorides, hydrobromides, hydro-iodides, 2 hydroxyethanesul-fonates, lactates, maleates, methanesulfonates, 2-naphtalene-sulfonates, nicotinates, nitrates, oxalates, pectinates, per-sulfates, 3-phenylpropionates, phosphates, picrates, pivalates, propionates, salicylates, succinates, sulfates, sulfonates, tartrates, thiocyanates, toluenesulfonates, such as tosylates, undecanoates, and the like.

The compounds of the formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, N-methyl-D-glucamines, N-methyl-D-glucamides, t-butyl amines, and salts with amino acids such as arginine, lysine and the like. Also salts with salt-forming pharmaceutical and/or nutraceutical carrier materials are possible and encompassed by the invention.

Further, the compounds of the formula I or salts thereof may be in the form of their solvates, such as hydrates.

"Substantially" means preferably that the corresponding impurities are present only in trace amounts, e.g. in less than 5% by weight, less than 4% by weight, less than 3% by weight, less than 2% by weight, less than 1% by weight, less than 0.5% by weight or less than 0.2% by weight, in relation to the complete weight of the corresponding dry extract or compound of the formula I or mixture of compounds of the formula I.

Within the present disclosure, the term "compound(s) of the formula I" is often used instead of "(spiro) triterpenoid and/or triterpenoid derivative(s)".

"(Spiro) triterpenoid" can be replaced with "terpenoid spiro ketal compound" as well.

"A compound of the formula I" or "compound(s) of the formula I" can also refer to one or more compounds of the formula I, that is one compound or a mixture of compounds of the formula I, or to the USE of a compound of the formula I, where reference to compound(s) of the formula I always includes the compound(s) as such or in the form of a salt (especially a pharmaceutically acceptable salt), a solvate and/or a tautomer thereof. In all cases this means that either only one compound (in substantially pure form or as a direct extract or a further enriched extract) or a mixture of two or more compounds of the formula I (which mixture is preferred) can be present, e.g. in an extract or pharmaceutical/nutraceutical formulation according to the invention, or that it or they can be of USE according to the invention.

Preferably, the total weight share of the compound or all compounds of the formula I in an extract or mixture of compounds of the formula I or a purified compound of the formula I that is of USE according to the invention in the final extract, mixture or compound (direct or further enriched) is in the range from 0.01 to 100% by weight, more preferably from 1 to 100 or to 99% by weight, in another embodiment from 5 to 100 or to 99% by weight, or from 20 to 100 or to 95% by weight, or e.g. from 50 to 100 or to 90% by weight.

Where relative amounts of components are given in %, this means weight %, if not indicated otherwise.

"Obtainable" means that a product (e.g. extract or compound) may be obtained by the specified or other methods, or preferably it is obtained by the specified method.

As used herein, the term "therapeutical treatment" or "therapeutically effective amount" means the kind or amount of the active compound(s) of the formula I in the composition that will elicit the biological or medical response in a tissue, system, subject, or human that is being sought e.g. by the researcher, veterinarian, medical doctor or other clinician, which includes alleviation of the symptoms of the disorder, disease or condition being treated up to and including complete cure. The novel methods of treatment of this invention are for disorders known to those skilled in the art.

As used herein, the term "prophylactic treatment" or "prophylactically effective amount" means the kind or amount of the active compound(s) of the formula I in the composition that will elicit the biological or medical response in a tissue, system, subject, or human that is being sought e.g. by the researcher, veterinarian, medical doctor or other clinician, to prevent the onset of a disorder, disease or condition in subjects at risk for a disorder, disease or condition as mentioned herein.

Where solely "treatment" is used, this refers to prophylactic and/or therapeutic treatment, or any one thereof.

For testing, it is possible to conduct clinical trials (or animal assays as described in the Examples). e.g. clinical trials with humans (or other animals) analogous to those described in WO 2004/096252 or WO 2004/082700 (which are incorporated here by reference, especially with regard to the description of the tests on animals or especially humans), but only using one or more compounds of the formula I as described for the present invention.

The extracts or compounds according to the invention may be used as such, in the form or pharmaceutical or nutraceutical formulations (the latter term including food additives=supplements) or in the form of functional food.

Where the compounds or mixture of compounds of the formula I are used as supplement, this means that the compound(s), extracts or a pharmaceutical or nutraceutical formulation comprising them, each according to the invention, can be added to any other nutrient or pharmaceutical or nutraceutical. Thus they can especially serve as food supplement. However, the compound(s) or formulations may also be administered as such.

The activity against obesity can, for example, be tested as described in the Examples, especially in the in vivo experiments e.g. with rats described there.

"Nutraceuticals", "Functional Food", or "Functional Food products" (sometimes also called "Foodsceuticals", "Medicinal Food" or "Designer Food") for USE according to the present invention are defined as food products (including beverages) suitable for human consumption—the expression comprises any fresh or processed food having a health-promoting and/or disease-preventing property beyond the basic nutritional function of supplying nutrients, including food made from functional food ingredients or fortified with health-promoting additives, especially with effects in the prophylaxis or treatment of a disease, disorder or condition that responds to LXR modulation, and in which a compound or an extract comprising such compound(s) or a compound mixture of compounds of formula I, respectively, according to the invention is used as an ingredient (especially additive) as health benefit agent, especially in an effective amount.

"Comprising" or "including" or "having" wherever used herein is meant not to be limiting to any elements stated subsequently to such term but rather to encompass one or more further elements not specifically mentioned with or without functional importance, that is, the listed steps, elements or options need not be exhaustive. In contrast, "containing" would be used where the elements are limited to those specifically after "containing".

Where "about" is used or a specific numerical value is given without explicitly mentioning "about", this preferably means that a given value may deviate to a certain extent from the value given, e.g. in one of the invention embodiments by ±20% of the given numerical value, in another embodiment by ±10%. Also where "about" is not mentioned, this is implicitly to be considered present, in other invention embodiments as absent.

By the term a "disease, disorder or condition that responds to LXR modulation" and the like, preferably a disease is meant that is, in the sense of an amelioration for the animal or human treated, affected by an inhibition (antagonism) or preferably an activation (agonism) of the activity of LXR, e.g. LXRα or LXRβ or both. Among such diseases, disorders or conditions, the following are to be mentioned especially: A disease, disorder or condition selected from the group consisting of Syndrome X (also named Metabolic Syndrome), fatty liver disease, elevated cholesterol levels, lack of cholesterol homeostasis, hypercholesterolemia, elevated HDL/LDL ratio, HDL level elevation in blood, inadequate lipid homeostasis, e.g. dyslipidemia, lack of adipocyte differentiation, obesity, hypertension, cardiovascular disorders, such as coronary artery disorders, atherosclerosis or atheromateous lesions, heart overstraining, diabetes, especially type II diabetes, insulin desensitation or resistance, lack of glucose homeostasis, Alzheimer's disease, CNS inflammation, CNS ischemia or other inflammation, e.g. arthritis, bile acid related disorders.

In the case of prophylactic use, in addition vasoprotection, better thermoregulation, regulation of metabolic rate, homeostasis of bile acids, management of body weight or neuroprotection may be mentioned.

Lipid metabolism and/or body weight related disorders: fatty liver disease, elevated cholesterol levels, lack of cholesterol homeostasis, hypercholesterolemia, elevated HDL/LDL ratio, HDL level elevation in blood, inadequate lipid homeostasis, e.g. dyslipidemia, lack of adipocyte differentiation, obesity or adiposity are especially preferred for USE according to the invention, as are bile acid related disorders.

Further, cardiovascular related disorders: hypertension, cardiovascular disorders, such as coronary artery disorders, atherosclerosis or atheromateous lesions, heart overstraining are also especially preferred.

Also sugar metabolism related disorders, such as diabetes, especially type II diabetes, insulin desensitation or resistance, lack of glucose homeostasis, may, in an embodiment of the invention, be among the diseases that respond to LXR modulation.

Also CNS related disorders: Alzheimer's disease, CNS inflammation, CNS ischemia and inflammation related disorders: arthritis may be considered or omitted for treatment according to the invention.

Syndrome X, also named as Metabolic Syndrome, was first described by Reavan and often called Reavan-Syndrom (Reavan G M, *Diabetes* (1998) 37: 1595), and is defined by various organizations: International Diabetes Federation (IDF) (IDF Communications, Belgium, "The IDF consensus worldwide definition of the METABOLIC SYNDROME"; see http://www.idf.org/webdata/docs/IDF_Meta_def_final.pdf), World Health Organization (WHO) (Khalib O M N, *EMRO Technical Publications Series* (2006) ISBN 978-92-9021-404-5, p 22), European Group for the Study of Insulin Restistance (EGIR) (Bär; *Diabetes, Stoffwechsel and Herz* (2007) δ: 329-334), US National Cholesterol Education Program (NCEP) (*Circulation* (2002) 106: 3143-3421) and by the American Heart Association (Grundy et al., *Circulation* (2004) 109: 433-438; (2005) 112: e285-e290) which are referring to risk parameters which are defined by different critical values.

Within the scope of the present invention preferably at least three of the defined risk parameters (also called "symptoms") can be reduced.

Although the patient may not notice any symptoms from metabolic syndrome, the attending physician could identify the following as signs of the condition: (1) elevated insulin levels, due to insulin resistance; (2) type II diabetes; (3) central obesity (a disproportionate amount of body fat in the abdominal region); (4) hyperlipidemia (high levels of fats (lipids) in the blood, which include LDL ("bad") cholesterol and triglycerides. In addition, the size of the LDLs may be smaller than usual, which is more likely to promote atherosclerosis); (5) low level of HDL ("good") cholesterol; (6) hypertension (high blood pressure); (7) elevated levels of blood factors that promote blood clotting, such as plasminogen activator inhibitor-1 {PAI-I) and fibrinogen; (8) hyperuricemia (high levels of uric acid in the blood); and (9) microalbuminuria (small amounts of the protein albumin, found on urine tests) (Grundy S. M., *Am. J. Cardiol.* 83: 25F29F, 1999).

Especially preferred is a disease, disorder or condition selected from the group consisting of: Syndrome X, hypercholesterolemia, low HDL levels, hypertension, lack of lipid homeostasis, inappropriate adipocyte differentiation, obesity, cardiovascular disorders, including coronary artery disorders, Diabetes type 2, fatty liver disease, dyslipidemia and bile acid related disorders. Very preferred is a disease selected from obesity and lack of lipid homeostasis, hypercholesterolemia and low HDL levels (also as specific symptoms of Syndrome X).

While "obesity" is generally defined as a body mass index (BMI) over 30, for purposes of this disclosure, any subject, including those with a BMI of less than 30, who needs or wishes to reduce body weight or prevent body weight gain is included in the scope of "obese." Thus, subjects with a BMI of less than 30 and 25 and above (considered overweight) or below 25 are also included in the subjects of the invention. Morbid obesity refers to a BMI of 40 or greater.

By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to loose weight.

As used herein, "lean mass" or "lean body mass" (LBM) refers to muscle and bone. LBM does not necessarily indicate fat free mass. LBM comprises a small percentage of fat (roughly 3%) within the central nervous system (brain and spinal cord), marrow of bones, and internal organs. LBM is measured in terms of density. Methods of measuring fat mass and lean mass include, but are not limited to, underwater weighing, air displacement plethysmograph, x-ray, DEXA scans, MRIs and CT scans. In certain embodiments, fat mass and lean mass is measured using underwater weighing as known in the art.

By "fat distribution" is meant the location of fat deposits in the body. Such locations of fat deposition include, for example, subcutaneous, visceral and ectopic fat depots.

"Subcutaneous fat" refers to the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886, the entirety of which is incorporated herein by reference.

"Visceral fat" refers to the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases.

"Ectopic fat storage" means lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body.

The functional food products or pharmaceutical products according to the invention may be manufactured according to any suitable process, preferably comprising extraction of one or more compounds of the formula I and admixing to a functional food product or at least one nutraceutically or pharmaceutically acceptable carrier.

A functional food or a pharmaceutical or nutraceutical formulation comprising a compound, more preferably a compound mixture, for USE according to the present invention, can, for example, be obtained by
(a) extraction of one or more compounds and/or mixture of compounds of the formula I from a liquid (especially mycelial) culture of one or more mushrooms of the genera mentioned above by means of a lipophilic (preferably non-aqueous) solvent or solvent mixture; and
(b) mixing the resulting extract comprising one or more compounds and/or mixtures of compounds of the formula I as active ingredient in the preparation of the functional food product with the other constituents thereof or in order to obtain a pharmaceutical or nutraceutical formulation with one or more carrier materials or with a solvent or dispersant (allowing to form a suspension or emulsion).

Further processing steps may precede and/or follow, such as drying (e.g. freeze-drying, spray-drying, fluid bed or spouted bed or evaporation), granulation, agglomeration, concentrating (e.g. to syrups, formed via concentration and/or with the aid of thickeners), pasteurizing, sterilizing, freezing, dissolving, dispersing, filtering, centrifuging, confectioning, and the like.

When one or more compounds and/or a compound mixture according to the invention are added to a food product or pharmaceutical or nutraceutical, this also results in a functional food product or pharmaceutical or nutraceutical formulation according to the invention.

Preferably, a functional food product (nutraceutical) according to the invention (which is different from the corresponding fungus itself) comprises 0.001 to 30, e.g. 0.002 to 20, such as preferably 0.01 to 5, weight-% of a compound or mixture of compounds of the formula I according to the invention, the rest being food and/or nutraceutically acceptable carriers and optionally customary additives.

Further additives may be included, such as vitamins, minerals, e.g. in the form of mineral salts, unsaturated fatty acids or oils or fats comprising them, other extracts, or the like.

The functional food products according to the invention may be of any food type. They may comprise one or more common food ingredients in addition to the food product, such as flavours, fragrances, sugars, fruit, minerals, vitamins, stabilizers, thickeners, dietary fibers, protein, amino acids or the like in appropriate amounts, or mixtures of two or more thereof, in accordance with the desired type of food product.

Examples of basic food products and thus of functional food products according to the invention are fruit or juice products, such as orange and grapefruit, tropical fruits, banana, apple, peach, blackberry, cranberry, plum, prune, apricot, cherry, peer, strawberry, marionberry, black currant, red currant, tomato, vegetable, e.g. carrot, or blueberry juice, soy-based beverages, or concentrates thereof, respectively; lemonades; extracts, e.g. coffee, tea, green tea; dairy type products, such as milk, dairy spreads, quark, cheese, cream cheese, custards, puddings, mousses, milk type drinks and yoghurt; frozen confectionary products, such as ice-cream, frozen yoghurt, sorbet, ice milk, frozen custard, water-ices, granitas and frozen fruit purees; baked goods, such as bread, cakes, biscuits, cookies or crackers; spreads, e.g. margarine, butter, peanut butter honey; snacks, e.g. chocolate bars, muesli bars; pasta products or other cereal products, such as muesli; ready-to-serve-dishes; frozen food; tinned food; syrups; oils, such as salad oil; sauces, such as salad dressings, mayonnaise; fillings; dips; chewing gums; sherbet; spices; cooking salt; instant drink powders, such as instant coffee, instant tee or instant cocoa powder; instant powders e.g. for pudding or other desserts; meat fish or fish or meat products, such as sausages, burgers, meat loafs, meatballs, meat extracts, canned or tinned fish or meat, meat vol-au-vent, meat or fish soup, meat or fish skewers, fish fingers; or the like.

One or more other customary additives may be present, such as flavour, fragrances or other additives, such as one or more selected from stabilizers, e.g. thickeners; colouring agents, such as edible pigments or food dyes; bulking agents, such as fruit pulp, e.g. in dried form; polyols, such as xylitol, mannitol, maltitol or the like; preservatives, such as sodium or potassium benzoate, sodium or calcium carbonate or other food grade preservatives; antioxidants, such as ascorbic acid, carotionoids, tocopherols or polyphenols; mono-, oligo- or polysaccharides, such as glucose, fructose, sucrose, soy-oligosaccharides, xylo-oligosaccharides, galacto-oligosacharides; other artificial or natural non- or low-caloric sweeteners, such as aspartame or acesulfame; bitterness blockers; acidifiers in the form of edible acids, such as citric acids, acetic acid, lactic acid, adipic acid; flavours, e.g. artificial or natural (e.g. botanical flavours); emulsifiers; thiols, e.g. allylic thiols; diluents, e.g. maltodextrose; wetting agents, e.g. glycerol; stabilizers; coatings; isotonic agents; absorption promoting or delaying agents; and/or the like.

The one or more compounds of the formula I or compound mixtures thereof according to the invention can also be comprised in confectioned formulations to be added to foods including beverages, e.g. in the form of powders or granules, e.g. freeze-dried or spray-dried, concentrates, solutions, dispersions or other instant form, or the like.

Preferably, a pharmaceutical formulation (or also a nutraceutical in the form of a supplement) according to the invention (which is different from the corresponding fungus itself) comprises 0.001 to 100, e.g. 5 to 99, such as preferably 10 to 98, weight-% of a compound or mixture of compounds of the formula I according to the invention, the rest being pharmaceutically and/or nutraceutically acceptable carriers and optionally other customary additives.

The pharmaceutical or nutraceutical formulation(s) (=composition(s), also for non-therapeutic, e.g. cosmetic, use) according to the present invention can be for enteral, parenteral, topical or any other route of administration, especially enteral, e.g. anal, nasal or especially oral, and can be prepared in various forms, such as granules, tablets, pills, syrups, solutions, dispersions, suppositories, capsules, suspensions, salves, lotions and the like.

Pharmaceutical grade or nutraceutical grade organic or inorganic carriers (pharmaceutically or nutraceutically acceptable carriers or carrier materials) and/or diluents suitable for oral and topical use can be used to formulate compositions containing the therapeutically-active compounds. Diluents known in the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The compositions may also include one or more of the following: carrier proteins such as serum albumin; buffers; fillers such as microcrystalline cellulose, lactose, corn and other starches; binding agents; sweeteners and other flavouring or fragrancing agents; colouring agents; and polyethylene glycol. Those additives are well known in the art, and are used in a variety of formulations.

By "administered" herein is meant administration of a prophylactically and/or therapeutically effective dose of a compound of the formula I or an extract comprising compounds of the formula I or a mixture of compounds of the formula I to an animal, especially a patient. By "therapeutically effective dose" herein is meant a dose that produces the effects, for which it is administered, e.g. a reduction of weight, more especially due to body fat reduction or the amelioration of any one or more symptoms of the diseases, disorders or conditions mentioned above.

Preferably, the dosage of the compound or compounds of the formula I, based on the total weight of the compound(s) of the formula I, in both nutraceutical (including use as supplement) or pharmaceutical use typically is such that the amount of the compound(s) of the formula I administered to a patient is such that it is effective in activation of LXR, or preferably a daily dose of about 0.2 to 200 g, e.g. in one invention embodiment of 0.5 to 7 g, or in another invention embodiment of 0.1 to 10 g, is administered to a person with a weight of 70 kg per day in one or more, e.g. 1 to 3, dosages (children/persons with differing weights receive a correspondingly (e.g. proportionally to the weight) modified dosage).

A mammal or human, especially being a "patient" or "subject" for the purposes of the present invention, includes especially humans and further other mammalian animals. Thus, the compound or extract comprising a compound of the formula I, respectively, or a mixture of compounds of the formula I, are applicable to both humans and animals. In the preferred embodiment the patient is a human. The patients will be treated either in prophylactic or therapeutic intention, the latter e.g. to avoid regain in weight after a weight (especially body fat) reduction (e.g. to avoid the yo-yo effect), or to avoid weight gain (especially due to an increase in body fat) ab initio.

Typically, the compound(s) of the formula I having therapeutic and/or prophylactic activity mentioned hereinbefore (e.g. weight control, weight loss, body fat reduction, and/or agonistic activity on liver X receptor) may be administered with at least one physiologically (=pharmaceutically or nutraceutically) acceptable carrier to a patient, as described herein. The total concentration of therapeutically active triterpenoid derivative(s) of the formula I or a mixture of compounds of the formula I in the formulation may vary from about 0.001-99,999 wt %, e.g. from 0.1 to 50% by weight, the rest being the carrier material(s) and/or customary additives.

The compound(s) of the formula I as such, as extracts or as mixture may be administered alone or in combination with other drug compounds or treatments, i.e., other anti-obesity agents, common diets or the like. Thus the invention also encompasses combination preparations, comprising a compound of the formula I, or a pharmaceutically acceptable salt, hydrate or other solvate thereof, and one or more other drug compounds in free or pharmaceutically acceptable salt, hydrate or other solvate form, and optionally one or more pharmaceutically or nutraceutically acceptable carrier materials.

"Combination" does not necessarily mean a fixed combination but may also mean that the compound(s) of the formula I may be administered in a chronically staggered manner with the combination partner(s), e.g. in the form of a kit of parts (which also is an embodiment of the invention) with other combination partners. Preferably, the chronically staggered administration takes place such that the combination partners mutually influence, especially intensify (e.g. by way of an additive or preferably synergistic effect) their therapeutic efficiency.

Among other anti-obesity agents that may be combined, antilipidemics, e.g. atorvastatin, cerivastatin, fluvastatin, lovastatin, pravastatin, rosuvastatin, simvastatin, anti-obesity drugs, such as suppressants of the appetite, stimulators of the body's metabolism, or drugs or compositions interfering with the body's ability to absorb specific nutrients, such as sibutramine, diethylpropion, phendimetrazine, phentermine, fenfluramine, sibutramine, lipase inhibitors, such as orlistat; anorectics, such as dexedrine; cannabinoid receptor antagonists, such as rimonabant; acarbose; or the like, can be mentioned, without, however, limiting the possible combination partners. Other helpful drugs or active agents may be administered, e.g. psychoactive agents, agents that help in the treatment of addictive behaviour, e.g. nicotine addiction, or the like, especially in so far as they help to support the prophylaxis or treatment according to the invention intended.

Weight loss diets, such as food combining, Hay diet, Atkins diet (low-carbohydrate diet), cabbage soup diet, diabetic diet, fat resistance diet, slimming world diet, low-fat diet, Pritkin diet, low-carbohydrate diet, low protein diet, negative calorie diet, raw food diet, weight watchers diet are possible examples of appropriate diets.

The compound(s) of the formula I, extracts comprising them or a mixture of compounds of the formula I, itself or as mixtures of certain complexity, e.g. extracts or preparations, e.g. juices etc. of the above mentioned mushroom cultures, of this invention are particular useful for controlling the body weight, preferably the treatment of obesity or adipositas.

Natural compounds of the formula I, or extracts comprising one or more thereof, for USE according to the present invention are isolated from one or more cultures, especially liquid cultures, of mushrooms of the genera listed above or below, e.g. with the genetic characteristics provided in detail below.

By the term "extract", either a direct extract (in liquid or preferably dried form), e.g. obtained as described below, or preferably a further enriched extract (obtainable e.g. by one or more further purification steps after extraction, e.g. chromatography, for example as described below) containing one or more, preferably two or more compounds of the formula I is meant.

The compound(s) of the formula I in the form of an extract and extracts according to the invention can be obtained by extraction of liquid cultures, especially liquid mycelial cultures, of mushrooms of the genus *Agaricus*, e.g. mushrooms or parts thereof of the species *Agaricus*.

The compound(s) of the formula I, or an extract comprising one or more of them, of the present invention can be prepared by a process according to the invention by extracting and preferably enriching up to isolating them from the mushroom (especially *Agaricus* spp. with the ITS nr DNA features discussed below) or (especially corresponding) mushroom part (especially liquid (more especially mycelial) cultures. Auxiliary means such as (especially ultrasonic) sonication, heating (e.g. to temperatures from room temperature to 50° C.), stirring, re-extraction, evaporation or the like, may be used to allow for appropriate extraction.

Extraction preferably takes place with a non polar or weakly polar (meaning less polar than water) solvent or solvent mixture, meaning that the preferred obtainable or obtained extracts according to the invention are lipophilic extracts.

Preferably, the polarity is defined by an $E_T(30)$ value of 56 kcal/mol or lower (at 25° C. and 1 bar), e.g. of 52 kcal/mol or lower (water has an $E_T(30)$ of 63.1). The $E_T(30)$ method is based on a method published by Reichart et al. and makes use of the stabilisation of the ground state of the betaine dye 2,6-diphenyl-4-(2,4,6-triphenyl-1-pyridinio)phenolate, CAS number 10081-39-7, R: 22-24/25, in apolar solvents leading to a higher energy for the transition from the ground state (HOMO) to the first excited state (LUMO) of the molecule (see K. Dimroth, J Lieb Ann d Chemie (1963) 661(1): 1-37, DOI 10.1002/jlac.19636610102).

The compound(s) of the formula I, or an extract comprising one or more of them are well soluble in organic solvents like alcohols, e.g. in ethanol. The solubility is e.g. estimated to be more than 100 mg/ml. Less polar solvents like hydrocarbons, medium-chain triglycerides (MCT) or vegetable oils are good solvents, e.g. in n-heptane the solubility can be estimated to 10-100 mg/ml, whereas water is an inappropriate solvent, e.g. the solubility is less than 1 mg/ml. Examples of appropriate solvents are organic solvents (two or more of which can also be mixed), e.g. a ketone or an ester, such as acetone and/or ethyl acetate, an ether, e.g. a cyclic ether such as dioxane, and/or (also in a specific embodiment) an alcohol e.g. ethanol, and/or a liquid or superfluid gas, especially superfluid $CO_2$.

The pH value of the solvents can be modified by adding acids (trifluoroacetic acid, acetic and formic acid) or ammonium acetate, respectively.

Preferably, the solvent may be removed after extraction, e.g. by evaporation or precipitation (e.g. by the addition of water).

Preferably, the extracts can subsequently be further enriched by one or more additional purification steps, such as distribution, e.g. between an aqueous and an ether or ester (e.g. diethyl ether or ethyl acetate) phase for one or more times, precipitation (e.g. crystallisation) or especially chromatography, e.g. by HPLC or MPLC, by which it is possible to obtain further enriched extracts or isolated compounds of the formula I.

It is also possible to use other chromatographic methods such as gel permeation chromatography, countercurrent chromatography, or high speed counter current chromatography instead of the absorption chromatography described above.

Subsequent purification by preparative phase HPLC can also be carried out by the person skilled in the art using other stationary phases, such as RPB, phenyl, DIOL, C2, C4, C8 or amino.

The mobile phase mixtures may also contain additional other acids (for example formic acid) or additional buffers (for example ammonium acetate).

The compound(s) of the formula I can e.g. be isolated or the extracts prepared as described in the appended examples. The method for detection can comprise high pressure liquid chromatography (HPLC) or on reversed phase silica gel (C18) with water/acetonitrile-gradient as an elution solvent with UV as well as MS detection which are used for the product analysis and production optimization. It will be clear to those having ordinary skill in this art that the compound(s) of the formula I, though per se natural products, can alternatively be synthesized according to standard methods leading to compounds identical with the natural compounds, where appropriate methods, for example, can be deduced from the following publications: March's Advanced Organic Chemistry: Reaction, Mechanisms and Structure, 5th ed. by Michael B. Smith, Jerry March, Wiley-Interscience; 2001; Classics in Total Synthesis: Targets, Strategies, Methods by K. C. Nicolaou, E. J. Sorensen John Wiley & Son Ltd, 1996 and The Art and Science of Total Synthesis at the Dawn of the Twenty-First Century. Nicolaou K C et al., Angew Chem Int Ed Engl 2000, 39 (1): 44-122.

For example, the extraction or isolation and (partial or complete) purification of the compound(s) of the formula I can be conducted by removing the cellular and mycelial parts of the cultured mushroom material from the culture broth (e.g. by centrifugation and/or filtration) and removing the supernatant, extracting the obtained cellular and mycelial material as described above or in the examples to obtain a mycelial extract (which can already be used in the various embodiments of the invention) and, if desired, further purifying the compound(s) of the formula I, e.g. by solvent partition or chromatography, to yield the enriched or pure compounds.

Preferably, the compound or compounds, in the embodiments of the invention, are enriched in the mixtures or extract or purified extracts, or in another embodiment as single compound, to a percentage, in independent embodiments of the invention, of up to 10, 20, 30, 40, 50, 60, 70, 75, or (meaning in (essentially) pure form) up to 80, 85, 90, 92, 94, 95, 96, 97 or 98% or more than 98% by weight of the complete extract or purified extract, respectively.

Where USE is mentioned, this especially refers to one or more of the following embodiments of the invention which can be inserted wherever USE is mentioned:

(1) A compound of the formula I, an extract comprising a compound of the formula I or a mixture of compounds of the formula I, for use in therapeutic (including prophylactic) treatment of an animal, preferably a mammal, especially a human, against a disease, disorder or condition that responds to LXR activation; e.g. simply for maintenance of a healthy body, e.g. a low BMI, or especially treatment of obesity or one or more Syndrome X symptoms;

(2) A pharmaceutical or nutraceutical composition comprising a compound of the formula I, or a mixture of compounds of the formula I, as active ingredient together with a pharmaceutically or nutraceutically acceptable diluent or carrier, especially for use in the therapeutic and/or prophylactic treatment mentioned under (1).

(2') A pharmaceutical or nutraceutical composition for the treatment as mentioned under (1) comprising a compound of the formula I, or a mixture of compounds of the formula I, or especially a (preferably further enriched) extract comprising one or more compounds of the formula I, and a pharmaceutically or nutraceutically acceptable diluent or carrier, as active ingredient supplement to a food.

(3) A functional food comprising a compound of the formula I, or a mixture of compounds of the formula I, or especially a (preferably further enriched) extract, as active ingredient for the treatment as mentioned under (1).

(4) A method for the treatment as mentioned under (1), especially any one or more of obesity, and/or excess body fat, and/or one or more other symptoms of Syndrome X in a subject in need of such treatment, comprising administering a pharmaceutically or nutraceutically effective amount of a compound of the formula I, a mixture of compounds of the formula I, as active ingredient, to an individual ("individual" meaning a warm-blooded animal, especially a human, wherever mentioned), especially to an individual in need thereof.

(5) The use of a compound of the formula I, or a mixture of compounds of the formula I, as active ingredient for the manufacture of a medicament or nutraceutical or food supplement for the treatment mentioned under (1).

(6) A method or use as defined under (4), comprising co-administration, e.g. concomitantly or in sequence, of a therapeutically effective amount of compound of the formula I, or a mixture of compounds of the formula I, as active ingredient and a different pharmaceutically active compound and/or a pharmaceutically acceptable salt thereof, said different pharmaceutically active compound and/or salt thereof being especially for use in the treatment as mentioned under (1).

(7) A combination product comprising a therapeutically effective amount of a compound of the formula I, or a mixture of compounds of the formula I, as active ingredient, and a different pharmaceutically active compound and/or a pharmaceutically acceptable salt thereof, said second pharmaceutically active compound being especially for use or of use in the treatment mentioned under (1).

The USE may also be for purely cosmetic purposes or generally for non-therapeutic use as defined above), where in all embodiments of the invention, such as the above embodiments (1) to (7), "pharmaceutical", "pharmaceutically", "nutraceutical" and "nutraceutically" are replaced with "cosmetic" or "cosmetically", respectively, thus providing the corresponding embodiments for non-therapeutic use.

For any of the USEs, the USE is such that the compound(s) of formula I or mixtures thereof are the active ingredient, that is, they are already alone capable of achieving the intended effect (regulation of body weight and/or fat loss and/or management of obesity, especially decreasing of body weight, more especially decreasing body fat, and/or treatment of one or more symptoms of Syndrome X, and are thus themselves the important active principle for the treatment(s) mentioned. Throughout the present specification, the prophylactic and/or therapeutic treatment or regulation of body weight and/or fat loss and/or management of obesity, especially decreasing of body weight, more especially decreasing body fat, and/or treatment of one or more symptoms of Syndrome X, are especially preferred embodiments according to the invention.

In any of the USEs mentioned, the compound(s) of the formula I may be present and/or administered in free form, in the form of a pharmaceutically and/or nutraceutically acceptable salt, in the form of tautomers, in the form of solvates (e.g. hydrates) and, where esterifyable groups are present, e.g. hydroxyl, in the form of esters, such as lower alkanoylates, e.g. acetylates, aroylates, e.g. benzoylates, sulfonates, e.g. arylsulfonic acid esters, or the like (obtainable by reaction e.g. with the corresponding acid anhydrides, acid halogenides or by known amino acid coupling methods).

By "administering" herein is especially meant administration of a therapeutically or nutraceutically effective dose of a compound of the formula I, or a mixture of compounds of the formula I, to a cell either in cell culture or especially to an animal, especially a human patient. By "therapeutically or nutraceutically effective dose" herein is preferably meant a dose that produces the effects for which it is administered.

The pharmaceutical or nutraceutical preparations may be sterilized and/or may contain carrier materials or adjuvants such as preservatives, stabilizers, binders, disintegrants, wetting agents, skin or mucuous membrane penetration enhancers, emulsifiers, salts for varying the osmotic pressure and/or buffers, or other ingredients, excipients or carrier materials known in the art.

Isolated compounds according to the invention and for use according to the invention are shown in the following table:

TABLE 1

Isolated compounds

| Cmpd. number | Name; CAS Registry Number | Structure |
|---|---|---|
| 1 | Blazeispirol A; (2S,3S,3'R,4R,4'S,4aR,10bR)- 4,4',4a,5'-Tetrahydro-8-methoxy-3,4',4a,5',5',7-hexamethyl-spiro[4,10b-ethano-10bH-naphtho[1,2-b]pyran-2(3H),2'(3'H)-furan]-3'-ol CAS RN: 221115-51-1 | |
| 2 | Blazeispirol D (2S,3S,3'R,4R,4'S,4aR,10bR)-4,4',4a,5'-tetrahydro-3,4',4a,5',5',7-hexamethyl-spiro[4,10b-ethano-10bH-naphtho[1,2-b]pyran-2(3H),2'(3'H)-furan]-3',8-diol CAS RN: 348111-17-1 | |

TABLE 1-continued

Isolated compounds

| Cmpd. number | Name; CAS Registry Number |
|---|---|
| 3 | Blazeispirol E<br>(2S,3S,3'R,4R,4'S,4aR,10bR)-4,4',4a,5'-Tetrahydro-3'-hydroxy-8-methoxy-3,4',4a,5',5'-pentamethyl-spiro[4,10b-ethano-10bH-naphtho[1,2-b]pyran-2(3H),2'(3'H)-furan]-7-methanol<br>CAS RN: 348111-18-2 |
| 4 | Blazeispirol X<br>(2S,3S,3'R,4R,4'S,4aR,9S,12bR)-4,4',4a,5',8,9,10,11-Octahydro-3,4',4a,5',5',7-hexamethyl-spiro[4,12b-ethano-12bH-anthra[1,2-b]pyran-2(3H),2'(3'H)-furan]-3',9-diol<br>CAS RN: 292158-91-9 |
| 5 new | (14β,22S,23R)-14,22:22,25-Diepoxy-23-hydroxy-ergosta-4,7,9-triene-3,6-dione |
| 6 new | 23-epi-Blazeispirol U<br>(14β,22S,23S)-14,22:22,25-Diepoxy-23-hydroxy-ergosta-4,6,8,11-tetraen-3-one |

TABLE 1-continued

Isolated compounds

Cmpd. number | Name; CAS Registry Number
---|---

| 7 new | 17-Hydroxyblazeispirol A<br>(2S,3S,3'R,4R,4'S,4aR,10bR)- 4,4',4a,5'-Tetrahydro-17-hydroxy-8-methoxy-3,4',4a,5',5',7-hexamethyl-spiro[4,10b-ethano-10bH-naphtho[1,2-b]pyran-2(3H),2'(3'H)-furan]-3'-ol |
| 8 new | 12-Oxoblazeispirol C<br>(2S,3S,3'R,4R,4aR,4'S,10bS)-3'-hydroxy-8-methoxy-3,4a,4',5',5',7-hexamethyl-4,4a,4',5'-tetrahydro-3H,3'H-spiro[4,10b-ethanobenzo[h]chromene-2,2'-furan]-5(6H)-one |
| 9 new | (1R,2S,2'S,3'R,4aS,4'S,10aR,12R,12aS)-3',12-dihydroxy-2,4',5',5',10a,12a-hexamethyl-4',5',10,10a,12,12a-hexahydro-1H,3'H-spiro[1,4a-ethanonaphtho[1,2-h]chromene-3,2'-furan]-6,8(2H,9H)-dione |
| 10 new | (1R,2S,2'S,3'R,4aS,4'S,12aS)-3',12-dihydroxy-2,4',5',5',10a,12a-hexamethyl-4',5',6a,7,10,10a,12,12a-octahydro-1H,3'H-spiro[1,4a-ethanonaphtho[1,2-h]chromene-3,2'-furan]-6,8(2H,9H)-dione |

TABLE 1-continued

Isolated compounds

| Cmpd. number | Name; CAS Registry Number |
|---|---|
| 11 new | (1R,2S,2'S,3'R,4aS,4'S,12aR)-3',6a-dihydroxy-2,4',5',5',10a,12a-hexamethyl-4',5',6a,7,10,10a-hexahydro-1H,3'H-spiro[1,4a-ethanonaphtho[1,2-h]chromene-3,2'-furan]-6,8,12(2H,9H,12aH)-trione |
| 12 new | (1S,2S,2'S,3'R,4aS,4'S,12aR)-1,3'-dihydroxy-2,4',5',5',10a,12a-hexamethyl-4',5',10,10a-tetrahydro-1H,3'H-spiro[1,4a-ethanonaphtho[1,2-h]chromene-3,2'-furan]-6,8,12(2H,9H,12aH)-trione |
| 13 new | (2S,3S,3'R,4R,4aR,4'S,10bS)-3'-hydroxy-8-methoxy-3,4a,4',5',5',7-hexamethyl-4,4a,4',5'-tetrahydro-3H,3'H-spiro[4,10b-ethanobenzo[h]chromene-2,2'-furan]-5,6-dione |
| 14 | Blazeispirol C (2S,3S,3'R,4R,4aR,4'S,10bR)-8-methoxy-3,4a,4',5',5',7-hexamethyl-4,4a,4',5,5',6-hexahydro-3H,3'H-spiro[4,10b-ethanobenzo[h]chromene-2,2'-furan]-3'-ol CAS RN: 348111-16-0 |

Compounds of the invention e.g. these spiro ketal compounds exhibit an extraordinary activity at the LXR receptor.

Within the scope of the present invention it is important that there is a correlation between 5.8S/ITS nrDNA sequences and the ability of the production of the compounds of the invention and/or of use according to the invention.

The following Table (A) shows the strains of *Agaricus* spp. that were found to be devoid of blazeispirols in the mentioned media:

TABLE (A)

Strains of *Agaricus* spp. studied which were found devoid of blazeispirols in YMG, Q6/2 and ZM/2 media, using similar fermentation conditions that led to blazeispirol production in *Agaricus subrufescens* sensu Kerrigan (2005)

| Species | Strain | Collector/Isolator; Country of origin |
|---|---|---|
| *Agaricus arvensis* Schaeff.: Fr. | MUCL 35030 | C. Decock, Belgium |
| | DSM 8327 | P. Hübsch, Germany |
| | CBS 583.76 | W. Gams, Netherlands |
| *Agaricus augustus* Fr. | CBS 572.67 | G.A. de Vries, Netherlands; |
| | MUCL 35074 | C. Decock, Belgium |
| | CBS 173.75 | W. Gams, Netherlands |
| *A. bisporus* (Lange) Imbach | DSM 14900 | H. Müller, Germany |
| | CBS 505.73 | C. A. Raper, USA |
| *A. bitorquis* (Quél.) Sacc. | DSM 14895 | M. Stadler, Germany |
| | DSM 14594 | M. Stadler, Germany |
| | MUCL 28516 | G. L. Hennebert, Belgium |
| *A. campestris* var. campestris L.: Fr. | MUCL 29004 | G. L. Hennebert, Belgium |
| *A. macrosporus* (Moeller & J. Schaeffer) Pilát | MUCL 28242 | G. L. Hennebert, Luxembourg |
| | CBS 585.76 | W. Gams, Netherlands |
| | DSM 14593 | M. Stadler, Germany |
| | DSM 14594 | M. Stadler, Germany |
| *A. semotus* Fr. | DSM 6936 | J.T. Peng, Taiwan |
| *A. silvicola* (Vittad.) Peck | CBS 739.85 | |
| | ATCC 22039 | not stated, Czech Republic |
| *A. trisulphuratus* Berk. | CBS 271.81 | |
| *A. xanthoderma* Genev. | DSM 14901 | H. Müller, Germany |
| | MUCL 20967 | G. L. Hennebert, Belgium |
| | DSM8328 | P. Hübsch, Germany |

Strains of various other *Agaricus* species (as listed in the above Table A) were also subjected to fermentation in shake flasks according to the procedure described for production of blazeispirol, but were not found to produce the compounds after up to 800 hours of fermentation; this indicates that the strains listed here as *Agaricus subrufescens* sensu Kerrigan are specifically able to produce the blazeispirol type triterpenpoids.

Representative Strains Studied

*Agaricus subrufescens* strain FU70033 was purchased from "Dunkelhäuser Edelpilzzucht, Dunkelhäuser 14, 02929 Rothenburg, Germany". The strain is kept under liquid nitrogen at the culture collection of InterMed Discovery and was also deposited at the Mycothèque de l'Université catholique de Louvain (BCCM/MUCL), Croix du Sud 3, box 6, 1348 Louvain-la-Neuve, Belgium under the Budapest Treaty on Jul. 7, 2010. It is maintained at MUCL under the accession number MUCL 52948. At room temperature, the strain grows rather slowly on various culture media, producing white fluffy mycelium that is devoid of clamp collections; no peculiar morphological features were noted upon microscopic examination even in old cultures. This strain was used for fermentation and for isolation of the compounds of the invention in the Examples; however, some or all of these compounds can also be obtained from the following reference strains, as revealed by the analytical procedures carried out in the course of this invention:

*Agaricus subrufescens* strain MUCL 44605 was purchased from Mycothèque de l'Université catholique de Louvain (BCCM/MUCL). According to the catalogue of the provider, the strain was obtained by BCCM/MUCL from Western Biologicals Ltd., Canada in 2003. It is kept under liquid nitrogen at the culture collection of InterMed Discovery GmbH and was deposited again at the Mycothèque de l'Université catholique de Louvain (BCCM/MUCL) under the Budapest Treaty on Jul. 7, 2010. It is maintained at MUCL under the accession number MUCL 52947. At room temperature, the strain grows rather slowly on various culture media, producing white fluffy mycelium that is devoid of clamp collections; no peculiar morphological features were noted upon microscopic examination even in old cultures.

*Agaricus subrufescens* strain ATCC® 76739™ was purchased from the American Type Culture Collection, Manassas, Va., USA. According to catalogue of the provider, the strain was originally derived from Brazil, transferred to ATCC by T Mizuno, who in turn had obtained it from T. Furomoto. Japanese researchers had found "heteroglucans" with anticancer activity in this strain (Mizuno et al., Agric. Biol. Chem. 54: 2889-2896, 1990). The strain was also studied for comparison by Wasser et al. (Intl J Med Mush 2002, 4:267-290). It is kept under liquid nitrogen at the culture collection of InterMed Discovery GmbH and was deposited again at the Mycothèque de l'Université catholique de Louvain (BCCM/MUCL) under the Budapest Treaty on Jul. 7, 2010. It is maintained at MUCL under the accession number MUCL 52949. At room temperature, the strain grows rather slowly on various culture media, producing white fluffy mycelium that is devoid of clamp collections; no peculiar morphological features were noted upon microscopic examination even in old cultures.

*Agaricus* sp. strain ATCC® 34722™ was purchased as *Agaricus subrufescens* from the American Type Culture Collection, Manassas, Va., USA. According to the catalogue of the provider, the strain was originally derived from Nahant, Mass. by M. Benson and later deposited with ATCC by C. A. Raper. Its characteristics were reported previously by Raper & Kaye, J. Gen. Microbiol. 105: 135-151, 1978. Even though the strain was obtained under the name *Agaricus subrufescens*, its secondary metabolite profiles and ITS nrDNA data deviated from those of the strains that are subject of the current invention. It did not produce the compounds that are subject of this invention.

The taxonomy of all strains of *Agaricus subrufescens* listed above is verified by generating their 5.8S/ITS nrDNA sequences, using the well-established procedure described by Bitzer et al. (Mycological Res. (2008) 112: 251-270. The sequences are deposited at the databases of the European Molecular Biology Laboratory (http://www.embl.de) as well as in GenBank (http://www.ncbi.nlm.nih.gov). Subsequences of 5.8S/ITS nrDNA sequences referring to ITS1 nrDNA used for the sequences comparison experiments of this invention were provided in this patent application under Sequence Listing Nos. 1-4.

As revealed by similarity searches using the programme FASTA (http://www.ebi.ac.uk; European Bioinformatics Institute, Wellcome Trust Genome Campus, Hinxton, Cambridge, CB10 1SD, UK), ITS 1 nrDNA sequences of all strains are at least 96.5% identical to one another and also to the strains of *Agaricus subrufescens* studied by Kerrigan (Mycologia 2005), as well as to some sequences deposited under the names *Agaricus blazei*, *Agaricus rufotegulis* and

*Agaricus brasiliensis* in the above database. These findings, along with the fact that all studied strains contained the same secondary metabolites, are all in agreement with the hypothesis that all the four above names are synonyms.

It was surprisingly found to be supported by data that only strains with a high identity in the ITS 1 nrDNA sequence are able to produce the compounds of the invention regardless of the used name for these species e.g. *A. blazei, A. brasiliensis, Agaricus rufotegulis* and *A. subrufescens*.

It can be expected that all other genuine strains that have been treated in the literature under the names *Agaricus blazei, Agaricus brasiliensis* and *Agaricus subrufescens* will also be suitable to produce the compounds that are the subject of the current invention. Notable, the four selected strains have all been eventually used to produce fruiting bodies for food and/or medicinal purposes.

5.8S/ITS nuc-rDNA (in the following referred to as ITS nr DNA) sequences are commonly used to describe fungus species on their genetic level. This region is located between the 18S and the 28S ribosomal RNA gene, thus the complete region used for sequence comparison purposes which must be isolated from any fungal organism is 18S ribosomal RNA gene, partial sequence; internal transcribed spacer 1 (ITS 1), 5.8S ribosomal RNA gene, and internal transcribed spacer 2 (ITS 2), complete sequence; and 28S ribosomal RNA gene, partial sequence.

For the purpose of this invention the isolated sequence of the 5.8S/ITS nuc-rDNA sequences as well as the isolated ITS 1 nr DNA sequences are used.

"ITS nrDNA" sometimes also named as "ITS nuc-rDNA" refers to the internal transcribed spacer of the nuclear ribosomal DNA which doesn't code for any protein or peptide. ITS 1 nrDNA refers to the first spacer sequence located between 18S and 5.8S ribosomal RNA genes.

In a preferred embodiment, the ITS 1 nr DNA sequence according to the invention comprises a sequence having a "Similarity" with <SEQ ID NO: 1> of at least 96.5%, 97%, 97.5%, 98%, 98.5%, 99%, at least 99.1%, 99.2%, 99.3%, 99.4%, 99.5%, 99.6%, 99.7%, 99.8%, 99.9% and in particular 100%, preferably determined by means of the FASTA software specified in further detail below and especially in the examples.

In a second preferred embodiment, the ITS 1 nr DNA sequence according to the invention comprises a sequence having an "Identity" with <SEQ ID NO: 1> of at least 96.5%, 97%, 97.5%, 98%, 98.5%, 99%, at least 99.1%, 99.2%, 99.3%, 99.4%, 99.5%, 99.6%, 99.7%, 99.8%, 99.9% and in particular 100%, preferably determined by means of the FASTA software specified in further detail below and especially in the examples.

In one embodiment of the invention producer strains of *A. subrufescens, A. blazei, A. rufotegulis,* and/or *A. brasiliensis* are understood as being able to produce in principle the compounds of the invention.

Common names of this species are Almond Mushroom, Mandelpilz, Brasilianischer Mandelegerling, Himematsutake, sun mushroom, Brazilian sun-mushroom; kawariharatake, Cogumelo Piedade, cogumelo de deus, Mushroom of God, cogumelo de sol, Mushroom of the sun, cogumelo de vida, Mushroom of life, Royal Sun *Agaricus*.

In another embodiment producer strains of the invention are those being characterized by their ITS 1 nr DNA comprising a sequence as being similar and/or identical with at least 96.5%, 97%, 97.5%, 98%, 98.5%, 99%, at least 99.1%, 99.2%, 99.3%, 99.4%, 99.5%, 99.6%, 99.7%, 99.8%, 99.9% and in particular 100%, as defined above with any one of the <SEQ ID NO: 1>, <SEQ ID NO: 2> and <SEQ ID NO: 3>.

This is valid independent from any taxonomic description or classification in the state of the art or the ethnobiological ITS 1 nr DNA, so that all strains fulfilling the above requirements are appropriate producer strains according to the invention.

In another embodiment the extracts mentioned in this invention are substantially free of saccharides, more specified free of polysaccharides and in particular free of betaglucan.

In another embodiment the extracts mentioned in this invention are substantially free of triterpenes not containing a spirocyclic structure.

In another embodiment the extracts mentioned in this invention are substantially free of Agaritin.

The used ITS 1 nr DNA sequences do not code for any protein or peptide thus encodes no corresponding amino acid sequence.

"Identity" and "similarity" (sometimes also referred to as "homology") with respect to a nucleic acid is defined herein as the percentage of nucleic acid in the candidate sequence that are identical with the residues of a corresponding native nucleic acid, after aligning the sequences and introducing gaps, if necessary, to achieve the maximum percent identity/similarity, and considering any conservative substitutions according the NC-IUB rules (http://www.chem.gmul.ac.uk/iubmb/misc/naseq.html; NC-IUB, Eur J Biochem (1985) 150:1-5) as part of the sequence identity. Neither 5' or 3' extensions nor insertions shall be construed as reducing identity, similarity or homology. Methods and computer programs for the alignments are well known and specifically named below and in the examples.

The sequence comparisons with strains of the prior art which are public domain databases made available in the internet, e.g. in GenBank, EMBL Data Library, DNA Database of Japan (DDBJ), National Center for Biotechnology Information (NCBI), are performed online using the program FASTA3 (http://www.ebi.ac.uk/Tools/fasta/; European Bioinformatics Institute, Wellcome Trust Genome Campus, Hinxton, Cambridge, CB10 1SD, UK) Version 35.04 (20 Feb. 2010).

Figure 3:
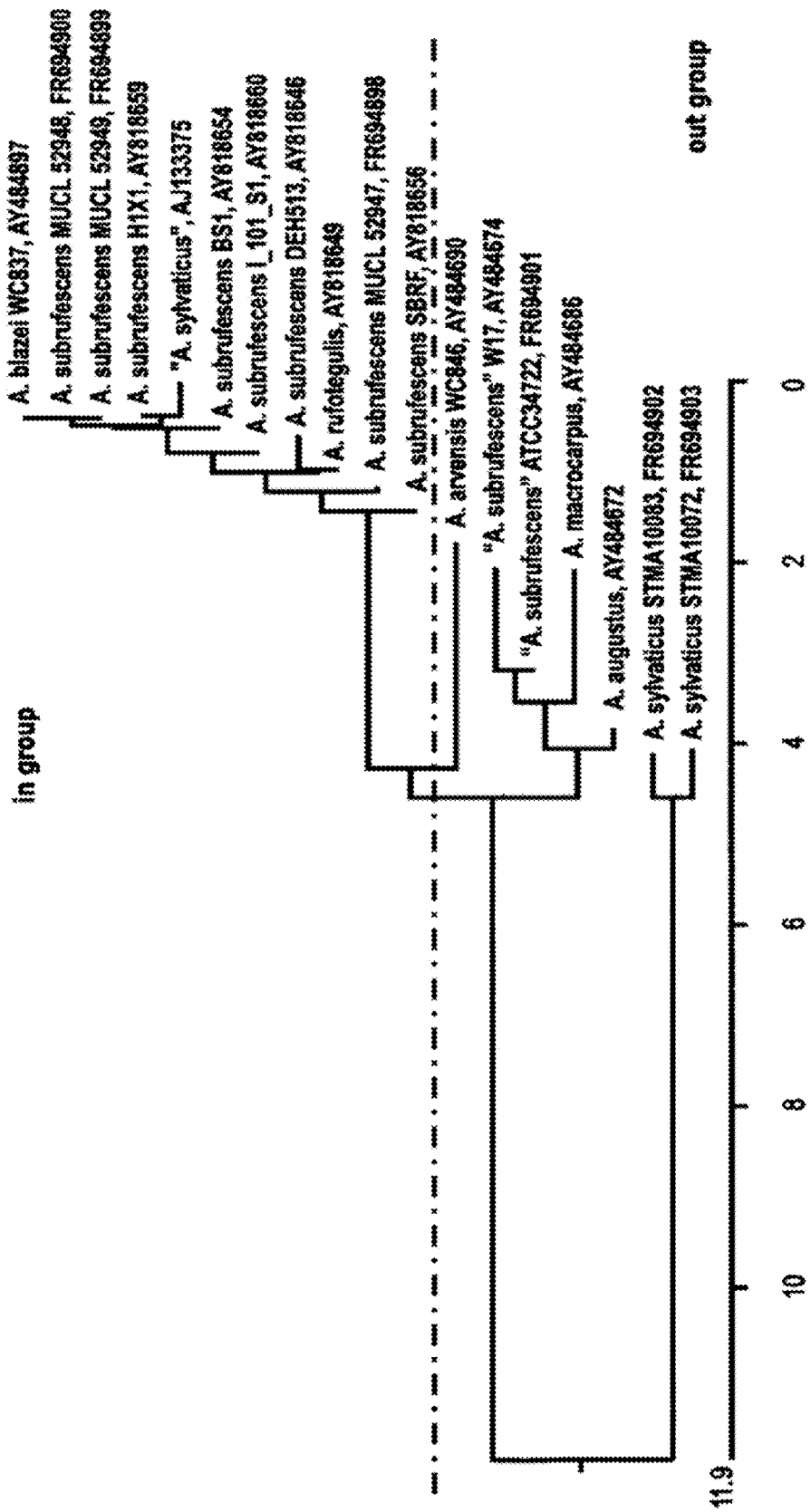
FIG. 3: Phylogenetic tree of the strains which were compared in the example 5

The phylogenetic tree presented in FIG. 3 is prepared with the ITS 1 nr DNA sequences. The used strains sequences are public domain and defined by their Accession Numbers in GenBank or are sequences of the present invention: <SEQ ID NO: 1>, <SEQ ID NO: 2>, <SEQ ID NO: 3>, and <SEQ ID NO: 4>. For these comparisons different programs are available using the method Clustal (Desmond et al., *Comput. Appl. Biosci.* (1989) δ: 151-153; Eugene W. et al., *Comput. Appl. Biosci.* (1988) 4: 11-17). This method is incorporated in the program MegAlign™ as part of the Lasergene® Suite (trademarks of DNAStar Inc., Madison, U.S.A.) for Windows 32 Version 3.16 used for the purpose of this invention.

Pairwise comparison of selected ITS 1 nr DNA are performed with BLASTN 2.2.24 (Zheng Zhang et al. J Comput Biol (2000) 7(1-2):203-14).

The parameter settings of the above cited programs and methods as well as the definition of the subsequences and parts of these sequences are explained in the examples which are incorporated here also in support of the generic disclosure and definitions of the invention.

EXAMPLES

The following Examples illustrate the invention without limiting its scope.

General Methodology

A Analytical Procedures

HPLC-UV/Vis analyses are carried out as described by M. Stadler et al., Mycol. Res., 2001, 105, 1190-1205 on a HP 1100 Series analytical HPLC system (Agilent, Waldbronn, Germany) comprising a G 1312A binary pump system, a G 1315A diode array detector, a G 1316A column compartment, a G 1322A degasser and a G 1313A auto-injector. As mobile phase, 0.01% $H_3PO_4$ acetonitrile (ACN) is chosen, while a Merck (Darmstadt, Germany) LichroSpher RP 18 column (125×4 mm, particle size 7 µm) serves as stationary phase. Aliquots of the samples (representing 2-10 µg of methanol-soluble materials, according to the concentrations of main metabolites) are analyzed at 40° C. with a flow of 1 ml/min in the following gradient: Linear from 0% acetonitrile to 100% acetonitrile in 10 min, thereafter isocratic conditions at 100% acetonitrile for 5 min; followed by regeneration of the column for 5 min. HPLC-UV chromatograms are recorded at 210 nm with a reference wavelength of 550 nm and a bandwidth of 80 nm. Diode array detection (DAD) is employed to record HPLC-UV/Vis spectra in the range of 210-600 nm. The HP ChemStation software allows for an automated search for calibrated standard compounds in crude extracts, as well as for quantitative estimation of the production of blazeispirols during fermentation, using external and internal standards for calibration.

B LC-MS Method

LC-MS/UV analyses for dereplication as described by J. Bitzer et al, Chimia 2007, 61, 332-338 were performed using an Agilent HP1100 (Agilent, Waldbronn, Germany) liquid chromatograph coupled with a LCQ™ (Trademark by Finnigan) Deca XPplus mass spectrometer (Thermo Fisher Scientific, Waltham, Mass., USA) in the positive and negative electrospray ionization (ESI) mode. A Waters symmetry column (Waters Symmetry® (Trademark by Waters) C18, 3.5 µm, 2.1 mm×150 mm, Waters GmbH, Eschborn, Germany) was used as stationary phase with a flow rate of 0.4 ml/min at 40° C. Mobile phase A: 0.1% formic acid in water, mobile phase B: 0.1% formic acid in acetonitrile; gradient: 0-1 min. 98% A, from 1-21 min. to 100% B, from 21-27 min 100% B. The UV/Vis (ultraviolet/visible light) spectra were recorded between 200-500 nm, the LC-MS (Liquid Chromatography-Mass Spectrometry coupling) spectra were recorded in the range of molecular weights between 160 and 1.600 U.

C Preparative LC-Methods

Preparative HPLC is performed at room temperature on a preparative HPLC system (Gilson Abimed, Ratingen, Germany), comprising Unipoint™ System Software (trademark by Gilson) software, 306 binary pump system, 205 fraction collector, 119 UV-Vis detector, 806 manometric module, and 811C dynamic mixer, using different gradients and stationary phases as described below.

Flash chromatography is performed at room temperature on a Biotage (Uppsala, Sweden) system, using C18 reverse phase cartridge columns, (KP-SIL, Article No. FKO-1107-19073; cm high×9 cm diam.) combined with a fraction collector using different gradients.

HR-ESI-MS (High Resolution Electrospray Ionisation Mass Spetrometry) data were obtained on a Bruker MicroTOF (Bruker Daltonik GmbH, Leipzig, Germany) instrument, coupled with a HPLC system as described before and using sodium formate as internal reference.

NMR spectra are recorded on a Bruker DMX500, operating at 500.13 MHz proton frequency. All spectra are measured in $CDCl_3$ solution at 293 K. The solvent peak is used as internal reference for both proton and carbon chemical shifts ($\delta H$, 7.26, $\delta C$, 77.0). Standard Bruker pulse sequences were used to obtain $^1H$, $^{13}C$, $^1H$, $^1H$-gCOSY, $^1H$, $^{13}C$-gHSQC and $^1H$, $^{13}C$-gHMBC spectra.

Example 1

Fermentation

Culture Media:

Media constituents were obtained in analytical grade from Merck (Darmstadt, Germany) and other chemicals from Sigma-Aldrich (Deisenhofen, Germany), if not stated otherwise. Culture media were made by adding the constituents listed below, and then sterilized by autoclaving (flasks and agar plates) or by sterilization with steam in situ (fermentors) for 30 min at 121° C. For solid media, 1.5% Difco Bacto agar (Beckton Dickinson, Heidelberg, Germany) was added prior to sterilization, and the plates (9 cm diameter) were prepared by pouring 20 ml of the solid medium into sterile disposable petri dishes.

YMG medium: glucose 0.4%, malt extract (Löflunds, Dr. Fränkle and M. Eck, Fellbach, Germany) 1%, yeast extract 0.4%, pH adjusted to 6.3 (prepared with tap water).

ZM/2 medium: molasses (Südzucker, Mannheim, Germany) 0.5%, oatmeal (Kornmühle Hamburg, Germany) 0.5%, glucose 0.15%, Sucrose 0.4%, mannitol 0.4%, edamine S (Sigma, Deisenhofen, Germany) 0.05%, $Na_2SO_4$ 0.05%, $CaCO_3$ 0.15%, pH adjusted to 7.2 (prepared with tap water).

Malt medium: malt extract (Löflunds) 2%; no pH adjustment (prepared with tap water).

GDYP medium: (Han et al., J. Microbiol. Biotechnol. (2004) 14: 944-951) glucose 1%, dextrin 4%, yeast extract 0.4%, soy peptone (Bacto Peptone, BD Bioscience, Heidelberg, Germany) 0.2%, $KH_2PO_4$ 0.2%, $MgSO_4 \times 7H_2O$ 0.05%, $FeCl_3 \times 6\ H_2O$ 0.2% (prepared with tap water).

SYM medium: (Hirotani et al. (*Tetrahedron Lett* (1999) 40: 329-332) Sucrose 1%, yeast extract 0.5%, malt extract 3%, prepared with distilled water.

Q6/2 medium: D-glucose 0.2%, glycerol 1%, cotton seed meal, 0.5%; prepared with tap water, pH 7.2.

Fermentation and Extraction of Strain *Agaricus subrufescens*:

a. Seed Culture

Seed cultures were initiated by placing ca. 20 small pieces of mycelia on agar plugs from 3 weeks old YMG agar plates into 500 ml Erlenmeyer flasks containing 200 ml YMG or GDPY medium. These flasks were grown for 7-10 days on a rotary shaker at 23° C. and 140 rpm, resulting in the formation of small mycelial pellets. These pellets were homogenized in analogy to the procedure described by Han et al. (J. Microbiol. Biotechnol. (2004), 14(5): 944-951) and the resulting homogenized mycelial suspension was then used as inoculum for the larger fermentation batches described further below.

b. Batch Fermentation of *Agaricus subrufescens* Strain MUCL 52948 in Flask Scale and Extraction with Acetone After inoculation from a well-grown seed culture (2.5 ml inoculum per flask), strain MUCL 52948 was propagated in fifty 500 ml Erlenmeyer flasks, containing each 200 ml of ZM/2 medium and propagated on a rotary shaker at 23° C. and 140 rpm for up to 552 h. During fermentation, samples were taken for analysis of blazeispirols by HPLC-MS, revealing that production of the secondary metabolites started after 168 h and reached its maximum after 400 h. After harvest, the wet mycelium (ca. 625 g) was separated from the fluid by filtration and extracted with 1l of acetone. The acetone was evaporated in vacuo (40° C.). The remaining aqueous residue was diluted with water to 500 ml and extracted three times with equal amounts of ethyl acetate. The combined organic phases were dried and filtered over anhydrous sodium sulphate, to remove all remaining water-soluble components, and evaporated in vacuo (40° C.) to yield 2.8 g of an organic crude extract, which was thereafter subjected to preparative chromatography as described below (isolation). The culture fluid was discarded.

c. Batch Fermentation of *Agaricus subrufescens* Strain MUCL 52948 in Flask Scale and Extraction with Ethanol After inoculation from a well-grown seed culture (2.5 ml inoculum per flask), strain MUCL 52948 was propagated in one hundred 500 ml Erlenmeyer flasks, containing each 200 ml of ZM/2 medium and propagated on a rotary shaker at 23° C. and 140 rpm for up to 496 h. During fermentation, samples were taken for analysis of blazeispirols by HPLC-MS, revealing that production of the secondary metabolites started after 168 h and reached its maximum after 400 h. After harvest, the wet mycelium (ca. 1025 g) was separated from the fluid by filtration and extracted twice with 1250 ml of absolute ethanol using ultrasonic. The ethanol was evaporated in vacuo (40° C.). The remaining aqueous residue was diluted with water to 250 ml and extracted two times with equal amounts of ethyl acetate. The combined organic phases were dried and filtered over anhydrous sodium sulphate, to remove all remaining water-soluble components, and evaporated in vacuo (40° C.) to yield 3.2 g of an organic crude extract (hereinafter referred to as IMD-XT0022), which was thereafter subjected for animal studies as described below. The culture fluid was discarded.

d. Fermentation of *A. subrufescens* Strain MUCL 52948 in 10l Scale (Shake Fermentor)

Ten liters of ZM/2 medium were filled in a disposable plastic bag and sterilized, incubated on a 10 l Biowave fermentor (WaveBiotech, Tagelswangen, Switzerland) and inoculated with 800 ml seed culture. The production culture was grown under shaking (motor setting 42 rpm) and aeration (0.5 l/min). Analytical HPLC of crude extracts prepared from 20 ml samples taken under sterile conditions and extracted with equal amounts of ethyl acetate served as a means of detection for blazeispirols. For this purpose, the ethyl acetate extracts were dried over sodium sulfate, evaporated to dryness, re-dissolved in methanol and analyzed using the HPLC systems as described in the General Methodology above. Blazeispirol production was observed after 500 h. The fermentation was terminated, and the mycelia were harvested by filtration. The culture filtrate was discarded for lack of blazeispirols in significant quantities. The wet mycelium (ca 33 g) was extracted three times with each 0.5 l of acetone, and the acetone was evaporated in vacuo (40° C.) to yield an aqueous residue, which was diluted to 100 ml with water and extracted three times with 100 ml ethyl acetate. The combined organic phases were dried and filtered over anhydrous sodium sulfate, to remove all remaining water-soluble components, and evaporated in vacuo (40° C.) to yield ca. 4 g of an organic crude extract, which was thereafter subjected to preparative chromatography as described below (isolation). The aqueous phases were discarded.

e. Fermentation in Other Culture Media (Flask Scale)

Strains MUCL 52947, MUCL 52948 and MUCL 52949 which were all assigned to be *A. subrufescens* in the sense of the invention were propagated in various other culture media (ZM/2, YMG, Malt, GDYP, SYM), in attempts to optimize production of sprioketal triterpenes. Additionally the strain ATCC 34722 is also fermented under the same conditions in order to detect any of the compounds of the invention. For this purpose, additional shake flask fermentations were carried out. Batches of ten 500 ml Erlenmeyer flasks containing 200 ml of the media were thus propagated on a rotary shaker at 23° C. and 140 rpm for up to 700 h. During fermentation, samples were taken as biomass production is noted. The pH was determined, and free glucose was estimated using Medi-Test Harnzuckerstreifen (Macherey&Nagel, Düren, Germany). Aliquots of the culture broth containing the mycelia (20 ml) were extracted with ethyl acetate. These ethyl acetate extracts were dried over sodium sulphate, evaporated to dryness, re-dissolved in methanol and analyzed using the HPLC-UV and HPLC-MS systems described in the General Methodology above.

f. Fatty Oil Extracts

After fermentation according to example 1b the whole combined liquid fermentation culture (i.e. before the harvest step in example 1b) having a total volume of 4000 ml was frozen by using a cooling bath (dry ice/ethanol in a 1:1 ratio). The frozen fermentation culture then was freeze-died (LYOWALL, AMSCO/FINN-AQUA, Hamburg, Germany) for 72 hours at 0.35 bar yielding 64 g freeze-dried fermentation culture. After milling said freeze-dried fermentation culture to a fine powder [particle size 10 µm] two 25 g portions thereof were extracted. In a first experiment, 25 g of said freeze-dried fermentation culture powder were extracted with 150 ml (133 g) sunflower oil (JA!™ sunflower oil, REWE-Handelsgruppe GmbH, Cologne, Germany) for 3 hours at 22° C. using a magnetic stirrer. After centrifugation 108 ml (97.4 g) of a yellow oil extract were obtained. In a separate experiment, 25 g of said freeze-dried fermentation culture powder were extracted with 150 ml (138 g) Delios V oil (medium-chain triglyceride (MCT) oil; BASF Personal Care and Nutrition GmbH, Düsseldorf, Germany) under same conditions as described above. After centrifugation 110 ml (102.5 g) of a yellow oil extract were obtained. Blazeispirol A (1) was present in both fatty oil extracts in an amount of several percent.

Example 2

Isolation

Starting form the mycelial extract of flask fermentations, blazeispirols (entry 1-14 Table 1) are isolated to purity by three consecutive steps, using a HPLC-MS guided isolation procedure.

a. Flash Chromatography for Crude Fractionation of Mycelial Extract

Ten grams of crude mycelial extract (e.g. resulting from example 1b) derived from fermentation of *A. subrufescens* were applied onto the Biotage chromatography system and fractionated using water:acetonitrile (ACN) as mobile phase at a flow of 20 ml/min. The column was rinsed with 1l water:ACN 1:1, followed by elution with two liters of 100% ACN. All fractions eluted with 50% ACN were discarded for lack of blazeispirols.

The blazeispirols (in total ca. 600 mg, including Blazeispirol A) started to elute immediately after 100% ACN was applied (at 50 min) and were collected in several intermediate fractions. The major product Blazeispirol A (1) was contained in a fraction (ca. 150 mg of ca. 95% purity) that elutes at 62-65 min with ca. 240-300 ml of 100% ACN.

In fractions eluting subsequently, only fatty acids and other lipophilic materials were observed by HPLC-MS, and those fractions were discarded.

These intermediate products were subjected to repetitive preparative HPLC, using the following chromatographic systems (FIG. 1)

b. Fractionation by Preparative HPLC

Purifications of blazeispirols were performed in two different ways as presented herein.

I For fractionation of the intermediate products, a MZ Analysentechnik (Mainz, Germany) Kromasil RP 18 column; particle size, 7 μm; column dimensions: 250×40 mm; mobile phase, 0.01% TFA: acetonitrile (ACN); flow of 10 ml/min: column equilibrated at 20% ACN at t=0 min; linear gradient: 20% to 100% ACN in 80 min; thereafter isocratic conditions at 100% acetonitrile for 30 min. Fractions were combined according to UV adsorption at 210 nm and concurrent HPLC-MS analyses.

Figure 2:
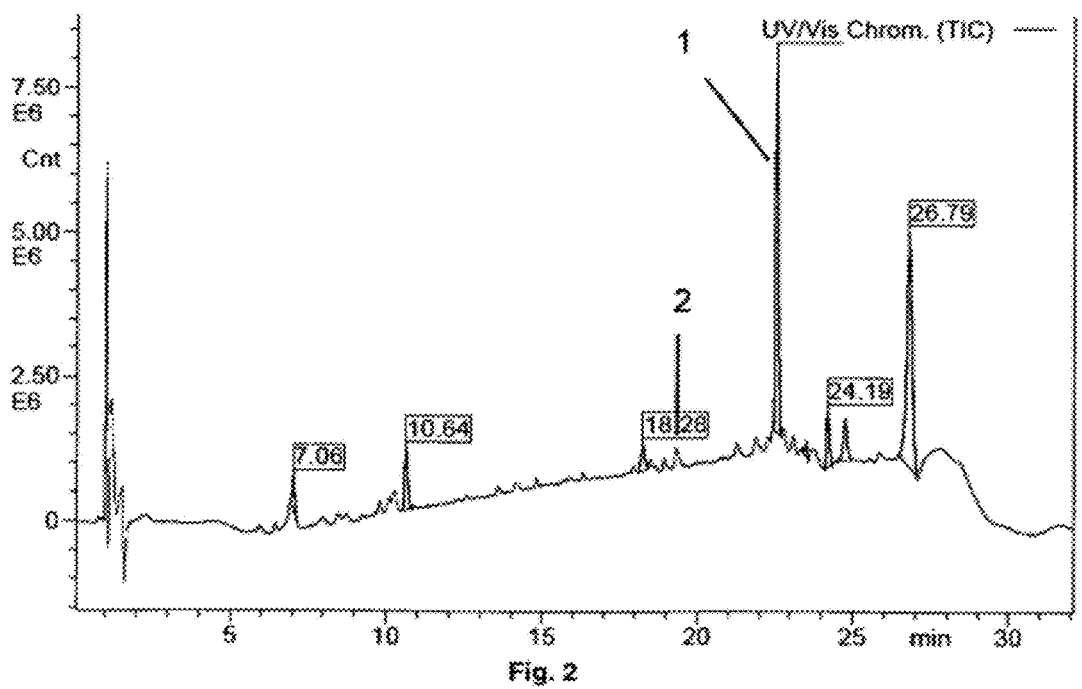
FIG. 2: Typical analytical HPLC chromatogram of a product of example 1c, assigned signals refer to Table 1

Final purification of blazeispirols was done using a Waters (Eschborn, Germany) SymmetryPrep C18 column; particle size, 7 μm; column dimensions: 300×19 mm was used. Elution was performed with the following regiment: mobile phase, 0.01% TFA: acetonitrile (ACN); flow of 7 ml/min: column equilibrated at 20% ACN at t=0 min; linear gradient: 20% to 100% ACN in 60 min; thereafter isocratic conditions at 100% acetonitrile for 30 min. Fractions were combined according to UV adsorption at 210 nm and concurrent HPLC-MS analyses, and their purity and identity was finally confirmed by HR-MS and 2D-NMR. Yields of individual blazeispirols varied according to the fermentation batch used for compounds 2-14 (Table 1) between 1 and 5 mg. However, the final yield of blazeispirol A (1) obtained always exceeded 100 mg from 10 g crude extract, and over 95% of the metabolites contained in the intermediate fractions after the flash chromatography constitute blazeispirols. Several further metabolites that also belong to the blazeispirol type according to HPLC-MS data, as judged from their similar MS spectra and UV-Vis spectra could be obtained as assigned in the HPLC of the crude extract (FIG. 2).

II A mycelial extract (ca 3 g, result of example 1b) was dissolved in 5 ml of MeOH (Methanol) and separated by using the Gilson preparative HPLC system. As stationary phase, a GL Sciences Inc. (Sinjuku-Ku, Tokyo, Japan) Inertsil ODS-3 column 250×50 mm (Serial No. 4KI44004) was employed. 0.1% aqueous TFA (Trifluoroacetic acid)/Methanol was chosen as mobile phase. After equilibration of the column with 50% aqueous TFA, the sample was injected, and a linear gradient ranging from 50% 0.1% aqueous TFA to 100% ACN (Acetonitrile) was applied for 90 min. The flow was adjusted to 10 ml per minute and fractions (10 ml) were collected by a fraction collector. The separation was monitored by a diode array detector at 210 nm and 254 nm. The fractions were combined according to UV absorption peaks and concentrated in vacuo. The weight of the fractions was determined, and subsequently the fractions were analyzed by analytical HPLC-MS.

Blazeispirol A (entry 1 Table 1) eluted from the column at ca. 53-64 min, with the fraction eluting at 60-61 min (equivalent to ca. 95% methanol in the gradient) showing a purity of higher than 90%. The fractions eluting after 53-59 and 62-64 min, respectively contained higher amounts of impurities. They were therefore subjected to repetitive HPLC using similar conditions, which yielded another 100 mg of Blazeispirol A.

Retention times of blazeispirols as well as the characteristic signals observed upon ESI-MS are summarized in Table 2.

c. Identification of Blazeispirols

LC-MS/UV analyses for dereplication were performed using an Agilent HP1100 (Agilent, Waldbronn, Germany) liquid chromatograph coupled with a LCQ™ (Trademark by Finnigan) Deca XPplus mass spectrometer (Thermo Fisher Scientific, Waltham, Mass., USA) in the positive and negative electrospray ionization (ESI) mode. A Waters symmetry column (Waters Symmetry® (Trademark by Waters) C18, 3.5 μm, 2.1 mm×150 mm, Waters GmbH, Eschborn, Germany) was used as stationary phase with a flow rate of 0.4 ml/min at 40° C. Mobile phase A: 0.1% formic acid in water, mobile phase B: 0.1% formic acid in acetonitrile; gradient: 0-1 min. 98% A, from 1-21 min. to 100% B, from 21-27 min 100% B. The UV/Vis (ultraviolet/visible light) spectra were recorded between 200-500 nm, the LC-MS (Liquid Chromatography-Mass Spectrometry coupling) spectra were recorded in the range of molecular weights between 160 and 1.600 U.

HR-ESIMS (High Resolution Electrospray Ionisation Mass Spectrometry) data were obtained on a Bruker Micro-TOF (Bruker Daltonik GmbH, Leipzig, Germany) instrument, coupled with a HPLC system as described before and using sodium formate as internal reference.

TABLE 2

| Cmpd. Number | Name; CAS RN | RT (min)* | Detected ions |
|---|---|---|---|
| 1 | Blazeispirol A<br>CAS RN: 221115-51-1 | 22.58 | m/z 381.3 $[M + H - H_2O]^+$ |
| 2 | Blazeispirol D<br>CAS RN: 348111-17-1 | 19.31 | m/z 367.3 $[M + H - H_2O]^+$ |
| 3 | Blazeispirol E<br>CAS RN: 348111-18-2 | 18.38 | m/z 397.4 $[M + H - H_2O]^+$ |
| 4 | Blazeispirol X<br>CAS RN: 292158-91-9 | 19.44 | m/z 439.2 $[M + H]^+$ |
| 5 new | (14β,22S,23R)- 14,22:22,25-Diepoxy-23-hydroxy-ergosta-4,7,9-triene-3,6-dione | 19.10 | m/z 453.4 $[M + H]^+$ |
| 6 new | 23-epi-Blazeispirol U | 20.46 | m/z 437.3 $[M + H]^+$ |
| 7 new | 17-Hydroxyblazeispirol A | 18.83 | m/z 397.2 $[M + H - H_2O]^+$ |
| 8 new | 12-Oxoblazeispirol C | 20.25 | m/z 397.3 $[M + H - H_2O]^+$ |

TABLE 2-continued

HPLC-MS data of isolated compounds

| Cmpd. Number | Name; CAS RN | RT (min)* | Detected ions |
|---|---|---|---|
| 9 new | (1R,2S,2'S,3'R,4aS,4'S,10aR,12R,12aS)-3',12-dihydroxy-2,4',5',5',10a,12a-hexamethyl-4',5',10,10a,12,12a-hexahydro-1H,3'H-spiro[1,4a-ethanonaphtho[1,2-n]chromene-3,2'-furan]-6,8(2H,9H)-dione | 15.86 | m/z 469.4 [M + H]$^+$<br>m/z 513.5 [M − H + FA]$^-$ |
| 10 new | (1R,2S,2'S,3'R,4aS,4'S,12aS)-3',12-dihydroxy-2,4',5',5',10a,12a-hexamethyl-4',5',6a,7,10,10a,12,12a-octahydro-1H,3'H-spiro[1,4a-ethanonaphtho[1,2-h]chromene-3,2'-furan]-6,8(2H,9H)-dione | 14.95 | m/z 471.4 [M + H]$^+$<br>m/z 515.4 [M − H + FA]$^-$ |
| 11 new | (1R,2S,2'S,3'R,4aS,4'S,12aR)-3',6a-dihydroxy-2,4',5',5',10a,12a-hexamethyl-4',5',6a,7,10,10a-hexahydro-1H,3'H-spiro[1,4a-ethanonaphtho[1,2-h]chromene-3,2'-furan]-6,8,12(2H,9H,12aH)-trione | 16.23 | m/z 485.3 [M + H]$^+$<br>m/z 529.4 [M − H + FA]$^-$ |
| 12 new | (1S,2S,2'S,3'R,4aS,4'S,12aR)-1,3'-dihydroxy-2,4',5',5',10a,12a-hexamethyl-4',5',10,10a-tetrahydro-1H,3'H-spiro[1,4a-ethanonaphtho[1,2-h]chromene-3,2'-furan]-6,8,12(2H,9H,12aH)-trione | 16.58 | m/z 483.2 [M + H]$^+$<br>m/z 527.2 [M − H + FA]$^-$ |
| 13 new | (2S,3S,3'R,4R,4aR,4'S,10bS)-3'-hydroxy-8-methoxy-3,4a,4',5',5',7-hexametnyl-4,4a,4',5'-tetrahydro-3H,3'H-spiro[4,10b-ethanobenzo[h]chromene-2,2'-furan]-5,6-dione | 20.07 | m/z 429.5 [M + H]$^+$<br>m/z 427.4 [M − H]$^-$ |
| 14 | Blazeispirol C<br>CAS RN: 348111-16-0 | 22.66 | m/z 401.2 [M + H]$^+$ |

FA = Formic acid

* Given retention time from isolated pure compounds. Minor changes in retention time in extracts possible.

Example 3

Structure Determination a. Atom Numbering for Terpenoid Spiro Ketal Compounds Atom numbering for literature-known compounds and novel compounds was done as proposed by Hirotani et al (*Tetrahedron Lett.* (2000) 41: 5107-5110).

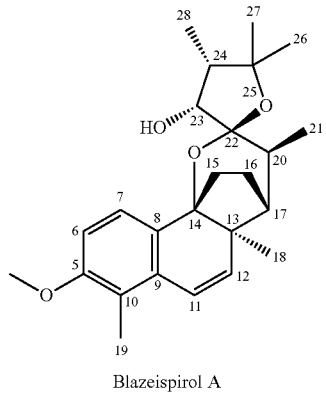

Blazeispirol A

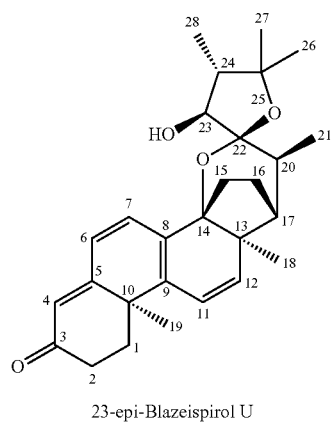

23-epi-Blazeispirol U b. Identification of Literature-Known Compounds

The structure of Blazeispirol A was determined according to Hirotani et al. (Tetrahedron Lett (1999) 40: 329-332) Structures of Blazeispirols C and E were determined according to Hirotani et al. (*Tetrahedron* (2002) 58: 10251-10257). Structure of Blazeispirol D was determined according to Hirotani et al. (*Tetrahedron Lett* (2000) 41: 6101-6104). Structure of Blazeispirol X was determined according to Hirotani et al. (*Tetrahedron Lett* (2000) 41: 6101-6104).

c. Identification of Novel Compounds

Generally, the novel compounds were identified by means of 1D and 2D NMR spectroscopy in conjunction with high resolution ESI-MS data and interpretation of UV spectra and retention times. The minimum NMR dataset consisted of $^1$H, $^1$H, $^1$H-gCOSY, $^1$H, $^{13}$C-gHSQC, and $^1$H, $^{13}$C-gHMBC NMR spectra. Carbon chemical shifts were deduced from the two dimensional heteronuclear spectra. In certain cases additional data like $^{13}$C and $^1$H, $^1$H-NOESY NMR spectra were obtained. All molecular formulae were confirmed by high resolution ESI-MS data using sodium formate as internal reference and allowing for 3 ppm as maximum experimental deviation.

Compounds 5, 9, 10, 11, and 12 all showed oxidation patterns and double bond positioning which clearly deviated from all literature-known terpenoid spiro ketal compounds. Some similarity was found to blazeispirol U. However, for structure elucidation a thorough and complete de novo interpretation of 1D and 2D NMR data was done. Connectivities were established on basis of these experiments. Stereochemical assignments were based on chemical shift comparison with known blazeispirol derivatives and NOE interpretation. The complete assignment of NMR data is given in Table 4.

Compound 6 (23-epi-Blazeispirol U) was identified by comparison with NMR data for blazeispirol U (Hirotani et al, *Phytochemistry* (2002) 61: 589-595). The NMR data of both compounds are in agreement with exception of signals of the 5-membered heterocycle. Here, the scalar coupling constant of the two methine protons differs: whereas $^3J_{HH}$=5.0 Hz are reported for blazeispirol U, the present structure exhibits a coupling constant of $^3J_{HH}$=10.6 Hz. This indicates a change from a cis-configuration to a trans-configuration of these two protons at C-23 and C-24. 2D $^1$H, $^1$H-NOESY NMR data interpretation showed the spatial proximity of 23-H and both 20-H and 21-H$_3$, while the 24-CH$_3$ (atom no. 28) group did not show a comparable NOE signal. These findings proof the epimerization at C-23 as compared with blazeispirol U. Hence, the compound was identified as 23-epi-Blazeispirol U.

Compound 7 (17-Hydroxyblazeispirol A) showed similar NMR data as blazeispirol A. The hydroxylation in position 17 was indicated by the missing methine proton while an additional quaternary, oxygenated carbon atom was found ($\delta_C$=83.2). Its position at C-17 was obvious from $^3J_{CH}$ HMBC correlations to the methyl groups at position 18 and 21, respectively. Consequently, the neighbored carbon atoms of C-17 face a slight downfield shift in their carbon NMR data due to the electron withdrawing effect of the oxygen atom.

Compound 8 (12-Oxoblazeispirol C) was identified by comparison with data of blazeispirol C. While most NMR signals equal each other, the obvious difference was the existence of a carbonyl group. Its chemical shift ($\delta_C$=212.0) indicated the keto functionality while the localisation at C-12 was unequivocally identified by HMBC correlations with 18-H$_3$ and 11-H$_2$. The relative configuration of the compound was found identical to blazeispirol C as shown by respective 2D NOESY correlations.

Compound 13 (11,12-Dioxoblazeispirol C) was characterized by comparison of its NMR data with corresponding data of compound 8 (12-Oxoblazeispirol C). The second carbonyl moiety at C-11 was identified by the altered chemical shift of C12=O ($\delta_C$=197.2 instead of $\delta_C$=212.0) and $^4J_{CH}$ HMBC correlations to C11=O ($\delta_C$=183.8) from 17-H and 19-H$_3$.

TABLE 3

HR-ESIMS data of novel compounds.

| Cmpd. number | Name | Molecular formula | m/z, measured | m/z, calculated for [M + H]$^+$ |
|---|---|---|---|---|
| 5 new | (14β,22S,23R)-14,22:22,25-Diepoxy-23-hydroxy-ergosta-4,7,9-triene-3,6-dione | C$_{28}$H$_{36}$O$_5$ | 453.2640 | 453.2636 |
| 6 new | 23-epi-Blazeispirol U | C$_{28}$H$_{36}$O$_4$ | 437.2684 | 437.2686 |
| 7 new | 17-Hydroxyblazeispirol A | C$_{25}$H$_{34}$O$_5$ | 415.2480 | 415.2479 |
| 8 new | 12-Oxoblazeispirol C | C$_{25}$H$_{24}$O$_4$ | 415.2487 | 415.2479 |
| 9 new | (1R,2S,2'S,3'R,4aS,4'S,10aR,12R,12aS)-3',12-dihydroxy-2,4',5',5',10a,12a-hexamethyl-4',5',10,10a,12,12a-hexahydro-1H,3'H-spiro[1,4a-ethanonaphtho[1,2-h]chromene-3,2'-furan]-6,8(2H,9H)-dione | C$_{28}$H$_{36}$O$_6$ | 469.2576 | 269.2585 |
| 10 new | (1R,2S,2'S,3'R,4aS,4'S,12aS)-3',12-dihydroxy-2,4',5',5',10a,12a-hexamethyl-4',5',6a,7,10,10a,12,12a-octahydro-1H,3'H-spiro[1,4a-ethanonaphtho[1,2-h]chromene-3,2'-furan]-6,8(2H,9H)-dione | C$_{28}$H$_{38}$O$_6$ | 471.2750 | 471.2741 |
| 11 new | (1R,2S,2'S,3'R,4aS,4'S,12aR)-3',6a-dihydroxy-2,4',5',5',10a,12a-hexamethyl-4',5',6a,7,10,10a-hexahydro-1H,3'H-spiro[1,4a-ethanonaphtho[1,2-h]chromene-3,2'-furan]-6,8,12(2H,9H,12aH)-trione | C$_{28}$H$_{36}$O$_7$ | 485.2535 | 485.2534 |
| 12 new | (1S,2S,2'S,3'R,4aS,4'S,12aR)-1,3'-dihydroxy-2,4',5',5',10a,12a-hexamethyl-4',5',10,10a-tetrahydro-1H,3'H-spiro[1,4a-ethanonaphtho[1,2-h]chromene-3,2'-furan]-6,8,12(2H,9H,12aH)-trione | C$_{28}$H$_{34}$O$_7$ | 483.2379 | 483.2377 |
| 13 new | (2S,3S,3'R,4R,4aR,4'S,10bS)-3'-hydroxy-8-methoxy-3,4a,4',5',5',7-hexamethyl-4,4a,4',5'-tetrahydro-3H,3'H-spiro[4,10b-ethanobenzo[h]chromene-2,2'-furan]-5,6-dione | C$_{25}$H$_{32}$O$_6$ | 427.2121 | 427.2126 for [M − H]$^-$ |

TABLE 4

NMR data of novel compounds. Data were obtained in CDCl$_3$ at 300 K on a Bruker Avance NMR spectrometer operating at 500 MHz proton frequency. $^{13}$C chemical shifts were taken from HSQC and HMBC spectra.

| | Compound 5 | | | | | | | |
|---|---|---|---|---|---|---|---|---|
| Atom | $^{13}$C | $^1$H, mult. | $^{13}$C | $^1$H, mult. | $^{13}$C | $^1$H, mult. | $^{13}$C | $^1$H, mult. |
| 1 | 34.9 | 2.23, 2.40, m | | | | | | |
| 2 | 34.9 | 2.4, 2.61, m | | | | | | |
| 3 | n.d. | — | | | | | | |
| 4 | 126.7 | 6.50, s | | | | | | |
| 5 | 156.9 | — | | | | | | |
| 6 | 187.0 | — | | | | | | |
| 7 | 122.3 | 6.41, s | | | | | | |
| 8 | n.d. | — | | | | | | |
| 9 | 138.8 | — | | | | | | |
| 10 | 39.3 | — | | | | | | |
| 11 | 130.6 | 6.13, m | | | | | | |
| 12 | 36.2 | 2.06, 2.40, m | | | | | | |
| 13 | 46.6 | — | | | | | | |
| 14 | 83.6 | — | | | | | | |
| 15 | 37.3 | 1.83, 2.34, m | | | | | | |
| 16 | 23.2 | 1.81, 2.16, m | | | | | | |
| 17 | 50.6 | 1.77, m | | | | | | |
| 18 | 16.8 | 0.98, s | | | | | | |
| 19 | 30.0 | 1.46, s | | | | | | |
| 20 | 33.8 | 2.54, m | | | | | | |
| 21 | 16.9 | 1.12, d | | | | | | |
| 22 | 108.0 | — | | | | | | |
| 23 | 85.4 | 3.94, d | | | | | | |
| 24 | 44.2 | 2.51, m | | | | | | |
| 25 | 85.3 | — | | | | | | |
| 26 | 25.9 | 1.15, s | | | | | | |
| 27 | 31.3 | 1.35, s | | | | | | |
| 28 | 8.9 | 1.00, d | | | | | | |
| OMe | — | — | | | | | | |

| | Compound 6 | | Compound 7 | | Compound 8 | | Compound 9 [1] | |
|---|---|---|---|---|---|---|---|---|
| Atom | $^{13}$C | $^1$H, mult. | $^{13}$C | $^1$H, mult. | $^{13}$C | $^1$H, mult. | $^{13}$C | $^1$H, mult. |
| 1 | 31.6 | 2.01, 2.31, m | — | — | — | — | 33.4 | 2.15, 2.41, m |
| 2 | 32.9 | 2.53, 2.53, m | — | — | — | — | 33.8 | 2.42, 2.71, m |
| 3 | 197.7 | — | — | — | — | — | 199.0 | — |
| 4 | 123.6 | 5.83, s | — | — | — | — | 125.4 | 6.17, s |
| 5 | 165.2 | — | 156.3 | — | 156.7 | — | 136.6 | — |
| 6 | 124.6 | 6.27, d | 108.9 | 6.74, d | 108.8 | 6.83, d | 186.5 | — |
| 7 | 128.6 | 6.69, d | 121.3 | 7.22, d | 123.4 | 7.37, d | 120.9 | 6.18, s |
| 8 | 130.0 | — | 131.4 | — | 131.2 | — | 155.9 | — |
| 9 | 138.0 | — | 130.1 | — | 129.5 | — | 155.4 | — |
| 10 | 37.9 | — | 122.4 | — | 124.0 | — | 38.6 | — |
| 11 | 119.6 | 6.08, d | 122.9 | 6.63, d | 38.8 | 3.35, 3.67, d | 136.8 | 6.09, d |
| 12 | 142.0 | 5.95, d | 134.5 | 6.35, d | 212.0 | — | 68.6 | 4.31, m |
| 13 | 47.6 | — | 49.4 | — | 57.8 | — | 53.6 | — |
| 14 | 82.9 | — | 83.3 | — | 83.5 | — | 82.8 | — |
| 15 | 36.2 | 1.73, 2.62, m | 34.7 | 1.79, 2.36, m | 38.1 | 1.42, 2.47, m | 36.4 | 1.70, 2.22, m |
| 16 | 24.5 | 1.37, 2.01, m | 32.2 | 1.35, 2.31, m | 20.4 | 1.61, 2.01 | 21.9 | 1.73, 2.00, m |
| 17 | 48.4 | 1.96, m | 83.2 | 2.47, m | 44.3 | 2.47, m | 46.0 | 2.03, m |
| 18 | 13.6 | 0.98, s | 12.9 | 0.82, s | 13.3 | 0.95, s | 10.2 | 0.84, s |
| 19 | 27.0 | 1.32, s | 10.9 | 2.21, s | 11.5 | 2.10, s | 28.3 | 1.39, s |
| 20 | 31.8 | 2.39, m | 40.0 | 2.47, m | 33.5 | 2.47, m | 32.3 | 2.47, m |
| 21 | 13.7 | 0.90, d | 10.7 | 1.22, d | 16.5 | 1.17, d | 16.2 | 1.04, d |
| 22 | 103.8 | — | 107.5 | — | 107.3 | — | 108.3 | |
| 23 | 79.3 | 3.41, d | 84.6 | 3.98, d | 85.4 | 3.96, m | 82.6 | 3.74, d |
| 24 | 46.3 | 2.01, m | 44.4 | 2.63, m | 44.2 | 2.62, m | 43.4 | 2.26, m |
| 25 | 80.6 | — | 84.2 | — | 84.7 | — | 84.2 | — |
| 26 | 23.8 | 1.00, s | 25.6 | 1.18, s | 25.7 | 1.17, s | 24.7 | 1.06, s |
| 27 | 29.4 | 1.31, s | 31.0 | 1.41, s | 30.9 | 1.42, s | 30.2 | 1.27, s |
| 28 | 11.3 | 1.06, d | 8.7 | 1.04, d | 8.8 | 1.05, d | 8.6 | 0.92, d |
| OMe | — | — | 55.8 | 3.81, s | 55.8 | 3.82, s | — | — |

| | Compound 10 [1] | | Compound 11 [2] | | Compound 12 [1] | | Compound 13 | |
|---|---|---|---|---|---|---|---|---|
| Atom | $^{13}$C | $^1$H, mult. | $^{13}$C | $^1$H, mult. | $^{13}$C | $^1$H, mult. | $^{13}$C | $^1$H, mult. |
| 1 | 34.0 | 1.65, 2.18, m | 31.2 | 2.27, 2.36, m | 32.5 | 2.27, 2.56, m | — | — |
| 2 | 36.4 | 2.19, 2.42, m | 37.5 | 2.23, 2.62, m | 33.6 | 2.45, 2.80, m | — | — |
| 3 | 208.0 | | 205.6 | — | 198.6 | — | — | — |
| 4 | 39.9 | 2.21, 2.35, m | 50.1 | 2.17, 2.72, m | 126.6 | 6.21, s | — | — |

TABLE 4-continued

NMR data of novel compounds. Data were obtained in CDCl$_3$ at 300 K on a Bruker Avance NMR spectrometer operating at 500 MHz proton frequency. $^{13}$C chemical shifts were taken from HSQC and HMBC spectra.

| | | | | | | | | |
|---|---|---|---|---|---|---|---|---|
| 5  | 53.7  | —       | 81.3  | —       | 153.6 | —       | 156.9 | -       |
| 6  | 198.4 | —       | 198.5 | —       | 186.3 | —       | 115.5 | 7.20, d |
| 7  | 118.0 | 5.81, s | 123.3 | 6.40, s | 127.0 | 6.50, s | 123.1 | 7.55, d |
| 8  | 153.9 | —       | 153.4 | —       | 152.5 | —       | 138.8 | —       |
| 9  | 133.6 | —       | 155.0 | —       | 154.8 | —       | 128.0 | —       |
| 10 | 38.7  | —       | 45.7  | —       | 39.5  | —       | 131.3 | —       |
| 11 | 136.2 | 6.02, d | 125.6 | 6.31, s | 124.6 | 6.38, s | 183.8 | —       |
| 12 | 68.8  | 4.33, m | 201.7 | —       | 205.7 | —       | 197.7 | —       |
| 13 | 52.9  | —       | 58.9  | —       | 57.6  | —       | 60.2  | —       |
| 14 | 82.4  | —       | 83.3  | —       | 81.4  | —       | 81.5  | —       |
| 15 | 35.4  | 1.82, 2.18, m | 35.2 | 1.70, 2.18, m | 34.4 | 1.88, 2.36, m | 42.5 | 1.48, 2.75, m |
| 16 | 21.8  | 1.75, 2.01, m | 21.8 | 1.48, 1.97, m | 28.3 | 1.24, 2.22, m | 21.4 | 1.64, 2.09, m |
| 17 | 45.8  | 2.02, m | 45.6  | 2.36, m | 81.4  | —       | 44.8  | 2.53, m |
| 18 | 10.3  | 0.80, s | 14.9  | 1.08, s | 11.9  | 1.05, s | 13.6  | 1.07, d |
| 19 | 26.4  | 1.23, s | 24.8  | 1.26, s | 28.5  | 1.51, s | 12.4  | 2.59, s |
| 20 | 32.4  | 2.46, m | 33.7  | 2.60, m | 38.5  | 2.53, m | 33.4  | 2.53, m |
| 21 | 16.1  | 1.04, d | 16.3  | 1.17, d | 9.6   | 1.07, s | 15.3  | 1.17, s |
| 22 | 107.8 | —       | 109.0 | —       | 108.4 | —       | 107.0 | —       |
| 23 | 82.6  | 3.72, m | 84.5  | 4.01, m | 82.7  | 3.83, m | 84.1  | 4.05, m |
| 24 | 43.3  | 2.23, m | 44.9  | 2.46, m | 43.5  | 2.31, m | 43.6  | 2.59, m |
| 25 | 83.8  | —       | 85.6  | —       | 84.9  | —       | 84.6  | —       |
| 26 | 24.7  | 1.06, s | 24.9  | 1.15, s | 24.6  | 1.08, s | 24.8  | 1.16, s |
| 27 | 30.3  | 1.26, s | 30.8  | 1.32, s | 30.2  | 1.26, s | 29.9  | 1.41, s |
| 28 | 8.7   | 0.91, d | 8.9   | 1.02, d | 8.7   | 0.94, d | 8.2   | 1.05, d |
| OMe| —     | —       | —     | —       | —     | —       | 55.1  | 3.90, s |

$^{1)}$ NMR spectra obtained in DMSO-d$_6$ at 300 K
$^{2)}$ NMR spectra obtained in acetone-d$_6$ at 273 K Example 4

Biological Evaluation

A) In Vitro Assay with LXR (Liver X Receptor)
Assay Description:

The LXR assay is configured using time-resolved fluorescence resonance energy transfer technology (HTR-FRET) (see Albers et al., *J. Biol. Chem.* 2006 24; 281(8) 4920-30; Chin J, *Assay Drug Dev. Technol.* 2003 1(6):777-87).

In the presence of an agonist, a fusion protein of glutathione S-transferase (GST) and LXR ligand binding domain (GST-LXR LBD) associates with a biotin-labeled nuclear receptor coactivator (b-SRC1). A fluorescent signal is detected in the presence of Eu-labeled anti GST antibodies and streptavidin-labeled allophycocyanin (APC). FRET is made possible by agonist-dependent close interaction of the test proteins.

Compounds which act as agonists at the LXR ligand binding domain were detected by an increase in time-resolved fluorescence. This LXR-FRET was performed as described by Albers et al. (loc. cit.).

FRET-active compounds were assayed in a FRET 12-point dose response experiment to determine the EC50—values of the compounds mentioned in the following Table 5.

TABLE 5

EC$_{50}$ values for LXRα & LXβ

| Cmpd. number | Name | EC50 LXRα [μM] | EC50 LXRβ [μM] |
|---|---|---|---|
| 1 | Blazeispirol A | 1.4 | 25 |
| 3 | Blazeispirol E | 11 | 24 |
| 2 | Blazeispirol D | 1.1 | 5.5 |
| 6; new | 23-epi-Blazei-spirol U | 5.5 | 14 |
| 7; new | 17-Hydroxy-blazeispirol A | 31 | 34 |
| 8; new | 12-Oxo-blazeispirol C | 24 | 31 |
| 9; new | | 1.0 | 4.6 |
| 5; new | | 7.6 | 24 |

In Vivo
Study Design

An animal study is performed to prove efficacy (e.g. blood lipid lowering effects) of the compounds of the invention (e.g. *Agaricus subrufescens* extract) according to example 1c in a feeding model of weight gain, blood lipid and body composition.

For this purpose at least four groups of approx. 8 weeks old rats e.g. Sprague Dawley rats, preferably male rats (e.g. purchased from CHARLES RIVERS LABORATORIES, Sulzfeld, Germany) are fed for an assimilation phase, preferable a few days up to two weeks, with standard diet (SD, e.g. purchased from ssniff Spezialdiäten GmbH, 59494 Soest, Germany). A first treatment group thereafter is fed with cholesterol supplemented (e.g. 0.1% cholesterol w/w) high fat (HF) at least 4 weeks, more preferred up to ten weeks. A second treatment group is fed with standard diet (SD) for the whole time. Two further groups are used as control group and fed with both diets without administration of the extract. Each group contains 8-12 rats. Food and water consumption are recorded at least five days per week. The body weight is measured throughout the study at least once per week.

Lean mass, fat mass, and/or blood lipids are assessed shortly before extract application (e.g. one day before), at the mid-point and at the end-point of this study. While control groups do receive the diet and a suitable vehicle (preferably food-grade oils) only, the treatment groups do receive the above mentioned extract once daily preferably in a dosage of 100 mg/kg body weight via oral gavages within the two dietary backgrounds (HF and SD). The aim is to demonstrate a positive effect of the test items on body weight, body composition, body fat distribution and/or blood lipids/cholesterol. Clinical blood parameters are determined in accordance with standard procedures. The following parameters are determined: HDL-cholesterol, LDL-cholesterol, total cholesterol, glucose, triglyceride, AP (alkaline phosphatase), ALT (aspartate aminotransferase), AST (alanine aminotransferase), bilirubin total, urea, creatinkinase, protein total, albumin, sodium, potassium, chloride, and calcium. All animals are handled regularly, and in case pathological signs appear, they are recorded with special regard to haematological data, behaviour, body weight development, food consumption, skin, urine- and faecal excretion, condition of body orifices and any signs of illness.

A typical protocol is outlined below in detail:

The room temperature is maintained at 22±3° C. and the relative humidity is kept at 60%±15%. The light/dark period is 12/12 hours.

During the acclimatization period all animals receive standard rat low fat diet (S2602-E010) produced by ssniff Spezialdiäten GmbH (Experimental Animal Diets, 59494 Soest, Germany). From the beginning of the test item administration, 10 animals receive standard rat diet (group 1). 20 animals receive high fat diet (10 rats in group 2, 10 rats in control group) and (S2602-E020) produced by ssniff Spezialdiäten GmbH. Food consumption is controlled and recorded on a daily basis (from Monday to Friday).

Drinking tap water is continuously available ad libitum via drinking bottles. Consumption is controlled on a daily basis (from Monday to Friday). Drinking water is examined according to the German Regulations on Drinking Water 2001 (*Deutsche Trinkwasserverordnung* 2001) by Berliner Wasserbetriebe.

All test items are orally delivered to individuals under light anaesthesia by an gavage catheter applied by the animal supplier.

The vehicle is composed from 10% (v/v) DMSO (Fisher Scientific D/4121/PB15), 10% (v/v) Cremophor EL (Sigma C5135), 70% (v/v) Saline (0.9% NaCl) and 10% (v/v) HPMC solution (SIGMA H7509). For test purposes the DMSO solution contains the active component. The total dose of active component is 100 mg/kg body weight.

The individual body weight of all animals involved in the study are recorded on animal arrival at animal test site, before start of in-life phase, and twice a week over a time period of 8 weeks.

As the individual body weight is expected not to remain constant over the 8 weeks time period, the individual dose shall be adapted accordingly to the observed body weight in two-week time intervals. Body weights are recorded twice a week.

All animals are handled regularly, and in case pathological signs appear, they are recorded with special regard to haematological data, behaviour, body weight development, food consumption, skin, urine- and faecal excretion, condition of body orifices and any signs of illness and a score including: activity, lethargy, (auto-) aggression, death, injury, cramping, tremor, abnormal, gait, motor coordination, scratching, piloerection, fur, skin, mucosal membranes, eyes, respiration.

For blood sampling from the tail vein or by heart puncture, animals are shortly kept under isoflurane anaesthesia. Approx. 500 µl of EDTA supplemented blood as well as 250 µl serum are collected from each animal after acclimatization period but prior to substance administration, approx. four weeks after first test item dosing and at terminal sacrifice.

All samples are transferred on crushed ice to the haematological test site via courier within one hour. The blood samples vials are labeled with a bar code.

At terminal sacrifice, an additional blood sample (serum, 5 ml) is collected for metabolite analysis. The blood samples are stored at −80° C.

All animals are terminated 8 weeks after first test item dosing using overdose of anaesthetics Ketamin and Rompun. The following organs are collected and stored in formalin for later evaluations:

lung, heart, liver, kidney, spleen, brain, intestine, stomach, muscle and testicle.

All terminated animals are subject of extensive pathological examinations with special regard on organ toxicity.

Haematology and Clinical Chemistry

Differential blood count is determined using a Sysmex XT2000i counter according to the manufacturer's instructions. Clinical parameters are determined in accordance with standard procedures. The following parameters are determined: HDL-cholesterol, LDL-cholesterol, glucose, cholesterol, triglyceride, AP, ALT, AST, bilirubin total, urea, creatinkinase, protein total, albumin, sodium, potassium, chloride, and calcium.

Body Fat Measurement

Dual-energy X-ray absorptiometry (DXA) are performed at the radiology test site to measure rodent body fat contents. Animals are scanned in a Lunar Prodigy Advance™ device (GE Healthcare) controlled by software 13.4 version (running in the small animals modus). The animals are anaesthetised or sacrificed (terminal measurement) before scanning and placed with their stomach down in the Prodigy device. A dead animal are included in all the scans as an internal standard to avoid interscan variations. DXA is performed: after acclimatization period but prior to substance administration, approx. four weeks after first test item dosing and at terminal sacrifice.

Example 5

Phylogenetic Examination of Species of the Genus *Agaricus*

The sequences were generated as described by Bitzer et al. (Mycological Res. (2008) 112: 251-270. The nucleic acid codes are according the rules of the Nomenclature Committee of the International Union of Biochemistry and Molecular Biology (NC-IUBMB) known in the art (http://www.chem.qmul.ac.uk/iubmb/misc/naseq.html).

The ITS1 nr DNA sequences are defined by their beginning at the codons "ttg aat" and their end codons "gaa aat".

The following sequences (given in the one-letter-code) are used:

```
                                                            SEQ ID NO: 1
ttgaattatg tttctagata ggttgtagct ggctctttag agcatgtgca cgcctgtttg gacttcattt tcatccacct gtgcacctat tgtagtcttt ggttgggtta ggaggaagtg gtcattgtgt cagcatctgc tggatgtgag gatttgcatt gtgaaagctt tgctgtcctt gatgtgatca tggaatctct ttctcactag agtctatgtc actcattata ctctgtcgaa tgtcattgaa tgtctttaca tgggcttgta tgcctatgaa aat (283)

SEQ ID NO: 2
ttgaattatg tttctagata ggttgtagct ggctctttag agcatgtgca cgcctgtttg gacttcattt tcatccacct gtgcacctat tgtagtcttt ggttgggtta ggaggaagtg gtcattgtgt cagcatctgc tggatgtgag gatttgcatt gtgaaagctt tgctgtcctt gatgtgatca tggaatctct ttctcactag agtctatgtc actcattata ctctgtcgaa tgtcattgaa tgtctttaca tgggcttgta tgcctatgaa aat (283)

SEQ ID NO: 3
ttgaattatg tttctagatg ggttgtagct ggctctttag agcatgtgca cgcctgtttg gacttcattt tcatccacct gtgcacctat tgtagtcttt ggttgggtta ggaggaagtg gtcattgtgt cagcatctgc tggatgtgag gacttgcatt gtgaaagctt tgctgtcctt gatgtgatca tggaatctct ttctcactag agtctatgtc actcattata ctctgtcgaa tgtcattgaa tgtctttaca tgggcttgta tgcctatgaa aat (283)

SEQ ID NO: 4
ttgaattatg tttctaaatg ggttgtagct ggctctttag agcatgtgca cgcctgtttg gacttcattt tcatccacct gtgcacctat tgtagtcttt ggttgggtta ggaggaagtg gtcatcctat cagcatctgc tggatgtgag gacttgcatt gtgaaaactt tgctgtcctc tatgtgatca tgaaatcact ttctcaccgg agtctatgtc attcattata ctctgtcgaa tgtcattgaa tgtctttaca tgggcttgta tgcctatgaa aat (283)
```

A: Phylogenetic Tree of Selected Sequences.

The dendrogram was performed with the program MegAlign™ as part of the Lasergene® Suite (trademarks of DNAStar Inc., Madison, USA;) for Windows 32 Version 3.16 using the method Clustal. The parameter settings for DNA sequence comparison were as follows: Pairwise Alignment Parameters: Ktuple 2; Gap Penalty 5, Window 4, Diagonals Saved 4; Multiple Alignment Parameters: Gap Penalty 10, Gap Length Penalty 10. Reference sequences used in this study were downloaded from GenBank (13 Aug. 2010) and the respective ITS 1 nr DNA sequences were identified by their begin and end codons as described above.

The results were presented in FIG. 3. As discussed in detail above the data clearly indicate that strain ATCC34722 and the strain coded with the acc. No AY484674 were out-group strains, supposedly misidentified as *A. subrufescens*.

The DNA sequence coded with the acc. No AJ133375, however, was found to be among the "in group" strains. However, this DNA sequence (AJ133375) appeared dubious, because it was assigned by the depositors to *A. sylvaticus*, a fungus belonging to a different section of the genus *Agaricus*, which is not deemed closely related to sect. Arvenses and thus, the species *A. subrufescens* sensu Kerrigan (2005). Therefore, the phylogenetic position of this sequence was verified by using two specimens of authentic *A. sylvaticus* collected in Europe.

*A. sylvaticus* STMA10083 was collected in a forest of *Picea abies* in Germany, Rheinland-Pfalz, near Bad Dürkheim, 500 m from the restaurant "Saupferch", on 29 Aug. 2010. *A. sylvaticus* STMA10072 was collected in the United Kingdom, Scotland, Aberdeenshire, Morrone Birchwood, on 8 Aug. 2010 during the post-conference foray of the International Mycological Congress (IMC9).

Both specimens of *Agaricus sylvaticus* are deposited in the public herbarium of the Staatliches Museum für Naturkunde, Karlsruhe, Germany and can be obtained from there on loan. They were determined using the key in Horak E. (2005): Rohrlinge and Blätterpilze in Europa, Bestimmungsbuch, Elsevier, Spektrum Akademischer Verlag, München, p. 242-250. As can be seen in the phylogenetic tree (FIG. 3), both specimens gave DNA sequences highly similar to one another, but both of these DNA sequences were quite different from that of *A. subrufescens*. Therefore, it is concluded that the specimen from which the reference DNA sequence Acc. No. AJ133375 was derived was either misidentified, or the sequence data deposited in GenBank under Acc. No. AJ133375 were actually derived from a different strain, which possibly also belongs to *A. subrufescens* sensu Kerrigan (2005).

TABLE 6

Strains used for the phylogenetic tree, compare FIG. 3

| Entry | accession number, identifier | description |
|---|---|---|
| 1 | AY484697 | *Agaricus blazei* strain WC837 |
| 2 | FR694900* | FU 70033, *A. subrufescens*, MUCL 52948 |
| 3 | FR694899* | ATCC76739, *A. blazei*, MUCL 52949 |
| 4 | AY818659 | *Agaricus subrufescens* isolate H1X1 |
| 5 | AJ133375 | "*Agaricus sylvaticus*" |
| 6 | AY818654 | *Agaricus subrufescens* isolate BS1 |
| 7 | AY818660 | *A. subrufescens* I_101_S1 |
| 8 | AY818646 | *A subrufescens* DEH513 |
| 9 | AY818649 | *Agaricus rufotegulis* |
| 10 | FR694898* | MUCL 44605, *A. subrufescens*, MUCL 52947 |
| 11 | AY818656 | *Agaricus subrufescens* isolate SBRF |
| 12 | AY484690 | *Agaricus arvensis* strain WC848 |
| 13 | AY484674 | "*Agaricus subrufescens*" W17 |
| 14 | FR694901* | "*Agaricus subrufescens*" ATCC34722 |
| 15 | AY484686 | *Agaricus macrocarpus* |
| 16 | AY484672 | *Agaricus augustus* |

TABLE 6-continued

Strains used for the phylogenetic tree, compare FIG. 3

| Entry | accession number, identifier | description |
|---|---|---|
| 17 | FR694902* | *Agaricus sylvaticus* STMA 10083 <SEQ ID No: 5> |
| 18 | FR694903* | *Agaricus sylvaticus* STMA 10072 <SEQ ID No: 6> |

The sequences marked with an asterisk i.e. entry 2, 3, 10, 14, 17 and 18 were sent to GenBank for the first time.

B: Sequence Alignment and Comparison of MUCL 52948, MUCL 52947 and MUCL 52949

The alignments of *A. subrufescens* MUCL 52948 (<SEQ ID NO: 1>) with *A. subrufescens* MUCL 52949 (<SEQ ID NO:2>) and *A. subrufescens* MUCL 52947 (<SEQ ID NO: 3>) were performed online using the program nBLAST/megablast (http://blast.ncbi.nlm.nih.gov/Blast.cgi) Version 2.2.24. The parameter settings were: word size 28, expected threshold 10, match/mismatch scores 1,-2, gap costs linear.

Reference sequences used in this study were downloaded from GenBank and the respective ITS 1 nr DNA sequences were identified by their begin and end codons as described above.

The used ITS 1 nr DNA sequences used in this study were identical with those of the previous example.

TABLE 7

Sequence of *A. subrufescens* MUCL 52948 (<SEQ ID NO: 1>) with *A. subrufescens* MUCL 52949 (<SEQ ID NO: 2>) and *A. subrufescens* MUCL 52947 (<SEQ ID NO: 3>) and the most genuine sequences of GenBank (in-group)

| Entry | accession number, identifier | description | Max ident |
|---|---|---|---|
| 1 | MUCL 52949 | <SEQ ID NO: 2> | 100.00% |
| 2 | MUCL 52947 | <SEQ ID NO: 3> | 99.29% |
| 3 | AY818646 | *Agaricus subrufescens* isolate DEH513 | 99.62% |
| 4 | AY818649 | *Agaricus rufotegulis* | 99.65% |
| 5 | AY818654 | *Agaricus subrufescens* isolate BS1 | 97.88% |
| 6 | AY818656 | *Agaricus subrufescens* isolate SBRF | 97.53% |
| 7 | AY818659 | *Agaricus subrufescens* isolate H1X1 | 97.53% |
| 8 | AY818660 | *Agaricus subrufescens* isolate I_101_S1 | 99.29% |
| 9 | AY484697 | *Agaricus blazei* strain WC837 | 100.00% |

TABLE 8

Comparison of *A. subrufescens* MUCL 52948 (<SEQ ID NO: 1>), *A. subrufescens* MUCL 52949 (<SEQ ID NO: 2>) and *A. subrufescens* MUCL 52947 (<SEQ ID NO: 3>) against *A. subrufescens* ATCC34722 (<SEQ ID NO: 4>) (out-group)

| Entry | | accession number | description | Max ident |
|---|---|---|---|---|
| 1 | MUCL 52948 | AY484672 | *Agaricus augustus* strain WC4 | 95.77 |
| 2 | | AY484686 | *Agaricus macrocarpus* | 93.31 |
| 3 | | AY484690 | *Agaricus arvensis* strain WC848 | 93.64 |
| 4 | | AY484674 | *Agaricus subrufescens* W17 | 93.64 |
| 5 | MUCL 52949 | AY484672 | | 95.77 |
| 6 | | AY484686 | | 93.31 |
| 7 | | AY484690 | | 93.64 |
| 8 | | AY484674 | | 93.64 |
| 9 | MUCL 52947 | AY484672 | | 96.48 |
| 10 | | AY484686 | | 94.01 |
| 11 | | AY484690 | | 94.35 |
| 12 | | AY484674 | | 94.35 |
| 13 | ATCC34722 | AY484672 | | 99.29 |
| 14 | | AY484686 | | 97.88 |
| 15 | | AY484690 | | 95.76 |
| 16 | | AY484674 | | 98.23 |

C: Sequence Comparison with Databases

According to the widely used and well established FASTA analysis (Mackey et al., Mol Cell Proteomics (2002) p 139-147) the obtained ITS 1 sequences of the *A. subrufescens* MUCL 52948, MUCL 52949 and MUC 52946 were checked for homology to published sequence data. The comparison was performed online using the program FASTA (http://www.ebi.ac.uk; European Bioinformatics Institute, Wellcome Trust Genome Campus, Hinxton, Cambridge, CB10 1SD, UK) Version 35.04 (20 Feb. 2010). The parameter settings were set to default which were defined as follows Gap extension penalty: −4, Open gap penalty: −14, Word size: 6, Expectation upper value limit: 10, Strand: both, Filter: none, Statistical estimates: regress.

Tables 9-11 show the results of the FASTA searches for each individual strain which were performed on 13 Aug. 2010 and present the 8 most genuine DNA sequences deposited with GenBank and some representative (including the most similar as entry 9) sequences referring to other species than *Agaricus subrufescens* as mentioned in this invention and defined above.

TABLE 9

FASTA homology of *Agaricus subrufescens* MUCL 52948 (<SEQ ID NO: 1>) against GenBank (13 Aug. 2010)

| Entry | accession | description | identity | similarity |
|---|---|---|---|---|
| 1 | AY484697 | *Agaricus blazei* strain WC837 | 100.0 | 100.0 |
| 2 | AY818660 | *Agaricus subrufescens* isolate I_101_S1 | 99.3 | 100.0 |
| 3 | AY818654 | *Agaricus subrufescens* isolate BS1 | 97.9 | 100.0 |
| 4 | AY818649 | *Agaricus rufotegulis* | 99.6 | 99.6 |
| 5 | AJ133375 | *Agaricus sylvaticus* | 99.6 | 99.6 |
| 6 | AY818656 | *Agaricus subrufescens* isolate SBRF | 97.5 | 99.6 |
| 7 | AY818659 | *Agaricus subrufescens* isolate H1X1 | 97.5 | 99.6 |
| 8 | AY818646 | *Agaricus subrufescens* isolate DEH513 | 99.3 | 99.3 |
| 9 | AY484672 | *Agaricus augustus* strain WC4 | 95.8 | 95.8 |
| 10 | AY484686 | *Agaricus macrocarpus* | 93.6 | 93.6 |
| 11 | AY484690 | *Agaricus arvensis* strain WC8 | 93.6 | 93.6 |
| 12 | AY484674 | *Agaricus subrufescens* W17 | 93.3 | 93.3 |

TABLE 10

FASTA homology of *Agaricus subrufescens* MUCL 52947 (<SEQ ID NO: 3>) against GenBank (13 Aug. 2010)

| Entry | accession | description | identity | similarity |
|---|---|---|---|---|
| 1 | AY818660 | *Agaricus subrufescens* isolate I_101_S1 | 99.3 | 100.0 |
| 2 | AY818656 | *Agaricus subrufescens* isolate SBRF | 97.9 | 100.0 |
| 3 | AY818649 | *Agaricus rufotegulis* | 99.6 | 99.6 |
| 4 | AY818654 | *Agaricus subrufescens* isolate BS1 | 97.5 | 99.6 |
| 5 | AY484697 | *Agaricus blazei* strain WC837 | 99.3 | 99.3 |
| 6 | AY818646 | *Agaricus subrufescens* isolate DEH513 | 99.3 | 99.3 |
| 7 | AY818659 | *Agaricus subrufescens* isolate H1X1 | 97.2 | 99.3 |
| 8 | AJ133375 | *Agaricus sylvaticus* | 99.2 | 99.2 |
| 9 | AY484672 | *Agaricus augustus* strain WC4 | 96.5 | 96.5 |
| 10 | AY484686 | *Agaricus macrocarpus* | 94.3 | 94.3 |
| 11 | AY484690 | *Agaricus arvensis* strain WC8 | 94.3 | 94.3 |
| 12 | AY484674 | *Agaricus subrufescens* W17 | 94.0 | 94.0 |

TABLE 11

FASTA homology of *Agaricus subrufescens* MUCL 52949 (<SEQ ID NO: 2>) against GenBank (13 Aug. 2010)

| Entry | accession | description | identity | similarity |
|---|---|---|---|---|
| 1 | AY484697 | *Agaricus blazei* strain WC837 | 100.0 | 100.0 |
| 2 | AY818660 | *Agaricus subrufescens* isolate I_101_S1 | 99.3 | 100.0 |
| 3 | AY818654 | *Agaricus subrufescens* isolate BS1 | 97.9 | 100.0 |
| 4 | AY818649 | *Agaricus rufotegulis* | 99.6 | 99.6 |
| 5 | AJ133375 | *Agaricus sylvaticus* | 99.6 | 99.6 |
| 6 | AY818656 | *Agaricus subrufescens* isolate SBRF | 97.5 | 99.6 |
| 7 | AY818659 | *Agaricus subrufescens* isolate H1X1 | 97.5 | 99.6 |
| 8 | AY818646 | *Agaricus subrufescens* isolate DEH513 | 99.3 | 99.3 |
| 9 | AY484672 | *Agaricus augustus* strain WC4 | 95.8 | 95.8 |
| 10 | AY484686 | *Agaricus macrocarpus* | 93.6 | 93.6 |
| 11 | AY484690 | *Agaricus arvensis* strain WC8 | 93.6 | 93.6 |
| 12 | AY484674 | *Agaricus subrufescens* W17 | 93.3 | 93.3 |

Example 6

Animal Study in APOE*3Leiden.CETP Transgenic Mice

The aim of the study was to evaluate the effects of extract IMD-XT0022 (see example 1c) on plasma lipids in female APOE*3-Leiden(E3L).CETP transgenic mice (hereinafter referred to as APOE*3Leiden mice). The effects were compared with phytosterol as a positive control.

APOE*3Leiden mice exhibit elevated plasma cholesterol and triglyceride levels, mainly confined to the VLDL/LDL sized lipoprotein fraction (Havekes L M et al., J. Biol. Chem. 1993; 268: 10540-10545). In contrast to wild-type mice, APOE*3Leiden mice are highly responsive to fat and cholesterol feeding as far as the effects on plasma VLDL and chylomicron levels are concerned (Van Vlijmen B et al., J. Clin. Invest. 1994; 93: 1403-1410, and Groot P H E, et al., Arterioscler. Thromb. Vasc. Biol. 1996; 16: 926-933). In addition, drugs and dietary compounds influencing either the chylomicron and VLDL production and/or the hepatic clearance of lipoproteins exert relatively strong effects on plasma cholesterol and triglyceride levels (e.g. Delsing D J M et al., J. Cardiovasc. Pharmacol. 2003; 42: 63-70). In contrast, in normal wild-type mice the plasma cholesterol and triglyceride levels are very low and (almost) not responsive to diet and hypolipidemic drugs.

This animal model has been proven to be representative for the human situation regarding plasma lipoprotein levels, lipoprotein profiles, its responsiveness to hypolipidemic drugs (like statins, fibrates etc.) and nutrition. In addition, depending on the level of plasma cholesterol, APOE*3Leiden mice develop atherosclerotic lesions in the aorta resembling those found in humans with respect to cellular composition and morphological and immunohistochemical characteristics.

Forty female APOE*3Leiden mice (from the specific pathogen free breeding stock at TNO-Metabolic Health Research, Leiden, Netherlands), 15-16 weeks of age at the start of the experiment were housed during the experiment in Macrolon® cages (maximally 5 animals per cage) in clean-conventional animal rooms (relative humidity 50-60%, temperature about 21° C., light cycle 7 am to 7 pm). Individual mice were marked by ear-punch holes and supplied with food and acidified tap water ad libitum. Dietary ingredients were provided by Hope Farms (Woerden, the Netherlands): The mice received a semi-synthetic modified Western-type diet (WTD) as described by Nishina et al., J. Lipid. Res. 1990:31:859, containing cholesterol (0.1% w/w, final concentration) and saturated fat (15% w/w cacao butter). The animals were put on a Western-type diet with 0.1% cholesterol for 4 weeks (run-in period). After the run-in period, APOE*3Leiden mice were sub-divided into three groups of 10 mice each and treated during 5 weeks with the following compounds: Control group (vehicle gavage, Western-type diet without diet additions), extract group (Western-type diet without diet additions, 100 mg/kg/d extract IMD-XT0022 via daily gavage) or phytosterol group (vehicle gavage, Western-type diet with addition of 1 wt. % of free phytosterol). One week before first administration of IMD-XT0022 mice were gavaged with vehicle to get used to the procedure. Food intake and body weight were measured weekly during the treatment period (t=0, 1, 2, 3, 4 and 5 weeks). After two and five weeks of treatment blood samples were taken after a 4 hour fasting period. After 3 weeks of treatment vehicle Delios V oil (a medium-chain triglyceride oil obtained from BASF Personal Care and Nutrition GmbH, Düsseldorf, Germany) was replaced by Polyethylengycol-400 (PEG-400, Sigma-Aldrich, Steinheim, Germany) for all groups.

Extract IMD-XT0022 was administered daily by oral gavage between 8.00 and 11.00 am CET. In the phytosterol group phytosterol was administered orally as admix to the WTD (1% w/w free phytosterol). The control group and the phytosterol group received the vehicle accordingly. The gavage volume during the treatment period was 10 ml/kg and was adjusted weekly based on the measured body weight of the respective week.

Plasma cholesterol, triglycerides and HDL cholesterol were measured individually at t=0, 2 and 5 weeks. On group level ALT, AST levels and lipoprotein profiles (at t=0 and 5 weeks) were measured. Feces were collected (per cage) during week 5.

On the mornings of the blood sampling time points of t=weeks 2 and t=5 weeks, gavages were not performed between 8.00-11.00 am, but were performed after the blood sampling. At t=5 weeks, 3 days after the last blood sampling, mice were sacrificed after a 4 hour fasting period (and without giving a gavage on the day of sacrifice) by $CO_2$ suffocation. EDTA-plasma was collected via heart puncture and stored at <−70° C. and several organs were collected.

After a 4 weeks run-in period, 10 low-responder mice were removed from the study. The remaining 30 mice where subdivided into 3 groups of 10 mice each, matched for body weight, plasma cholesterol, triglycerides, HDL-cholesterol and age (t=0)

Groups:

| | | |
|---|---|---|
| 1) | Control group | (n = 10) |
| 2) | Treatment group (extract group) (100 mg/kg/d of extract IMD-XT0022) | (n = 10) |
| 3) | Positive control group (phytosterol group) (1 wt. % free phytosterol) | (n = 10) |

Determinations:
  Body weight (week 0, 1, 2, 3, 4 and 5)
  Food intake (per cage, week 0, 1, 2, 3, 4 and 5)
  Plasma total cholesterol, HDL-Cholesterol, and triglycerides (week 0, 2 and 5)
  Lipoprotein profile (cholesterol and phospholipids) at group level (week 0 and 5)
  ALT and AST (liver damage markers) at group level (week 0 and 5)
  Feces collection (per cage, week 5) n=6 samples per group
  Sacrifice after a 4 hour fasting period:
  isolation of heart blood: EDTA-plasma
  collection+weight of: liver, heart, left kidney, spleen, perigonadal fat pads and brain
  collection of: urine & bile
  Determination of liver free cholesterol, liver triglycerides & liver cholesteryl esters (see example 7)

Methods:
  Body weight and food intake measurements were performed by simply weighing the mice weakly and the animal food every 2-3 days.
  Plasma blood samples were obtained after a four-hour fasting period. Animals were placed under a red light heat lamp. Animals were allowed to move freely during blood collection and were not fixed to avoid additional stress. An incision was made in the tail vein to collect tail blood using CB 300 K2E microvettes (Sarstedt, Nümbrecht, Germany) containing EDTA-dipotassium salt. Microvettes containing blood were placed on ice immediately. Plasma was obtained after centrifugation (10 minutes at 6000 rpm) of the samples in a bench-centrifuge at 4° C. Plasma samples (supernatant after centrifugation) were pipetted in an Eppendorf vial and stored at −70° C. for further use.
  Total plasma cholesterol and triglycerides were determined individually in each animal using kits "Cholesterol CHOD-PAP" and "Triglycerides GPO-PAP" both from Roche/Hitachi (Roche Deutschland Holding GmbH, Grenzach-Whylen, Germany), according to the manufacturer's protocol. Measurements were performed in freshly prepared plasma.
  Plasma HDL determination was performed by quantification of cholesterol using kit "Chol CHOD-PAP" from Roche/Hitachi in plasma after precipitation of apoB-containing lipoproteins using $MnCl_2$.
  Measurement of pooled lipoprotein profiles by Fast protein liquid chromatography (FPLC) analysis using a superose column on an AKTA apparatus (GE Healthcare, Bio-Science AB, Uppsala, Sweden). Cholesterol and phospholipid profiles were measured in the fractions using kit "Chol CHOD-PAP" from Roche/Hitachi and kit "phospholipids (B)" from Spinreact St. Esteve d'en bas, Spain). Lipoprotein values are absolute values from cholesterol (mM) and phospholipids (mg/dL) measurements in pooled plasma per group (with 10 mice per group) at t=0 and 5. Fractions 3-8 considered as VLDL; 9-16 as IDL/LDL and 17-23 as HDL.
  Plasma ALT (aspartate aminotransferase) and AST (alanine aminotransferase) were measured in pooled samples using the spectrophotometric assay of the Roche Reflotron system.

Sacrifice
  At t=5 weeks, 3 days after the last blood sampling, mice were sacrificed after a 4 hour fasting period (and without giving a gavage on the day of sacrifice) by $CO_2$ suffocation. EDTA-plasma was collected via heart puncture and stored at <−70° C. The following organs were collected:
  Liver was weighed and cut into 2 pieces and snap frozen in liquid nitrogen and stored at <−70° C. Heart, one kidney, spleen, brain, perigonadal fat pads (on both sides) were all weighed and snap frozen in liquid nitrogen and stored at <−70° C.
  Urine and bile were collected (bladder and gall bladder were not weighed) and snap frozen in liquid nitrogen and stored at <−70° C.
  Gastrointestinal tract was not collected, but was checked for macroscopically visible abnormalities. Any macroscopically visible abnormalities of the tissues were noted down.

Statistical Analysis
  Depending on normality, significance of differences between the groups were calculated either parametrically or non-parametrically, using the computer program SPSS (version 17.0, SPSS Inc., Chicago, Ill., USA). For non-parametric calculations a Kruskall-Wallis test for several independent samples were used, followed by a Mann-Whitney U-test for independent samples. For parametric calculations a One-way ANOVA (Analysis of Variance) for multiple comparisons was used, followed by Dunnett or Bonferroni's correction. For the measured parameters data was normally distributed and therefore the One way ANOVA test was used, followed by Dunnett. A P-value<0.05 was considered statistically significant.

In the following, plasma cholesterol levels and lipoprotein levels are given in detail.

Plasma Cholesterol
  Values given are mean values (i.e. average absolute values±standard deviation) of 10 mice per group.

| | Plasma cholesterol (mM) | | |
|---|---|---|---|
| Group | t = 0 weeks | t = 2 weeks | t = 5 weeks |
| Control group | 11.0 ± 2.0 | 9.9 ± 1.7 | 9.6 ± 2.5 |
| Extract group | 11.0 ± 1.8 | 9.4 ± 2.2 | 7.3 ± 1.4 |
| P-value compared to control group | 0.999 | 0.730 | 0.024 |
| Phytosterol group | 10.9 ± 1.6 | 9.4 ± 1.3 | 8.1 ± 1.8 |
| P-value compared to control group | 0.994 | 0.722 | 0.175 |

After 2 weeks of treatment there were no differences in plasma cholesterol between the different treatment groups as compared to the control group. After 5 weeks of treatment plasma cholesterol was significantly decreased in the extract group as compared to the control group (with 24%, p=0.024), while the plasma cholesterol of the phytosterol group was not significantly decreased, although lower with 16%.

Lipoprotein Profiles

After 5 weeks of treatment (2 weeks after changing vehicle), plasma cholesterol and phospholipid levels decreased in the VLDL peak by both IMD-XT0022 and phytosterol treatment (a decrease in the area under the curve of the VLDL peak of 32% and 25% for cholesterol and 19% and 21% for phospholipid levels for IMD-XT0022 and phytosterol treatment, respectively). For the HDL peak, plasma cholesterol and phospholipids were not affected by any of the treatments. These data are in line with the observed decreases in total plasma cholesterol.

The remaining results are given in short summary below:

Markers of general safety and well-being

No specific clinical signs were observed during the study in the treatment groups Organ weight was not different for liver, heart, left kidney, spleen, perigonadal fat pads and brain between the different treatment groups as compared to the control group, both in absolute levels or relatively to body weight.

There were no differences in body weight and food intake between the different treatment groups as compared to the control group.

There appeared to be no differences in ALT and AST levels between the different treatment groups as compared to the control group.

Lipid Plasma Parameters

After 5 weeks of treatment plasma triglycerides were significantly decreased in the phytosterol group as compared to the control group (with 36%, p=0.021), while the plasma triglycerides of the extract group were not significantly affected.

Plasma HDL was not affected by extract or phytosterol treatment as compared to the control group.

Conclusion

The data of the present study show that in female APOE*3Leiden.CETP mice, 100 mg/kg/d extract IMD-XT0022 was able to improve lipid metabolism. This was reflected by a significant decrease in plasma cholesterol. This effect was further supported by lipoprotein profiling, which confirmed a decrease in the VLDL cholesterol and phospholipids peak. No toxic side effects were observed and liver lipid profiles were also improved.

Example 7

Further Results and Safety Aspects

Liver lipids were determined according to Havekes et al. (Biochem. J. 1987; 247: 739-746). Briefly, 10-20 μg of tissue was homogenized in phosphate buffered saline and samples were taken for measurement of protein content (Lowry et al., J. Biol. Chem. 1951; 193:265-75). Lipids were extracted and separated by high performance thin layer chromatography (HPTLC) on silica gel plates. Lipid spots were stained with color reagent (5 g $MnCl_2.4H_2O$, 32 ml 95-97% $H_2SO_4$ added to 960 ml of $CH_3OH:H_2O$ (1:1 v/v)) and quantified using TINA® version 2.09 software (Raytest, Straubenhardt, Germany).

Values given are mean values (i.e. average absolute values±standard deviation) expressed as μg/mg protein of 10 mice per group.

| Liver lipids (μg/mg liver protein) | Free cholesterol | Triglycerides | Cholesteryl esters |
|---|---|---|---|
| Control group | 14.3 ± 1.4 | 119.9 ± 24.7 | 32.4 ± 3.7 |
| Extract group | 12.6 ± 1.2 | 93.5 ± 15.4 | 25.4 ± 2.5 |
| P-value (Independent sample t-test) | 0.008 | 0.012 | <0.001 |

After 5 weeks of treatment hepatic free cholesterol, hepatic triglycerides and cholesteryl esters were all significantly decreased in the group that received IMD-XT0022 (extract group) as compared to the control group.

These results demonstrate that no accumulation of cholesterol, triglycerides and cholesteryl esters was observed. Thus, the beneficial effects observed in the context of the present invention and inter alia confirmed in the reduced plasma cholesterol, cholesteryl ester and triglyceride levels do not result from undesired accumulation of these substances in liver tissue.

No adverse effects were found on plasma triglycerides or HDL, on liver weight and liver damage markers (in particular ALT (aspartate aminotransferase) and AST (alanine aminotransferase). Additionally, no adverse mutagenic effect was observed in the *Salmonella typhimurium* reverse mutation assay (according to OECD Guideline 471, also called "AMES-test").

The invention claimed is:

1. A method of treatment of a disease, disorder or condition comprising administering to an individual in need of such treatment a pharmaceutically or nutraceutically effective amount of a compound of formula I, or an extract including a compound of formula I, as active ingredient, where the compound may be in free form or in the form of a pharmaceutically acceptable salt, wherein the disease, disorder or condition responds to the modulation of Liver X receptor and is selected from the group consisting of Syndrome X, hypocholesterolemia, low HDL levels, lack of lipid homeostasis and obesity;

wherein formula I includes:

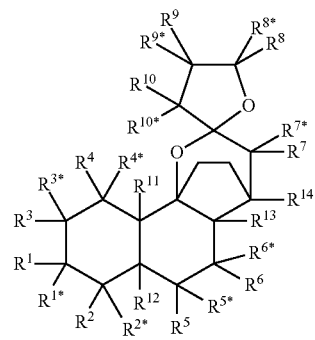

(I)

wherein the substituents in formula I are defined as follows:

each of $R^1$, $R^{1*}$, $R^2$, $R^{2*}$, $R^3$, $R^{3*}$, $R^4$, $R^{4*}$, $R^5$, $R^{5*}$, $R^6$, $R^{6*}$, $R^7$, $R^{7*}$, $R^8$, $R^{8*}$, $R^9$, $R^{9*}$, $R^{10}$, $R^{10*}$, $R^{11}$, $R^{12}$, $R^{13}$ and $R^{14}$ is hydrogen, unsubstituted or substituted $C_{1-7}$alkyl, hydroxyl, halo, unsubstituted or substituted $C_{1-7}$alkoxy, $C_{2-7}$alkenyl, $C_{2-7}$alkynyl, unsubstituted or substituted $C_{2-7}$alkanoyloxy, amino, NHR or NRR', wherein R and R' are, independently of each other, selected from the group consisting of $C_{1-7}$alkyl, substituted $C_{1-7}$alkyl, unsubstituted or substituted $C_{6-14}$aryl, unsubstituted or substituted $C_{3-12}$cycloalkyl, unsubstituted or substituted $C_{2-7}$alkanoyl, unsubstituted or substituted $C_{1-7}$alkanesulfonyl, unsubstituted or substituted arylsulfonyl, unsubstituted or substituted $C_{3-12}$cycloalkyl-CO or $C_{6-14}$aryl-CO—, with the proviso that not more than one of R and R' can be unsubstituted or substituted $C_{2-7}$alkanoyl, unsubstituted or substituted $C_{3-12}$cycloalkyl-CO— or $C_{6-14}$aryl-CO—, the other can be as just defined;

and wherein the substituents for substituted $C_{1-7}$alkyl, substituted $C_{1-7}$alkoxy, substituted $C_{1-2}$alkanoyloxy, substituted $C_{6-14}$aryl, substituted $C_{3-12}$cycloalkyl, unsubstituted or substituted $C_{1-7}$alkanesulfonyl, unsubstituted or substituted arylsulfonyl, substituted $C_{3-12}$cycloalkyl-CO— and $C_{6-14}$aryl-CO— can be one or more substituents independently selected from the group consisting of hydroxyl, $C_{1-7}$alkoxy, $C_{2-7}$alkanoyloxy, $C_{3-12}$cycloalkyl, $C_{6-14}$aryl, halo, =O, =S, =NH or =NR'' wherein R'' is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO or $C_{6-14}$aryl-CO—;

or each one or more of the pairs of geminal symbols $R^1$ and $R^{1*}$; $R^2$ and $R^{2*}$; $R^3$ and $R^{3*}$; $R^4$ and $R^{4*}$; $R^5$ and $R^{5*}$; $R^6$ and $R^{6*}$; $R^9$ and $R^{9*}$; and $R^{10}$ and $R^{10*}$ together can form =O, =S, =NH or =NR''' wherein R''' is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO or $C_{6-14}$aryl-CO—; with the proviso, that if other double bonds are present, they are either isolated or conjugated from the binding double bonds for =O, =S, =NH or =NR''' with NR''' as just defined;

or each of one or more pairs of vicinal symbols $R^{1*}$, $R^{2*}$, $R^{3*}$, $R^{4*}$, $R^{5*}$, $R^{6*}$, $R^{11}$ and $R^{12}$ can, together with the bond of the ring atoms to which they are bound, form a double bond, where if more than one double bond is present in the compound of the formula I, the double bonds are conjugated double bonds (double bonds separated by a single bond) or isolated double bonds (double bonds separated by two or more single bonds), or both types are present;

or $R^1$ and $R^2$, together with the ring atoms to which they are attached, form a 4- to 8 membered unsaturated or partially saturated or saturated carbocyclic ring, with the proviso that that if $R^1$ is part of a double bond in the ring, then $R^{1*}$ also is part of that double bond and if $R^2$ is part of a double bond in the ring, then $R^{2*}$ is also part of that double bond, in which case said double bond or double bonds are not formed by $R^{1*}$ and $R^{2*}$ (meaning they can only form a bond with each other contributing to the double bond if they are not part of the double bond formed in the ring which is not between the carbon atoms that carry $R^{1*}$ and $R^{2*}$);

or $R^1$ and $R^3$, together with the ring atoms to which they are attached, form a 4- to 8-membered unsaturated or partially saturated or saturated carbocyclic ring, with the proviso that if $R^1$ is part of a double bond in the ring, then $R^{1*}$ also is part of that double bond and if $R^3$ is part of a double bond in the ring, then $R^{3*}$ is also part of that double bond, in which case said double bond or double bonds are not formed by $R^{1*}$ and $R^{3*}$ (meaning they can only form a bond with each other contributing to the double bond if they are not part of the double bond formed in the ring which is not between the carbon atoms that carry $R^{1*}$ and $R^{3*}$);

where the carbocyclic rings in all cases can be unsubstituted or substituted by one or more moieties independently selected from the group consisting of hydroxyl, $C_{1-7}$alkyl, $C_{1-7}$alkoxy, $C_{2-7}$alkanoyloxy, $C_{3-12}$cycloalkyl, $C_{6-14}$aryl, halo, =O, =S, =NH or =NR'' wherein R'' is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO and $C_{6-14}$aryl-CO—;

or each one or more pairs of symbols;

or a pharmaceutically acceptable salt, thereof.

2. A method of treatment of a disease, disorder or condition comprising administering to an individual in need of such treatment a pharmaceutically or nutraceutically effective amount of a compound of formula I, or an extract including a compound of formula I, as active ingredient, where the compound may be in free form or in the form of a pharmaceutically acceptable salt, wherein the disease, disorder or condition responds to the modulation of Liver X receptor and is selected from the group consisting of Syndrome X, hypocholesterolemia, low HDL levels, lack of lipid homeostasis and obesity wherein formula I includes:

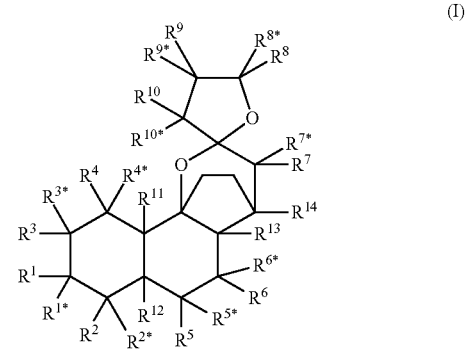

wherein the substituents in formula I are defined as follows:

$R^1$ and $R^{1*}$ are selected from hydrogen, $C_{1-7}$alkyl, hydroxyl or $C_{1-7}$alkyoxy;

$R^2$ and $R^{2*}$ are selected from $C_{1-7}$alkyl, hydroxyl-$C_{1-7}$alkyl and $C_{1-7}$alkyl substituted by oxo;

$R^3$ is hydrogen or hydroxyl;

$R^4$ is hydrogen or hydroxyl;

$R^{4*}$ is hydrogen;

$R^5$ is hydrogen or hydroxyl;

$R^{5*}$ is hydrogen;

$R^6$ is hydrogen or hydroxyl;

$R^{6*}$ is hydrogen;

$R^7$ is $C_{1-7}$alkyl;

$R^{7*}$ is hydrogen;

$R^8$ is $C_{1-7}$alkyl;

$R^{8*}$ is $C_{1-7}$alkyl;

$R^9$ is $C_{1-7}$alkyl or hydroxyl-$C_{1-7}$alkyl;

$R^{9*}$ is hydrogen;

$R^{10*}$ is hydroxyl;

$R^{12}$ is hydroxyl;

$R^{13}$ is $C_{1-7}$alkyl; and $R^{14}$ is hydrogen or hydroxyl;

or one or more of the following moieties may also combine to give the respective meanings:

$R^{2*}$ and $R^{12}$ together form a double bond;

$R^{1*}$ and $R^{2*}$ together form a double bond;

$R^{3*}$ and $R^{4*}$ together form a double bond;

$R^{5*}$ and $R^{6*}$ together form a double bond;

$R^{11}$ and $R^{12}$ together form double bond;

$R^5$ and $R^{12}$ together form a double bond;

$R^1$ and $R^{1*}$ together form oxo;

$R^3$ and $R^{3*}$ together form oxo;

$R^5$ and $R^{5*}$ together form oxo;

$R^6$ and $R^{6*}$ together form oxo;

or $R^1$ and $R^3$ together may also form a moiety of the formula

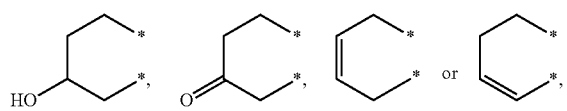

where the ends of the bonds marked with an asterisk (*) bind at the position of $R^1$ (upper asterisk) and $R^3$ (lower asterisk), respectively;

or $R^1$, $R^{1*}$ and $R^2$ together form a moiety of the formula

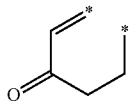

where the ends of the bonds marked with an asterisk (*) bind at the position of $R^1$ and $R^{1*}$ (upper asterisk) and $R^2$ (lower asterisk), respectively;

or $R^1$ and $R^2$ together form a moiety of the formula

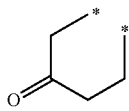

where the ends of the bonds marked with an asterisk (*) bind at the position of $R^1$ (upper asterisk) and $R^2$ (lower asterisk);

where any double bonds present (including those of oxo) are isolated or conjugated, or both types are present;

or a pharmaceutically acceptable salt, thereof.

3. A method of treatment of a disease, disorder or condition comprising administering to an individual in need of such treatment a pharmaceutically or nutraceutically effective amount of a compound of formula I, or an extract including a compound of formula I, as active ingredient, where the compound may be in free form or in the form of a pharmaceutically acceptable salt, wherein the disease, disorder or condition responds to the modulation of Liver X receptor and is selected from the group consisting of Syndrome X, hypocholesterolemia, low HDL levels, lack of lipid homeostasis and obesity wherein formula I includes:

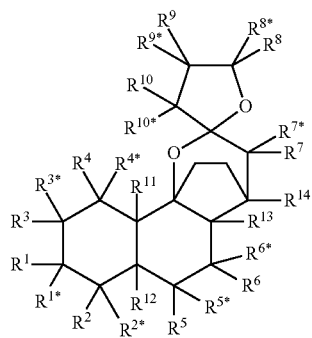

wherein each of $R^1$, $R^{1*}$, $R^2$, $R^{2*}$, $R^3$, $R^{3*}$, $R^4$, $R^{4*}$, $R^5$, $R^{5*}$, $R^6$, $R^{6*}$, $R^7$, $R^{7*}$, $R^8$, $R^{8*}$, $R^9$, $R^{9*}$, $R^{10}$, $R^{10*}$, $R^{11}$, $R^{12}$, $R^{13}$ and $R^{14}$ is hydrogen, unsubstituted or substituted $C_{1-7}$alkyl, hydroxyl, halo, unsubstituted or substituted $C_{1-7}$alkoxy, $C_{2-7}$alkenyl, $C_{2-7}$alkynyl, unsubstituted or substituted $C_{2-7}$alkanoyloxy, amino, NHR or NRR', wherein R and R' are, independently of each other, selected from the group consisting of $C_{1-7}$alkyl, substituted $C_{1-7}$alkyl, unsubstituted or substituted $C_{6-14}$aryl, unsubstituted or substituted $C_{3-12}$cycloalkyl, unsubstituted or substituted $C_{2-7}$alkanoyl, unsubstituted or substituted $C_{1-7}$alkanesulfonyl, unsubstituted or substituted arylsulfonyl, unsubstituted or substituted $C_{3-12}$cycloalkyl-CO or $C_{6-14}$aryl-CO—, with the proviso that not more than one of R and R' can be unsubstituted or substituted $C_{2-7}$alkanoyl, unsubstituted or substituted $C_{3-12}$cycloalkyl-CO— or $C_{6-14}$aryl-CO—, the other can be as just defined;

and wherein the substituents for substituted $C_{1-7}$alkyl, substituted $C_{1-7}$alkoxy, substituted $C_{1-2}$alkanoyloxy, substituted $C_{6-14}$aryl, substituted $C_{3-12}$cycloalkyl, unsubstituted or substituted $C_{1-7}$alkanesulfonyl, unsubstituted or substituted arylsulfonyl, substituted $C_{3-12}$cycloalkyl-CO— and $C_{6-14}$aryl-CO— can be one or more substituents independently selected from the group consisting of hydroxyl, $C_{1-7}$alkoxy, $C_{2-7}$alkanoyloxy, $C_{3-12}$cycloalkyl, $C_{6-14}$aryl, halo, =O, =S, =NH or =NR'' wherein R'' is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO or $C_{6-14}$aryl-CO—;

or each one or more of the pairs of geminal symbols $R^1$ and $R^{1*}$; $R^2$ and $R^{2*}$; $R^3$ and $R^{3*}$; $R^4$ and $R^{4*}$; $R^5$ and $R^{5*}$; $R^6$ and $R^{6*}$; $R^9$ and $R^{9*}$; and $R^{10}$ and $R^{10*}$ together can form =O, =S, =NH or =NR''' wherein R''' is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO or $C_{6-14}$aryl-CO—; with the proviso, that if other double bonds are present, they are either isolated or conjugated from the binding double bonds for =O, =S, =NH or =NR''' with NR''' as just defined;

or each of one or more pairs of vicinal symbols $R^{1*}$, $R^{2*}$, $R^{3*}$, $R^{4*}$, $R^{5*}$, $R^{6*}$, $R^{11}$ and $R^{12}$ can, together with the bond of the ring atoms to which they are bound, form a double bond, where if more than one double bond is present in the compound of the formula I, the double bonds are conjugated double bonds (double bonds separated by a single bond) or isolated double bonds (double bonds separated by two or more single bonds), or both types are present;

or $R^1$ and $R^2$, together with the ring atoms to which they are attached, form a 4- to 8 membered unsaturated or partially saturated or saturated carbocyclic ring, with the proviso that that if $R^1$ is part of a double bond in the ring, then $R^{1*}$ also is part of that double bond and if $R^2$ is part of a double bond in the ring, then $R^{2*}$ is also part of that double bond, in which case said double bond or double bonds are not formed by $R^{1*}$ and $R^{2*}$ (meaning they can only form a bond with each other contributing to the double bond if they are not part of the double bond formed in the ring which is not between the carbon atoms that carry $R^{1*}$ and $R^{2*}$);

or $R^1$ and $R^3$, together with the ring atoms to which they are attached, form a 4- to 8-membered unsaturated or partially saturated or saturated carbocyclic ring, with the proviso that if $R^1$ is part of a double bond in the ring, then $R^{1*}$ also is part of that double bond and if $R^3$ is part of a double bond in the ring, then $R^{3*}$ is also part of that double bond, in which case said double bond or double bonds are not formed by $R^{1*}$ and $R^{3*}$ (meaning they can only form a bond with each other contributing to the double bond if they are not part of the double bond formed in the ring which is not between the carbon atoms that carry $R^{1*}$ and $R^{3*}$);

where the carbocyclic rings in all cases can be unsubstituted or substituted by one or more moieties independently selected from the group consisting of hydroxyl, $C_{1-7}$alkyl, $C_{1-7}$alkoxy, $C_{2-7}$-alkanoyloxy, $C_{3-12}$cycloalkyl, $C_{6-14}$aryl, halo, =O, =S, =NH or =NR" wherein R" is $C_{1-7}$alkyl, $C_{6-14}$aryl, $C_{6-14}$aryl-$C_{1-7}$alkyl, $C_{3-12}$cycloalkyl, $C_{3-12}$cycloalkyl-$C_{1-7}$alkyl, carboxyl, $C_{1-7}$alkoxycarbonyl, $C_{2-7}$alkanoyl, $C_{3-12}$cycloalkyl-CO and $C_{6-14}$aryl-CO—;

or each one or more pairs of symbols, and wherein the substituents in formula I are further defined as follows:

$R^{1*}$ and $R^{2*}$ together form a double bond;
$R^{3*}$ and $R^{4*}$ together form a double bond
$R^{5*}$ and $R^{6*}$ together form a double bond, or each of them is hydrogen or one is hydroxyl, the other hydrogen;
and $R^{11}$ and $R^{12}$ together form a double bond;
excluding those definitions of other moieties where pairs of such substituents form =O, =S, =NH or =NR'" or double bonds or carbocyclic rings;
or wherein $R^1$ and $R^3$ together form a moiety of the formula

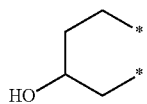 [SMILES: *CCC(O)C*]

where the ends of the bonds marked with an asterisk (*) bind at the position of $R^1$ (upper asterisk) and $R^3$ (lower asterisk), respectively;
$R^{1*}$ and $R^{2*}$ together form a double bond;
$R^{3*}$ and $R^{4*}$ together form a double bond
$R^{5*}$ and $R^{6*}$ together form a double bond;
and $R^{11}$ and $R^{12}$ together form a double bond;
excluding those definitions of other moieties where pairs of such substituents form =O, =S, =NH or =NR'" or double bonds or carbocyclic rings;
or wherein or $R^1$, $R^{1*}$ and $R^2$ together form a moiety of the formula

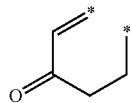

where the ends of the bonds marked with an asterisk (*) bind at the position of $R^1$ and $R^{1*}$ (upper asterisk) and $R^2$ (lower asterisk), respectively;
$R^3$ and $R^{3*}$ together form oxo;
$R^{4*}$ and $R^{11}$ together form a double bond;
and $R^{5*}$ and $R^{12}$ together form a double bond;
excluding those definitions of other moieties where pairs of such substituents form =O, =S, =NH or =NR'" or double bonds or carbocyclic rings;
or wherein or $R^1$, $R^{1*}$ and $R^2$ together form a moiety of the formula

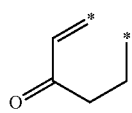

where the ends of the bonds marked with an asterisk (*) bind at the position of $R^1$ and $R^{1*}$ (upper asterisk) and $R^2$ (lower asterisk), respectively;

$R^{3*}$ and $R^{4*}$ together form a double bond, or each of them is hydroxyl;
$R^{5*}$ and $R^{6*}$ together form a double bond;
and $R^{11}$ and $R^{12}$ together form a double bond;
excluding those definitions of other moieties where pairs of such substituents form =O, =S, =NH or =NR'" or double bonds or carbocyclic rings;
or wherein $R^{1*}$ and $R^{2*}$ together form a double bond;
$R^{3*}$ and $R^{4*}$ together form a double bond
$R^6$ and $R^{6*}$ together form oxo,
and $R^{11}$ and $R^{12}$ together form a double bond;
excluding those definitions of other moieties where pairs of such substituents form =O, =S, =NH or =NR'" or double bonds or carbocyclic rings;
or wherein or $R^1$ and $R^2$ together form a moiety of the formula

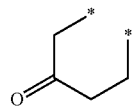

where the ends of the bonds marked with an asterisk (*) bind at the position of $R^1$ (upper asterisk) and $R^2$ (lower asterisk);
$R^3$ and $R^{3*}$ together form oxo;
$R^{4*}$ and $R^{11}$ together form a double bond;
and $R^{5*}$ and $R^{12}$ together form a double bond;
excluding those definitions of other moieties where pairs of such substituents form =O, =S, =NH or =NR'" or double bonds or carbocyclic rings, except that $R^6$ and $R^{6*}$ can also form oxo;
or wherein $R^5$ and $R^{5*}$ together form oxo;
$R^6$ and $R^{6*}$ form oxo;
$R^{1*}$ and $R^{2*}$ together form a double bond;
$R^{3*}$ and $R^{4*}$ together form a double bond;
$R^{11}$ and $R^{12}$ together form a double bond;
excluding those definitions of other moieties where pairs of such substituents form =O, =S, =NH or =NR'" or double bonds or carbocyclic rings;
or wherein $R^{1*}$ and $R^{2*}$ together form a double bond
$R^{3*}$ and $R^{4*}$ together form a double bond;
$R^{11}$ and $R^{12}$ together form a double bond;
excluding those definitions of other moieties where pairs of such substituents form =O, =S, =NH or =NR'" or double bonds or carbocyclic rings;
or wherein or $R^1$, $R^{1*}$ and $R^{2*}$ together form a moiety of the formula

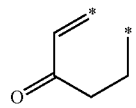

where the ends of the bonds marked with an asterisk (*) bind at the position of $R^1$ and $R^{1*}$ (upper asterisk) and $R^2$ (lower asterisk), respectively;
$R^3$ and $R^{3*}$ together form oxo;
$R^{4*}$ and $R^{11}$ together form a double bond;
$R^{5*}$ and $R^{6*}$ together form a double bond, or each of them is hydrogen or one is hydroxyl, the other hydrogen;
excluding those definitions of other moieties where pairs of such substituents form =O, =S, =NH or =NR'" or double bonds or carbocyclic rings;

or wherein $R^1$ and $R^{1*}$ together form oxo;
$R^{3*}$ and $R^{4*}$ together form a double bond;
$R^{5*}$ and $R^{6*}$ together form a double bond; and
$R^{11}$ and $R^{12}$ together form a double bond;
excluding those definitions of other moieties where pairs of such substituents form =O, =S, =NH or =NR''' or double bonds or carbocyclic rings;
or a pharmaceutically acceptable salt, thereof.

4. A method of treatment of a disease, disorder or condition comprising administering to an individual in need of such treatment a pharmaceutically or nutraceutically effective amount of a compound as active ingredient, wherein the compound is selected from one or more compounds selected from the group consisting of:

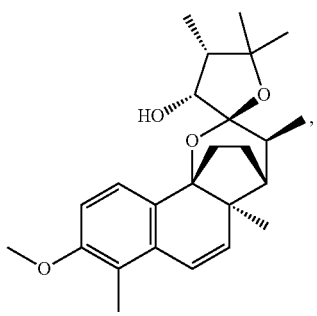

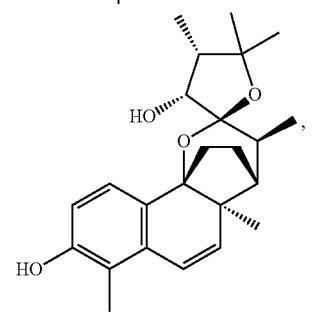

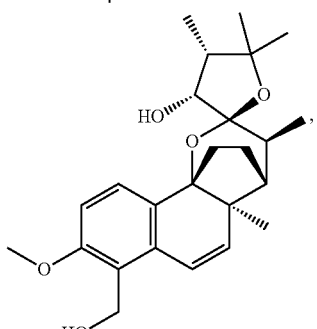

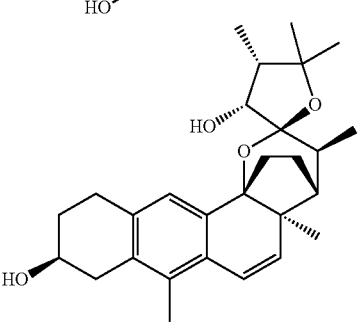

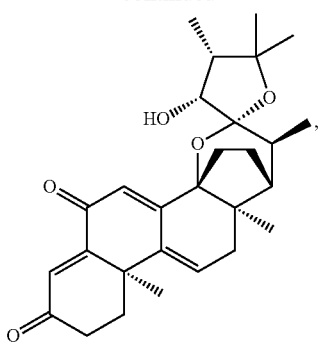

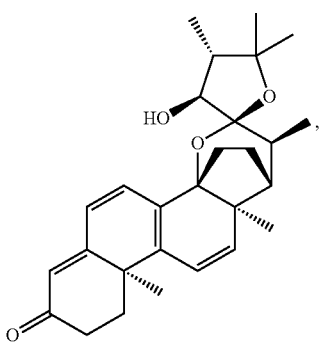

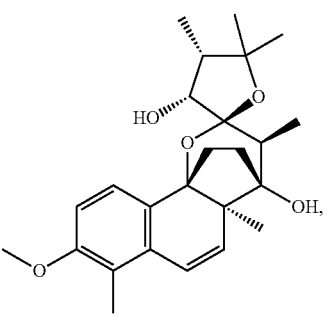

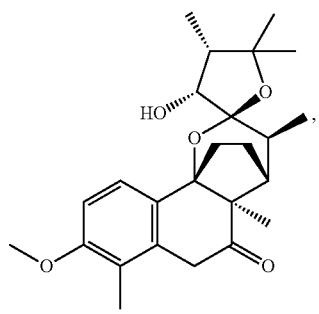

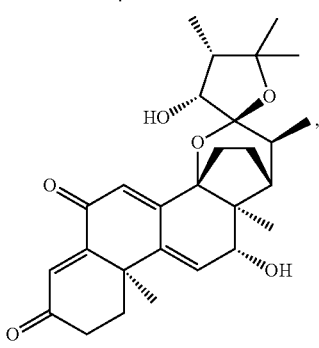

75
-continued
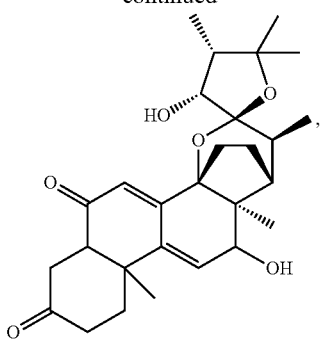,
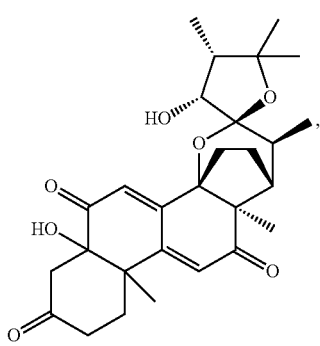,
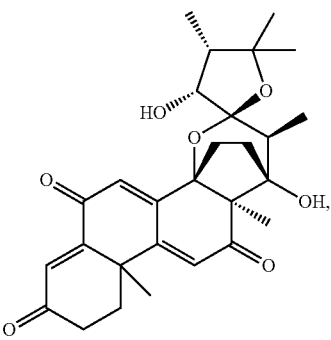,
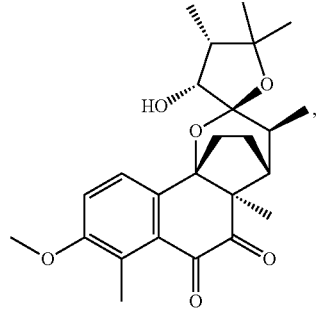,
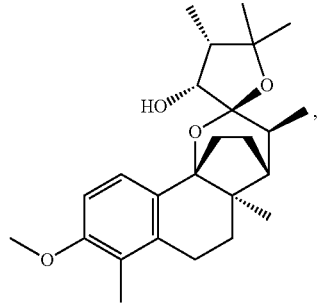,
76
-continued
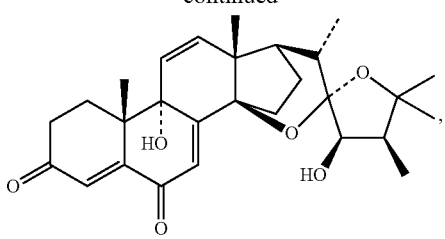,
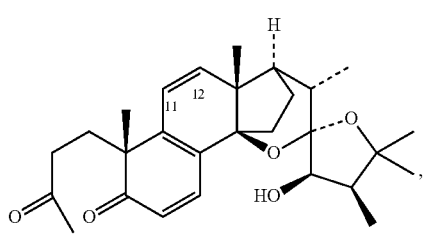,
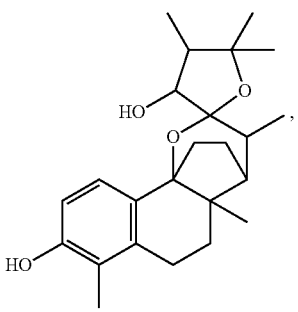,
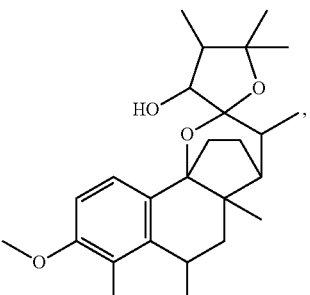,
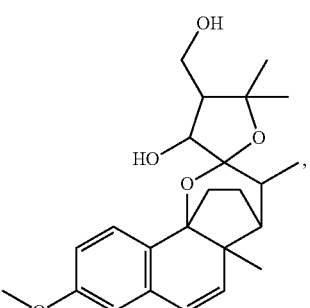,
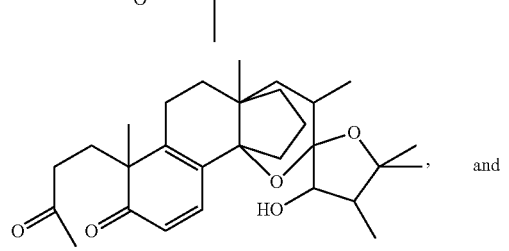, and or an extract including said compound,
wherein the compound selected may be in free form or in the form of a pharmaceutically acceptable salt, wherein the disease, disorder or condition responds to the modulation of Liver X receptor and is selected from the group consisting of Syndrome X, hypocholesterolemia, low HDL levels, lack of lipid homeostasis and obesity.

* * * * *

SEQUENCE LISTING

<160> NUMBER OF SEQ ID NOS: 6

<210> SEQ ID NO 1
<211> LENGTH: 283
<212> TYPE: DNA
<213> ORGANISM: Agaricus subrufescens MUCL 52948
<220> FEATURE:
<221> NAME/KEY: misc_feature
<222> LOCATION: (1)..(283)
<223> OTHER INFORMATION: ITS 1

<400> SEQUENCE: 1

```
ttgaattatg tttctagata ggttgtagct ggctctttag agcatgtgca cgcctgtttg      60
gacttcattt tcatccacct gtgcacctat tgtagtcttt ggttgggtta ggaggaagtg     120
gtcattgtgt cagcatctgc tggatgtgag gatttgcatt gtgaaagctt tgctgtcctt     180
gatgtgatca tggaatctct ttctcactag agtctatgtc actcattata ctctgtcgaa     240
```
tgtcattgaa tgtctttaca tgggcttgta tgcctatgaa aat        283

<210> SEQ ID NO 2
<211> LENGTH: 283
<212> TYPE: DNA
<213> ORGANISM: Agaricus subrufescens MUCL 52949
<220> FEATURE:
<221> NAME/KEY: misc_feature
<222> LOCATION: (1)..(283)
<223> OTHER INFORMATION: ITS 1

<400> SEQUENCE: 2
ttgaattatg tttctagata ggttgtagct ggctctttag agcatgtgca cgcctgtttg        60
gacttcattt tcatccacct gtgcacctat tgtagtcttt ggttgggtta ggaggaagtg        120
gtcattgtgt cagcatctgc tggatgtgag gatttgcatt gtgaaagctt tgctgtcctt        180
gatgtgatca tggaatctct ttctcactag agtctatgtc actcattata ctctgtcgaa        240
tgtcattgaa tgtctttaca tgggcttgta tgcctatgaa aat        283

<210> SEQ ID NO 3
<211> LENGTH: 283
<212> TYPE: DNA
<213> ORGANISM: Agaricus subrufescens MUCL 52947
<220> FEATURE:
<221> NAME/KEY: misc_feature
<222> LOCATION: (1)..(283)
<223> OTHER INFORMATION: ITS 1

<400> SEQUENCE: 3
ttgaattatg tttctagatg ggttgtagct ggctctttag agcatgtgca cgcctgtttg        60
gacttcattt tcatccacct gtgcacctat tgtagtcttt ggttgggtta ggaggaagtg        120
gtcattgtgt cagcatctgc tggatgtgag gacttgcatt gtgaaagctt tgctgtcctt        180
gatgtgatca tggaatctct ttctcactag agtctatgtc actcattata ctctgtcgaa        240
tgtcattgaa tgtctttaca tgggcttgta tgcctatgaa aat        283

<210> SEQ ID NO 4
<211> LENGTH: 283
<212> TYPE: DNA
<213> ORGANISM: Agaricus subrufescens ATCC34722
<220> FEATURE:
<221> NAME/KEY: misc_feature
<222> LOCATION: (1)..(283)
<223> OTHER INFORMATION: ITS 1

<400> SEQUENCE: 4
ttgaattatg tttctaaatg ggttgtagct ggctctttag agcatgtgca cgcctgtttg        60
gacttcattt tcatccacct gtgcacctat tgtagtcttt ggttgggtta ggaggaagtg        120
gtcatcctat cagcatctgc tggatgtgag gacttgcatt gtgaaaactt tgctgtcctc        180
tatgtgatca tgaaatcact ttctcaccgg agtctatgtc attcattata ctctgtcgaa        240
tgtcattgaa tgtctttaca tgggcttgta tgcctatgaa aat        283

<210> SEQ ID NO 5
<211> LENGTH: 322
<212> TYPE: DNA
<213> ORGANISM: Agaricus silvaticus STMA 10083
<220> FEATURE:
<221> NAME/KEY: misc_feature
<222> LOCATION: (1)..(322)
<223> OTHER INFORMATION: ITS 1

```
<400> SEQUENCE: 5
attattgaat tatgttttct agatggggttg tagctggccc tttggggcat gtgcacgcct      60
gtctggactt catttttcatc cacctgtgca cctattgtag tctttgtcgg gaaccattga    120
ggaagtggtc agcctatcag caattgctgg atgtgaggac ttgcaatgca gcagtgcgtt    180
gctgtccttt acttggccac ggaatcggtt tcctgtcgga gtctatgtca tttattatac    240
cctgcagaat gtcattgaat gtctatacat gggcttgtat gcctatgaaa attgtaatac    300
aactttcagc aacggatctc tt                                              322

<210> SEQ ID NO 6
<211> LENGTH: 322
<212> TYPE: DNA
<213> ORGANISM: Agaricus silvaticus STMA 10072
<220> FEATURE:
<221> NAME/KEY: misc_feature
<222> LOCATION: (1)..(322)
<223> OTHER INFORMATION: ITS 1
<220> FEATURE:
<221> NAME/KEY: misc_feature
<222> LOCATION: (113)..(113)
<223> OTHER INFORMATION: n is a, c, g, or t

<400> SEQUENCE: 6
attattgaat tatgtttcta gatgggttgt agctggccct ttggggcatg tgcacgcctg     60
tcctggactt catttttcatc cacctgtgca cctattgtag tctttgtcgg gangcattga   120
ggaagtggtc agcctatcag cagttgctgg atgtgaggac ttgcaatgca gcagtgcgtt   180
gctgtccttt acttggccac ggaatcggtt tcctgtcgga gtctatgtca tttattatac   240
cctgcagcat gtcattgaat gtctatacat gggcttgtat gcctatgaaa attgtaatac   300
aactttcagc aacggatctc tt                                            322
```